(12) United States Patent
Nakanishi et al.

(10) Patent No.: US 8,496,941 B2
(45) Date of Patent: Jul. 30, 2013

(54) VECTORS FOR GENERATING PLURIPOTENT STEM CELLS AND METHODS OF PRODUCING PLURIPOTENT STEM CELLS USING THE SAME

(75) Inventors: Mahito Nakanishi, Tsukuba (JP); Ken Nishimura, Tsukuba (JP); Manami Ohtaka, Tsukuba (JP); Masayuki Sano, Tsukuba (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 415 days.

(21) Appl. No.: 12/792,580

(22) Filed: Jun. 2, 2010

(65) Prior Publication Data

US 2010/0311171 A1   Dec. 9, 2010

Related U.S. Application Data

(60) Provisional application No. 61/183,724, filed on Jun. 3, 2009.

(51) Int. Cl.
| | |
|---|---|
| *A61K 39/12* | (2006.01) |
| *A61K 39/155* | (2006.01) |
| *C12N 5/00* | (2006.01) |
| *C12N 15/00* | (2006.01) |
| *C12N 15/86* | (2006.01) |

(52) U.S. Cl.
USPC .................. 424/211.1; 424/199.1; 424/204.1; 435/320.1; 435/325; 435/456

(58) Field of Classification Search
None
See application file for complete search history.

(56) References Cited

PUBLICATIONS

Jin et al. Recombinant Sendai virus provides a highly efficient gene transfer into human cord blood-derived hematopoietic stem cells. Gene Therapy 2003, vol. 10, pp. 272-277.*
Inoue et al. Recombinant Sendai virus vectors deleted in both the matrix and the fusion genes: efficient gene transfer with preferable properties. The Journal of Gene Medicine 2004, vol. 6, pp. 1069-1081.*
Takahashi et al. Induction of Pluripotent Stem Cells from Mouse Embryonic and Adult Fibroblast Cultures by Defined Factors. Cell 2006, vol. 126, p. 663-676.*
Nishio et al. Recombinant Sendai viruses with L1618V mutation in their L polymerase protein establish persistent infection. Virology 2004, vol. 329, pp. 289-301.*
A. Harui, et al., "Frequency and Stability of Chromosomal Integration of Adenovirus Vectors," Journal of Virology, Jul. 1999, pp. 6141-6146, vol. 73, No. 7.
D. Huangfu, et al., "Induction of pluripotent stem cells by defined factors is greatly improved by small-molecule compounds," Nature Biotechnology, Jun. 22, 2008, 13 pages total.

S. Hacein-Bey-Abina, et al., LMO2-Associated Clonal T Cell Proliferation in Two Patients after Gene Therapy for SCID-X1, Science, Research Article, Oct. 17, 2003, vol. 302, pp. 415-419.
E. Hurley, et al., "When Epstein-Barr Virus Persistently Infects B-Cell Lines, It Frequently Integrates," Journal of Virology, Mar. 1991, pp. 1245-1254, vol. 65, No. 3.
K. Kaji, et al., "Virus-free induction of pluripotency and subsequent excision of reprogramming factors," Nature, Apr. 2009, pp. 771-775, vol. 458.
R. Jaenisch, et al., "Stem Cells, the Molecular Circuitry of Pluripotency and Nuclear Reprogramming," Cell, Feb. 22, 2008, pp. 567-582, No. 132.
N. Fusaki, et al., "Efficient induction of transgene-free human pluripotent stem cells using a vector based on Sendai virus, and RNA virus that does not integrate into the host genome," Proc. Jpn. Acad., 2009, pp. 348-362, vol. 85.
F. Ohbayashi, et al., "Correction of chromosomal mutation and random integration in embryonic stem cells with helper-dependent adenoviral vectors," PNAS, Sep. 20, 2005, pp. 13628-13633, vol. 102, No. 38.
K. Okita, et al., "Generation of germline-competent induced pluripotent stem cells," Nature, Jul. 19, 2007, pp. 313-317, vol. 448.
K. Okita, et al., "Generation of Mouse Induced Pluripotent Stem Cells Without Viral Vectors," Science, Nov. 7, 2008, pp. 949-952, vol. 322.
M. Nakanishi, Regenerative Medicine, 2010, pp. 216-221, vol. 9.
K. Takahashi, et al., "Induction of Pluripotent Stem Cells from Adult Human Fibroblasts by Defined Factors," Cell, Nov. 30, 2007, pp. 1-12, vol. 131.
M. Stadtfeld, et al., "Induced Pluripotent Stem Cells Generated Without Viral Integration," Science, Nov. 7, 2008, pp. 945-949, vol. 332.
T. Wakayama, et al., "Differentiation of Embryonic Stem Cell Lines Generated from Adult Somatic Cells by Nuclear Transfer," Science, Apr. 27, 2001, pp. 740-743, vol. 292.
J. Yu, et al., "Human Induced Pluripotent Stem Cells Free of Vector and Transgene Sequences," Science, May 8, 2009, pp. 797-801, vol. 324.
K. Woltjen, et al., "piggyBac transposition reprograms fibroblasts to induced pluripotent stem cells," Nature, Apr. 9, 2009, pp. 766-770, vol. 458.

(Continued)

*Primary Examiner* — Louise Humphrey
(74) *Attorney, Agent, or Firm* — Sughrue Mion, PLLC

(57) ABSTRACT

Stem cell reprogramming genes cloned into a single sustained expression-type Sendai viral vector are shown to reprogram differentiated somatic cells into induced pluripotent stem (iPS) cells without integration of vector sequences into the host cell's genome. The genes are transduced into normal differentiated somatic cells via infection with recombinant Sendai virus. After expression of the reprogramming genes and subsequent induction of pluripotency, the vector genome RNA including the reprogramming genes is removed from the cell to establish an iPS cell that is genetically identical to the parent somatic differentiated cell thus reducing the risk of tumorigenic transformation caused by random integration of vector sequences into the host genome. The method promises to provide safe, autologous iPS cells that can be used for human cell replacement and regeneration therapeutic applications.

20 Claims, 27 Drawing Sheets
(22 of 27 Drawing Sheet(s) Filed in Color)

PUBLICATIONS

J. Yu, et al., "Induced Pluripotent Stem Cell Lines Derived from Human Somatic Cells," Science, Dec. 21, 2007, pp. 1917-1920, vol. 318.

H. Zhou, et al., "Generation of Induced Pluripotent Stem Cells Using Recombinant Proteins," Cell Stem Cell, May 8, 2009, pp. 1-8, vol. 4.

* cited by examiner

FIG.3
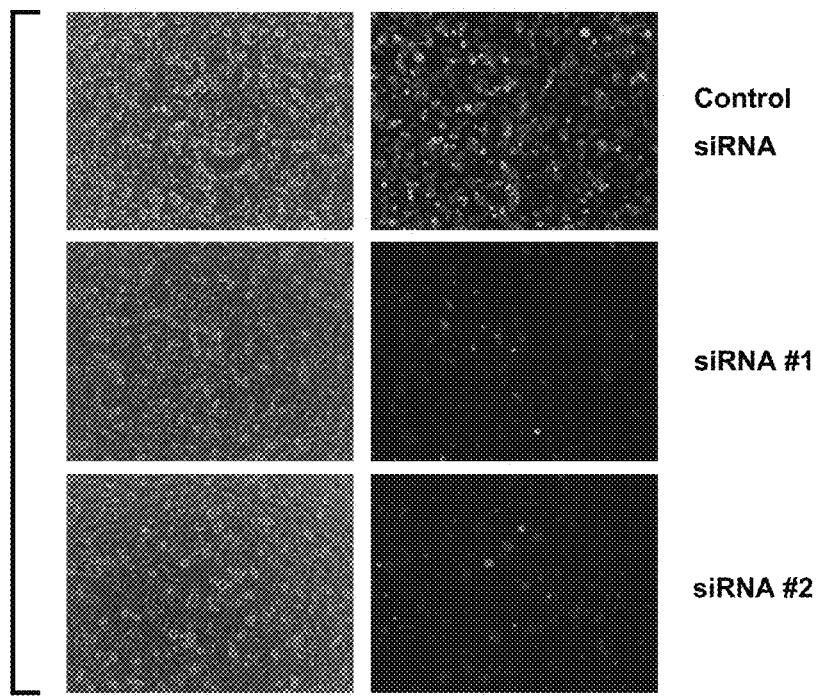
FIG.3A
(4th day)
Control siRNA
siRNA #1
siRNA #2
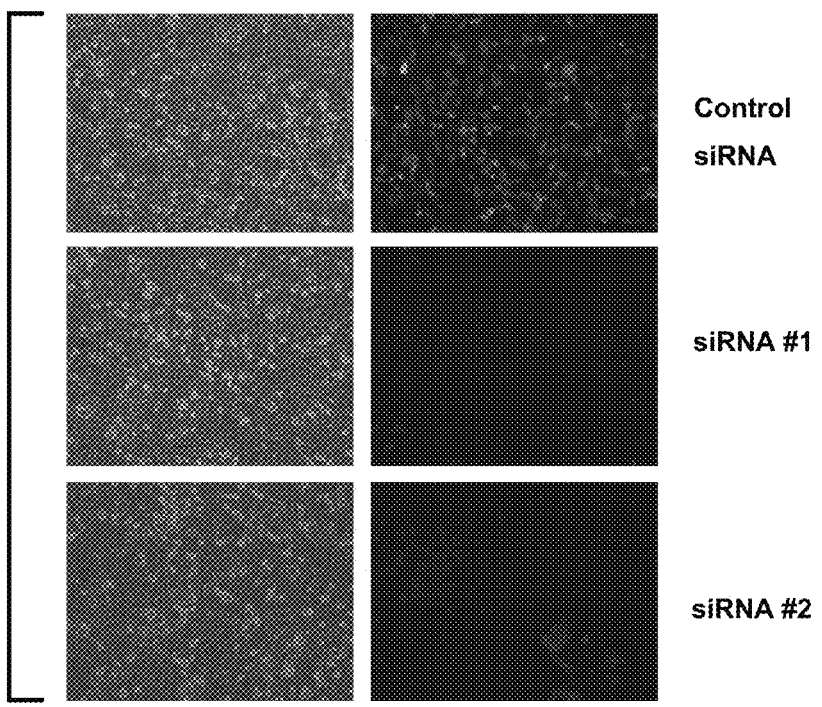
FIG.3B
(10th day)
Control siRNA
siRNA #1
siRNA #2

FIG.8
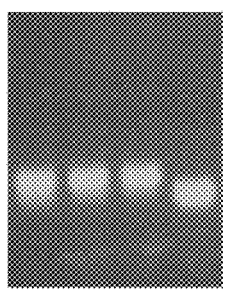
FIG. 8A
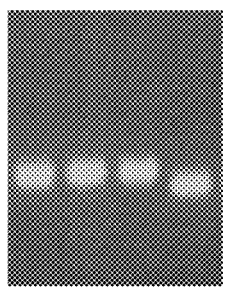
FIG. 8B
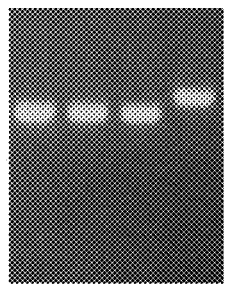
FIG. 8C

6 d.p.i.

8 d.p.i.

10 d.p.i.

FIG.13
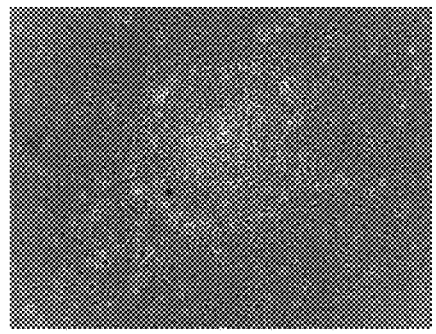
FIG.13A
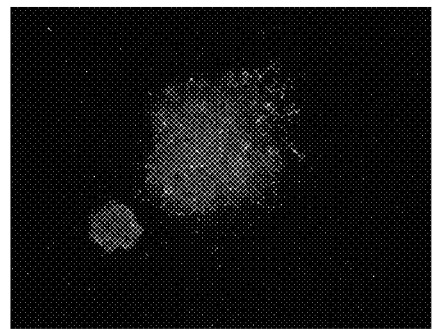
FIG.13B

FIG.16
FIG.16A  FIG.16B  FIG.16C
37°C,
5% $CO_2$
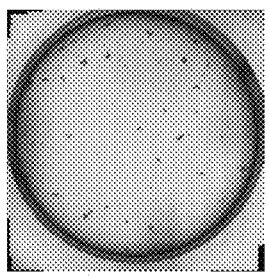 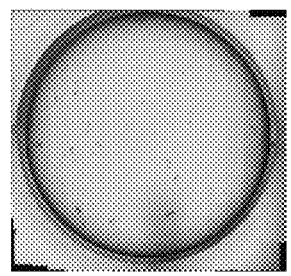 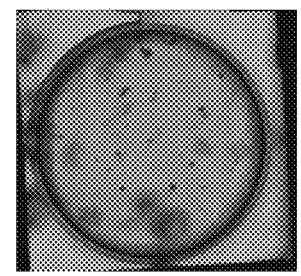
40°C,
2% $CO_2$
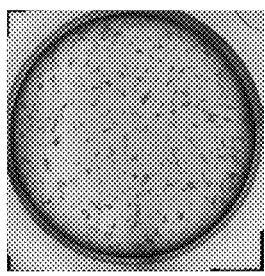 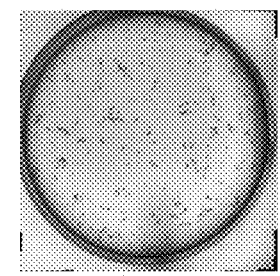 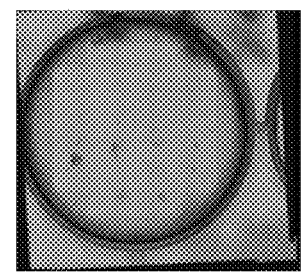

FIG.22
FIG.22A
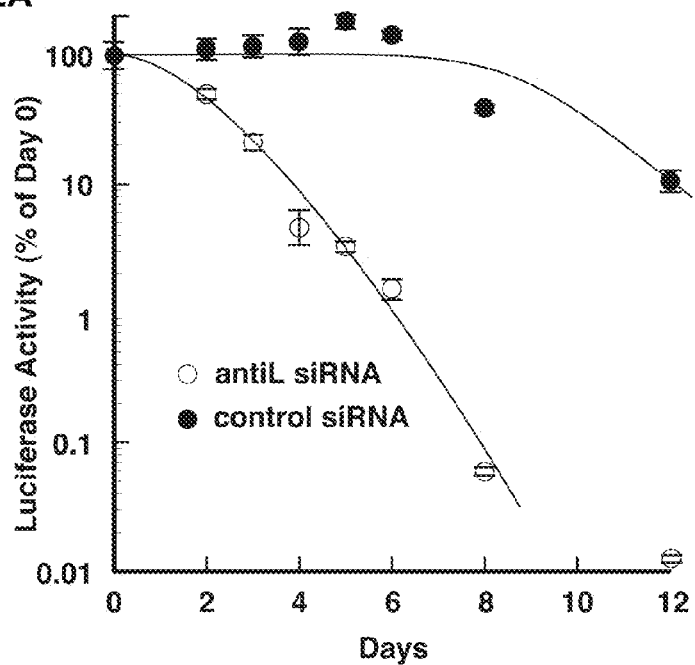
FIG.22B
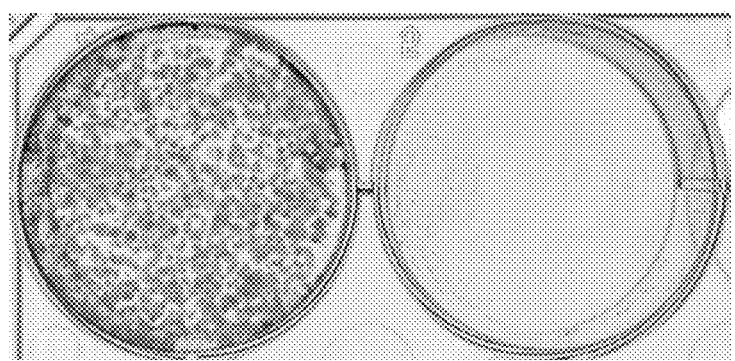

FIG.23
FIG.23A
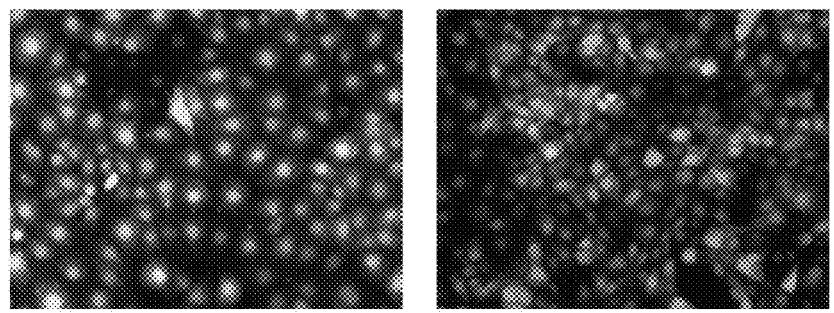
FIG.23B
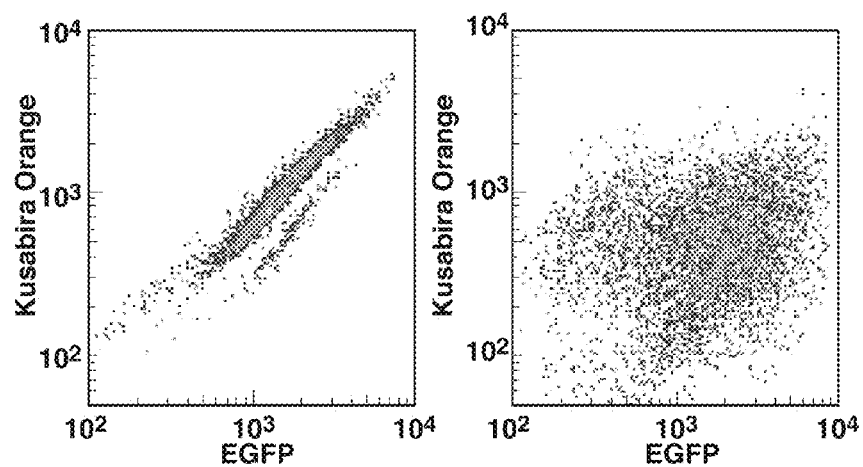
FIG.23C
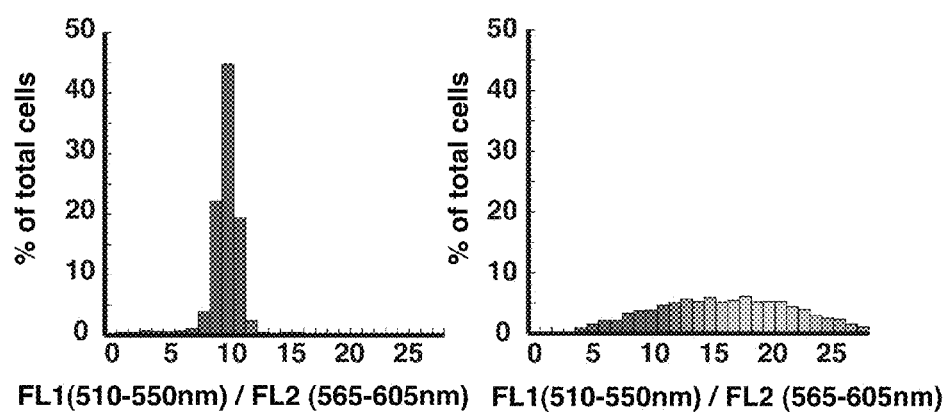

FIG.25
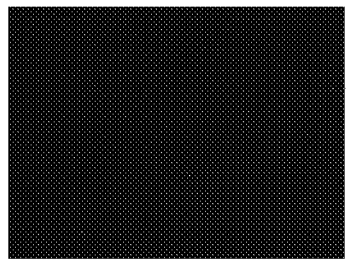
FIG.25A
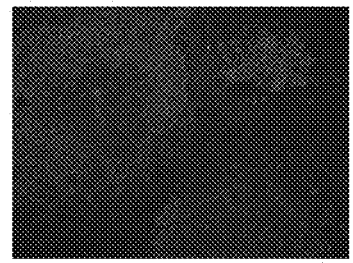
FIG.25B

FIG.26
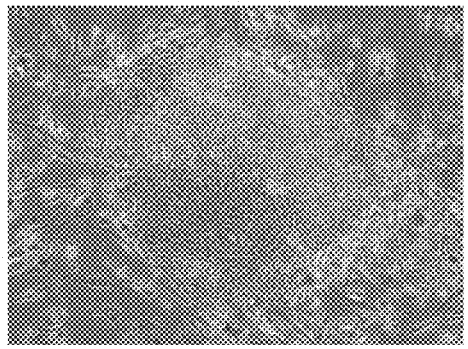
FIG.26A
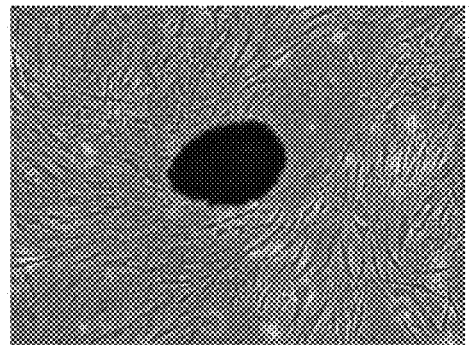
FIG.26B

FIG. 27
FIG. 27A
| | | | | |
|---|---|---|---|---|
| #19 | 1.000 | | | |
| #56 | 0.995 | 1.000 | | |
| #74 | 0.989 | 0.990 | 1.000 | |
| #106 | 0.988 | 0.989 | 0.998 | 1.000 |
| | #19 | #56 | #74 | #106 |
FIG. 27B
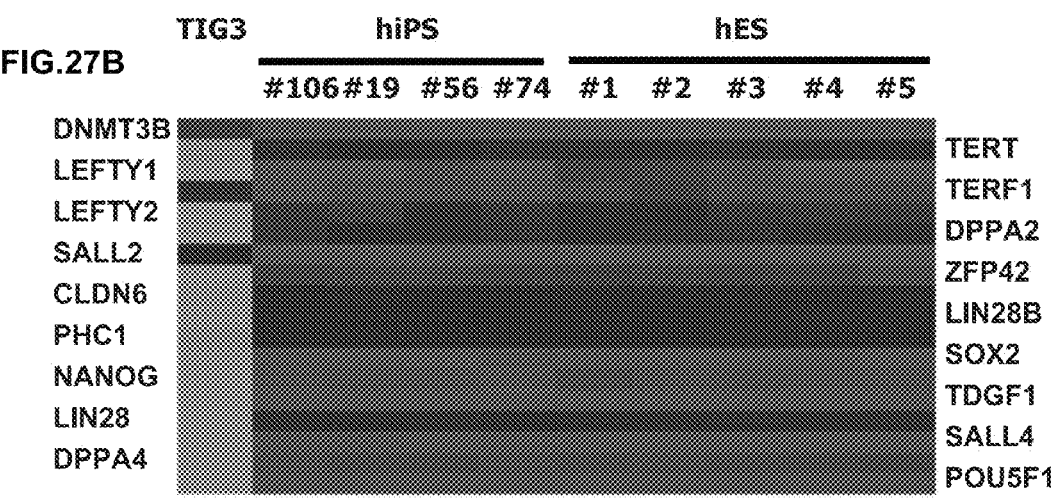
FIG. 27C
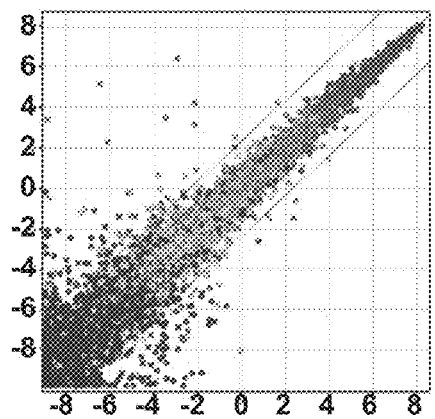

VECTORS FOR GENERATING PLURIPOTENT STEM CELLS AND METHODS OF PRODUCING PLURIPOTENT STEM CELLS USING THE SAME

RELATED APPLICATION

The application claims the benefit of U.S. Provisional patent application No. 61/183,724 filed on Jun. 3, 2009 and the International PCT application PCT/JP2010/058368 filed on May 18, 2010. The teachings of both of these priority documents are hereby incorporated herein by reference in their entirety.

BACKGROUND OF THE INVENTION

1. Field of the Invention

The present invention relates to novel recombinant Sendai virus vector constructs for the reprogramming of differentiated somatic cells into induced pluripotent stem (iPS) cells 2. Description of the Related Art Along with the progression toward an aging society, diseases caused by tissue degeneration and damage are increasing rapidly. For example, diseases that increase in frequency with age include metabolic syndromes, such as cerebral infarction, cardiac infarction and renal failure, as well as diseases caused by age-related tissue degeneration, such as Alzheimer's disease, Parkinson's disease and osteoporosis. In addition, type I diabetes, multiple sclerosis, chronic rheumatoid arthritis, thermal burn, spinal damage from injury, and genetic diseases caused by congenital abnormalities in the genetic code, are all diseases caused by tissue degeneration and damage. A number of regeneration therapies are being developed as a means for treating these diseases.

Regeneration therapies can be tentatively classified into two groups: (1) guided regeneration therapies that target the activation of tissue stem cells residing in a patient's tissue, and (2) cell replacement therapies requiring the transplantation of exo-vivo generated stem cells or stem-cell-derived somatic cells or tissues, into a patient. The regeneration potential of tissue stem cells is however often limited. Development of more effective cell replacement therapies is therefore essential to the practical application of regeneration therapies. In particular, with regard to genetic diseases, cell replacement therapies are contemplated where a patient's cells are genetically engineered ex-vivo to repair or replace defective genes prior to transplantation back into the patient.

Treatment of diseases caused by tissue degeneration/damage, also requires the preparation of large amounts of stem cells or stem cell-induced somatic tissues. Thus, pluripotent stem cells capable of self-renewal over long periods of time while maintaining their differentiation potential into various tissue types are essential requirements for the development of effective cell replacement therapies. To date only a few pluripotent stem cells have been characterized that meet these requirements and include embryo-stem cells (ES cells) derived from the epiblast of early mammalian embryos, and ES cells derived from primordial germ cells. These heterogenic cells cannot be used in cell replacement therapies however because their genetic information is different from that of a patient's hence transplantation of the cells into a patient would inevitably lead to tissue rejection.

Cell replacement therapies therefore require the generation of isogenic pluripotent stem cells that are genetically identical to a somatic cell of a patient in order to avoid immunological rejection after transplantation into a patient. To obtain such cells, the invention contemplates the isolation and modification of a patient's own tissue cells to generate isogenic pluripotent stem cells to be practical and efficient, the procedure ideally will require only minimal surgical intervention to harvest a small sample of tissue cells. For example, the procedure contemplates the collection of easily accessible cells requiring minimal surgical intervention, e.g., skin fibroblast cells, oral mucosal cells or hair follicle epithelial cells. To avoid undue stress and discomfort to the patient, the procedure further contemplates the collection of no more than approximately $10^4$ cells for the generation of isogenic pluripotent stem cells.

It is known from research on human ES cells that extensive culture of pluripotent stem cells over long periods of time inevitably leads to the appearance within the cell population of chromosomal abnormalities, such as chromosomal deletions, amplifications and translocations. If established pluripotent stem cells are heterogeneous with respect to chromosomal stability, they would require continuous selection for cell lines with minimal chromosomal rearrangements which would be time consuming, expensive and inefficient. Thus, the method of generating pluripotent stem cells of the invention should reproducibly select not only for pluripotency but also for chromosomal stability within a selected homogeneous clonal population. One method of determining uniformity within a selected clonal population would be to determine an index comprising a correlation coefficient between respective gene expression patterns of the selected cell lines. Using such a selection criteria, only clones of pluripotent cells approaching a coefficient of 1, preferably equal to or greater than 0.98 would be deemed to be sufficiently stable for use in cell replacement therapies.

After the isolation of stable clonal populations derived from a patient's somatic cells, the pluripotency potential and ability to differentiate into various tissues is then determined.

Pluripotency can be verified by assessing the potential for differentiation in vitro or by determining the degree of differentiation in vivo after transplantation of the candidate pluripotent stem cells into an immunodeficient animal. Another caveat to this approach is the propensity of pluripotent cells to form malignant teratocarcinomas after transplantation. Thus, in view of the need to verify that a candidate pluripotent stem cell line is not only pluripotent but also safe and suitable for use in regeneration therapies, verification based on differentiation within malignant teratocarcinomas is inappropriate (see Nakanishi, Regenerative Medicine, 9, 216-221, 2010)

One way to distinguish between a pluripotent stem cell which is less likely to become a malignant tumor in vivo and thereby safe for human therapy, from a teratocarcinoma which is a malignant tumor with differentiation capability, is to analyze germ-line (germinal) transmission in a laboratory animal such as a mouse i.e., to analyze the transmission of genetic information derived from the pluripotent stem cell to the germ line within a chimeric animal created from pluripotent cells. Using this method, germ-line transmission is only observed with pluripotent stem cells that are less likely to become a malignant tumor after transplantation in vivo and are thereby safe for human therapies. Germ line transmission is not observed with pluripotent cells that form a teratocarcinoma after transplantation. However, this verification obviously cannot be performed in a human.

To establish reproducible protocols for the isolation and selection of pluripotent stem cells which are safe for human therapy trials, it is first necessary to identify appropriate pluripotent stem cells from a laboratory animal using the germ line transmission method. In other words, protocols for establishing therapeutically safe pluripotent stem cells first need to be developed using non-human animals, preferably, the mouse for which reproductive technologies are well established. The procedures required for efficient germ line transmission of pluripotent stem cells in mice can then be extrapolated to human therapeutic applications.

From the above discussion, a method of reproducibly generating human pluripotent stem cells applicable to regeneration therapies needs to meet the following requirements: 1) an established human pluripotent stem cell must be genetically identical to that of a patient's cell; 2) a human pluripotent stem cell must be established from $10^4$ somatic cells or less; 3) established pluripotent stem cells must be clonal and genetically stable; and 4) the germ-line transmission must be verifiable using a chimeric animal derived from pluripotent stem cells and establishing that the pluripotent stem cells contribute to the germ line.

A pluripotent stem cell having genetic information identical to that of a patient, can be generated by introducing a specific combination of pluripotentency-inducing genes into human somatic cells using retroviral vectors. Ectopic expression of these genes results in the generation of a human induced pluripotent stem cell (human iPS cell) closely resembling a human ES cell. For example, the introduction and the expression of Oct3/4, Sox2, Klf4 and c-Myc in human skin fibroblast cells using a retroviral or lentiviral vector results in the transformation of a somatic cell into a human iPS cell (see Takahashi, et al., Cell, 131, 861-872, 2007). Similarly, the introduction and expression of Oct3/4, Sox2, Nanog and LIN28 in human skin-derived fibroblast cells using lentiviral vectors results in the generation of human iPS cells (see Yu, et al., Science, 318, 1917-1920, 2007).

Furthermore, a human iPS cell can also be produced using a modified technique in which one or two of the above four types of genes are substituted by a low-molecular-weight compound. For example, one publication reports that the introduction and expression of two genes, Oct3/4 and Sox2, into normal human skin-derived fibroblast cells cultured in the presence of a histone deacetylase inhibitor results in the transformation of the fibroblast cells into human iPS cells (see Huangfu, et al., Nature Biotechnology, 26, 1269-1275, 2008).

However, in each of the above methods, the genes introduced into a somatic cell are known to be inserted randomly in the iPS cell's host DNA. Genetic information within the iPS cell is therefore different from that of the original skin fibroblast cell. This means that an iPS cell produced by the above techniques fails to meet the requirement that "therapeutically safe pluripotent stem cells have genetic information that is identical to that of a patient's cell."

In terms of ensuring the safety of cell replacement therapy, the above gene insertion protocol causes the following problem. If exogenous genes are inserted into the chromosomes at random, they are likely to abnormally activate genes adjacent to the insertion sites and possibly cause unpredictable side effects, even promote the expression of genes involved in the initiation of tumor. For example, it is known that, if genes are inserted at non-specific positions on chromosomes of a human bone marrow stem cell that is capable of maintaining a self-renewal ability over a long period of time, the expression of tumorigenic genes, that is normally inhibited in these cells, can become transcriptionally active due to the proximal insertion of foreign genes, which can ultimately lead to a high frequency of tumor initiation in these cells (see Hacein-Bey-Abina, et al., Science, 302, 415-419, 2003).

This gene insertion phenomenon further causes the following problem in terms of ensuring the safety of the cell replacement therapy. In an iPS cell produced by inserting foreign genes into chromosomes, although expression of the foreign genes may be inhibited during the period where a cell is kept in an undifferentiated state, the expression of the foreign genes may be induced when the cell has differentiated into a somatic cell, and the resulting cell is likely to become cancerous. For example, it is known that, in an iPS cell-derived transgenic mouse produced by the introduction of Oct3/4, Sox2, Klf4 and c-Myc into a skin-derived normal fibroblast cell using retroviral vectors, cancer develops at high frequencies due to reactivation of the externally introduced c-Myc gene (see Okita, et al., Nature, 448, 313-317, 2007). Further, it is noted that expression of the Klf4 or Oct3/4 gene also has the potential to lead to the initiation of cancer (see Jaenisch and Young, Cell, 132, 562-582, 2008).

With a view to solving the above problems caused by random gene integration into the chromosomal DNA of the host somatic cell, researchers have attempted to introduce plasmid DNA into a somatic cell that is capable of only transient expression of the iPS-inducing genes. For example, one report describes lipofection of Oct3/4, Sox2, Klf4 and c-Myc, into a mouse skin-derived fibroblast cell that results in the transient expression of these genes sufficient to generate an iPS cell but without the concomitant insertion of the foreign genes into chromosomes of the host fibroblast cell (see Okita, et al., Science, 322, 949-953, 2008). However, close analysis of this method shows that the introduced genes were found to be inserted into chromosomes in 75% of the mouse iPS cells generated. Thus, this method does not necessarily prevent insertion of foreign genes into the genome of the iPS cell. Moreover, there is no report thus far indicating that a human iPS cell can be produced using this approach without insertion of foreign iPS-inducing genes into the genome of the host somatic cell.

In other efforts to mitigate the problems caused by gene insertion into the host cell's genome, transient expression of iPS-inducing genes (Oct3/4, Sox2, Klf4 and c-Myc) using adenoviral vectors was shown to transform a somatic cell into an iPS. For example, it has been reported that a mouse iPS cell can be produced by cloning Oct3/4, Sox2, Klf4 and c-Myc into adenoviral vectors and co-transducing the recombinant adenoviral vectors into a mouse liver-derived normal liver cell (see Stadfeld, et al., Science, 322, 945-949, 2008). However, here again, the introduction of adenoviral vectors into the host cell inevitably leads to the random insertion of the vectors into the genome of the host cell at significant frequencies (see Ohbayashi, et al., Proc. Natl. Acad. Sci. USA, 102, 13628-13633, 2005). Thus, this method fails to prevent random insertion of foreign genes into the genome of the iPS cell. Once again, there is no report indicating that a human iPS cell can be produced from a human-derived somatic cell, without insertion of foreign genes into the genome of the host cell.

It has also been reported that, after producing an iPS cell by randomly inserting Oct3/4, Sox2, Klf4 and c-Myc, into chromosomes, the inserted genes can then be excised from the host genome using recombinase (see Kaji, et al., Nature, 458, 771-775, 2009). For example, Cre recombinase has been shown to remove Oct3/4, Sox2, Klf4 and c-Myc genes from the host genome following induction of iPS cells (see Kaji, et al., Nature, 458, 771-775, 2009). However, at least in these reports, promoter regions necessary for inducing expression of the reprogramming genes remained in the host cell's genome. Genetic information of the produced iPS cell is therefore not identical to that of a parent cell, and interference with gene expression in proximity to the insertion site remains possible.

In other reports, the iPS inducing genes were introduced into the host somatic cells using a transposon. After transient expression of the iPS inducing genes, the transposon was removed by expression of transposase that excises the transposon and the covalently linked iPS inducing genes from the host cell's genome. (see Woltjen, et al., Nature, 458, 766-770, 2009). This method is, however, inefficient, because the probability of successful removal is only about 0.001% of the total number of produced iPS cells, and no examples using a human cell were given. According to a report by Woltjen, et al., even after removal of the transposable element by transposase, a residual four bases remain at the integration site. In this case, it cannot be denied that the potential for insertional mutagenesis remains possible. Moreover, the transposase used for removing the transposon is an enzyme having both an excision activity resulting in the removal of the transposon and an integrase activity that directs the insertion of transposons into the genome of the host cell. Thus, at least in theory, transposons excised from a particular insertion site may be re-inserted at a different location in the genome. Therefore, it would be necessary to check each iPS cell clone to verify that re-insertion has not reoccurred at a different location.

Yu, et al., have reported that simultaneous expression of Oct3/4, Sox2, Klf4, c-Myc, Nanog, LIN28 and SV40 T antigen in a human normal fibroblast cell, using an extrachromosomally-replicable circular DNA vector (EBV vector) having a replication origin of Epstem-Barr virus (EBV) and EBNA1 gene, transforms the fibroblast cell into an iPS cell. All foreign DNA in the iPS cell can then be eliminated by removal of the episome (see Yu, et al., Science, 324, 797-801, 2009). As of now, this is the only report describing the generation human iPS cells that are genetically identical to that of the parent somatic cell. However, the iPS cell production efficiency is only in the range of about 0.0003 to 0.0006%. Hence, at least $3 \times 10^5$ cells would be required to establish a single iPS cell. Moreover, EBV DNA is not only episomal but can also be inserted into the host cell's DNA at high frequency (see Hurley, et al., J. Virol, 65, 1245-1254, 1991). Thus, this method is also flawed because it does not prevent integration of foreign genes into the genome of the iPS cell. To verify the absence of integration of any foreign DNA again would require the screening of each iPS clone.

A number of different experimental strategies have been devised to generate a iPS cell having genetic information that is identical to that of the parent somatic cell. In one such attempt, a tissue cell nucleus was introduced into an enucleated oocyte (see Wakayama, et al., Science, 292, 740-743, 2001). In another attempt, a peptide capable of crossing cell membranes was fused to the N terminus of each of Oct3/4, Sox2, Klf4 and c-Myc, and scraped-loaded into somatic host cells (see Zhou, et al., Cell Stem Cell, 4, 381-384, 2009). However, there is currently no report indicating that a human iPS cell could be produced using any of these methods.

Recently, Fusaki, et al., (see Fusaki, et al., Proc. Jpn. Acad. Ser. B85, 348-362, 2009) reported a method designed to direct the expression of Oct3/4, Sox2, Klf4 and c-Myc genes in a human skin-derived fibroblast cell and generate pluripotent stem cells, using as a vector a Sendai virus that does not integrate into the host cell's genome (see Fusaki, et al., Proc. Jpn. Acad. Ser. B85, 348-362, 2009 and PCT/JP 2009/062911). In this report, iPS cells were established at a maximum efficiency rate of 1% by loading four types of reprogramming genes on individual vectors, mixing the vectors together and infecting a cell with the mixed vectors. However, this report makes no mention of the genetic stability and the clonality of the iPS cells. According to a semi-qualitative RT-PCR (Reverse Transcription-Polymerase Chain Reaction) analysis of the gene expression, it is immediately apparent that the established iPS cell lines were not entirely clonal i.e. they did not have identical characteristics with respect to chromosomal stability and gene expression profiles. Moreover, only a human iPS cell line is shown in the examples. The report therefore fails to demonstrate that this technique is broadly applicable to different animal species, and that germ-line transmission can be verified using a chimeric animal model derived from a iPS cell. To date, no method has been described for the generation of human iPS cells that are therapeutically safe for human regeneration therapies. There is therefore an unmet need for therapeutically safe iPS cells that fulfill the following four requirements: 1) the established human pluripotent stem cells have identical genetic information to that of the patient; 2) the human iPS cells can be generated from just $10^4$ cells or less; 3) the established human iPS cells are clonal and genetically stable; and 4) the germ-line transmission can be demonstrated using a chimeric animal derived from a iPS cell.

SUMMARY OF THE INVENTION

The invention discloses methods for establishing an induced pluripotent stem cell (hereinafter referred to as "iPS cell") from a normal human tissue cell at an efficiency rate of 0.01% or more, in such a manner as to have genetic information that is identical to that of a patient's cell and properties similar to those of an ES cell, so as to avoid the possibility of immunological rejection of a transplanted cell and tumorigenic transformation due to integration of foreign genes into the genome of host cell.

This goal can be achieved by using a gene expression system free of activity that could alter the host cell's genome by causing, for example, recombinations, insertions or erroneous DNA repair. The inventors found that a differentiated animal cell can be efficiently reprogrammed by transfecting it with a sustained expression-type Sendai virus containing the human Oct3/4, Sox2, Klf4 and c-Myc reprogramming genes cloned into a Sendai virus (hemagglutinating virus of Japan (HVJ)) vector (JP 4478788B and PCT/JP 2008/057212). The inventors further found that the reprogramming gene-loaded recombinant Sendai viral vector can be introduced into the host cell without the risk of incorporation of the foreign genes into the host cell's genome, and, after reprogramming, the vector can be removed easily and quickly using an siRNA. The induced pluripotent stem cells (iPS cell) generated by this procedure are genetically identical to the parental somatic cell and therefore safe for human therapeutic applications The present invention is specifically described as follows.

(1) A reprogramming gene-loaded Sendai viral vector comprising Sendai virus genes and reprogramming genes, wherein the Sendai virus genes comprise an NP gene, P/C gene, M gene, F gene, HN gene and L gene, wherein each of the M gene, the F gene and the HN gene is from a Sendai virus strain Cl.151-derived gene and wherein at least one of the M gene, the F gene and the HN gene is functionally deleted and the L gene encodes the amino-acid sequence of the L protein in which the amino-acid residue at position 1618 is valine.

(2) In the Sendai viral vector set forth in (1), all of the M gene, the F gene and the HN gene may be functionally deleted.

(3) The Sendai viral vector set forth in (1) or (2) may be a virus particle.

(4) In the Sendai viral vector set forth in any one of (1) to (3), the functional deletion in one or more of the M gene, the F gene and the HN gene may be based on insertion or substitution of a reprogramming gene and/or a marker gene, into or for one or more of the M gene, the F gene and the HN gene.

(5) In the Sendai viral vector set forth in any one of (1) to (4), the reprogramming gene may comprise a combination of Oct3/4, Sox2 and Klf4, or a combination of Oct3/4, Sox2, Klf4 and c-Myc.

(6) There is provided a reprogramming gene-loaded Sendai virus for producing an induced pluripotent stem cell, which comprises the Sendai viral vector set forth in any one of (1) to (5).

(7) The Sendai viral vector may comprise a target sequence for a microRNA. For example, the microRNA may be one that is expressed in induced pluripotent stem cells.

(8) There is also provided a template vector for preparing a reprogramming gene-loaded Sendai virus, which comprises a cloning vector with Sendai virus genes and reprogramming genes, wherein the Sendai virus genes include an NP gene, P/C gene, M gene, F gene, HN gene and L gene, and wherein: each of the M gene, the F gene and the HN gene is a Sendai virus strain Cl.151-derived gene; at least one of the M gene, the F gene and the HN gene is functionally deleted; and the L gene encodes the L protein amino-acid sequence in which the amino-acid residue at position 1618 is valine.

(9) In the template vector set forth in (8), all of the M gene, the F gene and the HN gene may be functionally deleted.

(10) In the template vector set forth in (8) or (9), the functional deletion in one or more of the M gene, the F gene and the HN gene may be based on insertion or substitution of a reprogramming gene and/or a marker gene, into or for one or more of the M gene, the F gene and the HN gene.

(11) In the template vector set forth in any one of (8) to (10), the cloning vector may be a phage vector.

(12) In the template vector set forth in (11), the phage vector may be a λ phage vector.

(13) In the template vector set forth in (8) to (12), the reprogramming gene may comprise a combination of Oct3/4, Sox2 and Klf4, or a combination of Oct3/4, Sox2, Klf4 and c-Myc.

(14) The template vector set forth in (8) to (13) may comprise DNA.

(15) The template vector set forth in (14) has a sequence complementary to a target sequence for an expressed microRNA of a differentiated cell for use in producing an induced pluripotent stem cell.

(16) There is provided a cell, wherein the template vector set forth in (8) to (15) is introduced therein.

(17) In the cell set forth in (16), at least the functionally deleted one of the M gene, the F gene and the HN gene may be introduced thereinto by itself or in combination with an NP gene, a P gene and an L gene.

(18) In the cell set forth in (17), T7 RNA polymerase may be expressed therein.

(19) There is provided a method for producing a reprogramming gene-loaded Sendai virus, which comprises: cultivating the cell as defined in any one of (16) to (18), in culture medium, to form therein a Sendai virus particle which comprises, as its genome, Sendai virus genes and reprogramming genes, wherein the Sendai virus genes include NP gene, P/C gene, M gene, F gene, HN gene and L gene, and wherein: each of the M gene, the F gene and the HN gene is a Sendai virus strain Cl.151-derived gene; at least one of the M gene, the F gene and the HN gene is functionally deleted; and the L gene encodes for an amino-acid sequence of an L protein in which the 1618-th amino-acid residue is valine.

(20) There is provided a method of producing an induced pluripotent stem cell, which comprises: infecting a differentiated cell with the reprogramming gene-loaded Sendai virus set forth in (6) to reprogram the differentiated cell; and then allowing siRNA to act on the vector so as to remove the reprogramming gene-loaded Sendai viral vector from the cell.

(21) In the method set forth in (20), the siRNA may have a sequence for targeting an L protein of a Sendai virus.

(22) There is provided siRNA, which comprises a sequence for targeting an L protein of a Sendai virus.

(23) There is provided a reagent for removing a reprogramming gene-loaded Sendai viral vector after reprogramming a differentiated cell, which comprises the siRNA set forth in (22).

(24) There is provided a method of producing an induced pluripotent stem cell, which comprises: infecting a differentiated cell with the reprogramming gene-loaded Sendai virus set forth in (7) to reprogram the differentiated cell; and then removing the reprogramming gene-loaded Sendai viral vector, after forming an induced pluripotent stem cell, wherein the differentiated cell is a microRNA-expressing cell.

(25) There is provided a method of producing an induced pluripotent stem cell, which comprises: infecting a differentiated cell with the reprogramming gene-loaded Sendai virus set forth in (6) or (7) to reprogram the differentiated cell; and then culturing the cell under high-temperature conditions to promote removal of the reprogramming gene-loaded Sendai viral vector from the cell.

As above, in the Sendai viral vector of the present invention, a plurality of reprogramming genes can be cloned into a single common vector, and expressed simultaneously in the same cell, the reprogramming of a differentiated cell is significantly facilitated. In addition, the reprogramming gene-loaded Sendai viral vector of the present invention can express reprogramming genes while being present in the cytoplasm in a sustained and stable manner, which makes it possible to eliminate the risk of foreign genes being inserted into the host cell's genome, and thus ensures a significantly higher level of safety and a reduced risk of inducing cancer. Furthermore, based on the use of the vector of the present invention, an induced pluripotent stem cell (hereinafter referred to as "iPS cell") that is genetically identical to that of a patient's cell and pluripotency similar to that of an ES cell can be established at a pluripotent stem cell-establishment efficiency rate of from at least 0.01% to over 1%, even from a human normal cell and even if the number of the cells is equal to or less than $10^4$. In addition, the established induced pluripotent stem cells are significantly uniform in cellular properties such as genetic stability and clonality, as evidenced by the fact that the correlation coefficient between the respective gene expression patterns of the cells is 0.98 or more, so that it becomes possible to avoid tumorigenic transformation, which would occur due to prolonged culture of induced pluripotent stem cells. As for the pluripotent stem cell obtained using the Sendai viral vector of the present invention, germline transmission has been confirmed in the mouse. Thus, the pluripotent stem cell is less likely to become a malignant tumor and hence it is safe to use in human therapies. In view of the above points, the pluripotent stem cell is expected to be effective for human therapies.

After inducing expression of the reprogramming gene in the cell cytoplasm, the reprogramming gene-loaded Sendai viral vector can be easily removed from the cell using siRNA that targets a preselected sequence that is incorporated into the Sendai virus genome. This makes it possible to obtain an iPS cell that is genetically identical to that of the differentiated parent cell and that is safe for human therapeutic use. In other instances, the vector can be removed by means of culture at high-temperatures.

Moreover, the wide host cell specificity/cellular specificity of the Sendai virus means that iPS cells can be established from a wide variety of human tissue cells other than fibroblast cells (i.e. blood cells). This makes it possible to confirm the function of the iPS cells using a nonhuman animal.

Compared with adenoviral vectors, EBV vectors, conventional Sendai viral vectors as well as other more conventional DNA vectors, for generating iPS cells, the present invention permits the generation of iPS cells in a simple and efficient manner with excellent reproducibility, while drastically enhancing the safety of the produced iPS cell. This should contribute greatly to the implementation of iPS technology to a wide range of therapeutic applications, such as regeneration therapies (particularly, cell replacement therapy and gene therapy) as well as promote research on the development of new drugs using patient-derived iPS cell having various genetic backgrounds. The availability of genetically defined human pluripotent stem cells also promises to facilitate research on various stem cell-related diseases, for example, the etiology of cancer stem cells and their role in metastasis

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 3A (at day 4) and 3B (at day 10) are photographs showing the result of removal of a sustained expression-type Sendai viral vector from a cell by use of siRNA.

FIG. 8 depicts electrophoresis photographs showing a genome PCR-based gene-type analysis result of a mouse iPS marker-expressing cell prepared using a sustained expression-type Sendai viral vector (FIG. 8A: D18Mit4; FIG. 8B: D7Mit4; FIG. 8C: D4Mir15). Lane 1: C57/BL mouse derived fibroblast cell. Lane 2: C57/BL mouse-derived colony #1. Lane 3: C57/BL mouse-derived colony #2. Lane 4: 129 mouse derived ES cell.

FIG. 13 depicts a photograph showing expression of SSEA-4 antigen in a human embryonic fibroblast cell on the 25th day after infection with the hOct4/hSox2/hKlf4/hc-Myc sustained expression-inducing Sendai viral vector. Green: human pluripotent stem cell-specific antigen SSEA-4. FIG. 13A: phase contrast microscopic observation. FIG. 13B: Fluorescent microscopic observation.

FIG. 16 depicts a series of photographs showing respective emergence efficiencies of a human iPS marker (i.e., alkaline phosphatase)-expressing cell colony, under normal culture conditions (37° C., 5% $CO_2$) and under high-temperature culture conditions (40° C., 2% $CO_2$). The cells infected with Sendai viral vector and with the retroviral vector were stained for alkaline phosphatase, respectively, on the 10th and 20th day after infection. Red: alkaline phosphatase, an iPS cell marker. FIG. 16A: hOct4/hSox2/hKlf4/hc-Myc sustained-expression inducing Sendai vector; FIG. 16B: hOct4/hSox2/hKlf4/hc-Myc sustained-expression inducing Sendai vector Version 2; FIG. 16C: hOct4/hSox2/hKlf4/hc-Myc sustained-expression inducing retroviral vector FIG. 17A shows the detection of Sendai virus NP antigen; FIG. 17B shows the detection of SSEA-4, an iPS/ES cell marker; FIG. 17C shows DAPI staining (detection of DNA).

FIG. 22 is a graph obtained by quantitatively measuring a temporal change in removal of a sustained expression-type Sendai viral vector from a cell, using siRNA. FIG. 22A shows the selective removal of KO/Hyg/EGFP/Luc2CP-loaded sustained expression-type Sendai viral vector using siRNA. FIG. 22B shows hygromycin resistance in cells after removal of KO/Hyg/EGFP/Luc2CP-loaded sustained expression-type Sendai viral vector, using siRNA (right) and before removal of the vector (left).

FIG. 23 depicts a photograph and a graph showing a comparison between the gene expression patterns of recombinant exogenous genes cloned into a single common sustained expression-type Sendai viral vector versus where each exogenous gene is cloned into an individual sustained expression-type Sendai viral vector. FIG. 23A shows a fluorescent microscopic observation of $LLCMK_2$ (SeVdp/KO/HygB/EGFP/Luc2CP) cells (Left) and $LLCMK_2$ (SeVdp/Zeo/KO/CLuc+SEVdp/Bsr/EGFP/91phox) cells (Right). FIG. 23B shows FACSalibur analysis of $LLCMK_2$ (SeVdp/KO/HygB/EGFP/Luc2CP) cells (Left) and $LLCMK_2$ (SeVdp/Zeo/KO/CLuc+SeVdp/Bsr/EGFP/gp91phox) cells (Right). FIG. 23C shows data obtained by reanalyzing results of the FACSalibur analysis of $LLCMK_2$ (SeVdp/KO/HygB/EGFP/Luc2CP) cells (Left) and $LLCMK_2$ (SEVdp/Zeo/KO/CLuc+SeVdp/Bsr/EGFP/gp91phox) cells (Right) in terms of ratio between KO and EGFP.

FIG. 25 depicts photographs showing the establishment of a human iPS marker-expressing cell using the hOct4/hSox2/hKlf4/hc-Myc sustained expression-inducing Sendai viral vector Version 3. FIG. 25A: Detection of Sendai virus-NP antigen; FIG. 25B: Detection of SSEA-4 antigen, an iPS/ES cell marker. On the 24th day after infection with the vector (the cells were subcultured twice during this period), the vector was removed without any treatment with siRNA, etc and NP antigen becomes undetectable.

FIG. 26 depicts a photograph of a human iPS marker-expressing cell established from adult human peripheral blood mononuclear cells using a hOct4/hSox2/hKlf4/hc-Myc sustained expression-inducing Sendai viral vector. FIG. 26A: phase contrast microscope image; FIG. 26B: alkaline phosphatase stain image FIG. 27 depicts a diagram showing a comparison between gene expression patterns of a plurality of types of human iPS marker-expressing cells established using a hOct4/hSox2/hKlf4/hc-Myc sustained expression-inducing Sendai viral vector. FIG. 27A shows the correlation coefficients of four human iPS marker-expressing cell lines established using hOct4/hSox2/hKlf4/hc-Myc sustained expression-inducing Sendai viral vector. FIG. 27B shows a comparison of human ES marker gene expression between four human iPS marker-expressing cell lines established using hOct4/hSox2/hKlf4/hc-Myc sustained expression-inducing Sendai viral vector, and five human ES cell lines. Stronger reddish color indicates higher intensity of expression. FIG. 27C shows the correlation of gene expression between human iPS marker-expressing cells established using the hOct4/hSox2/hKlf4/hc-Myc sustained expression-inducing Sendai viral vector (#56 cell line, X-axis) and human ES cells (Kyoto Univ. #4 cell line, Y-axis).

DESCRIPTION OF THE EXEMPLARY EMBODIMENTS

Figure 1:
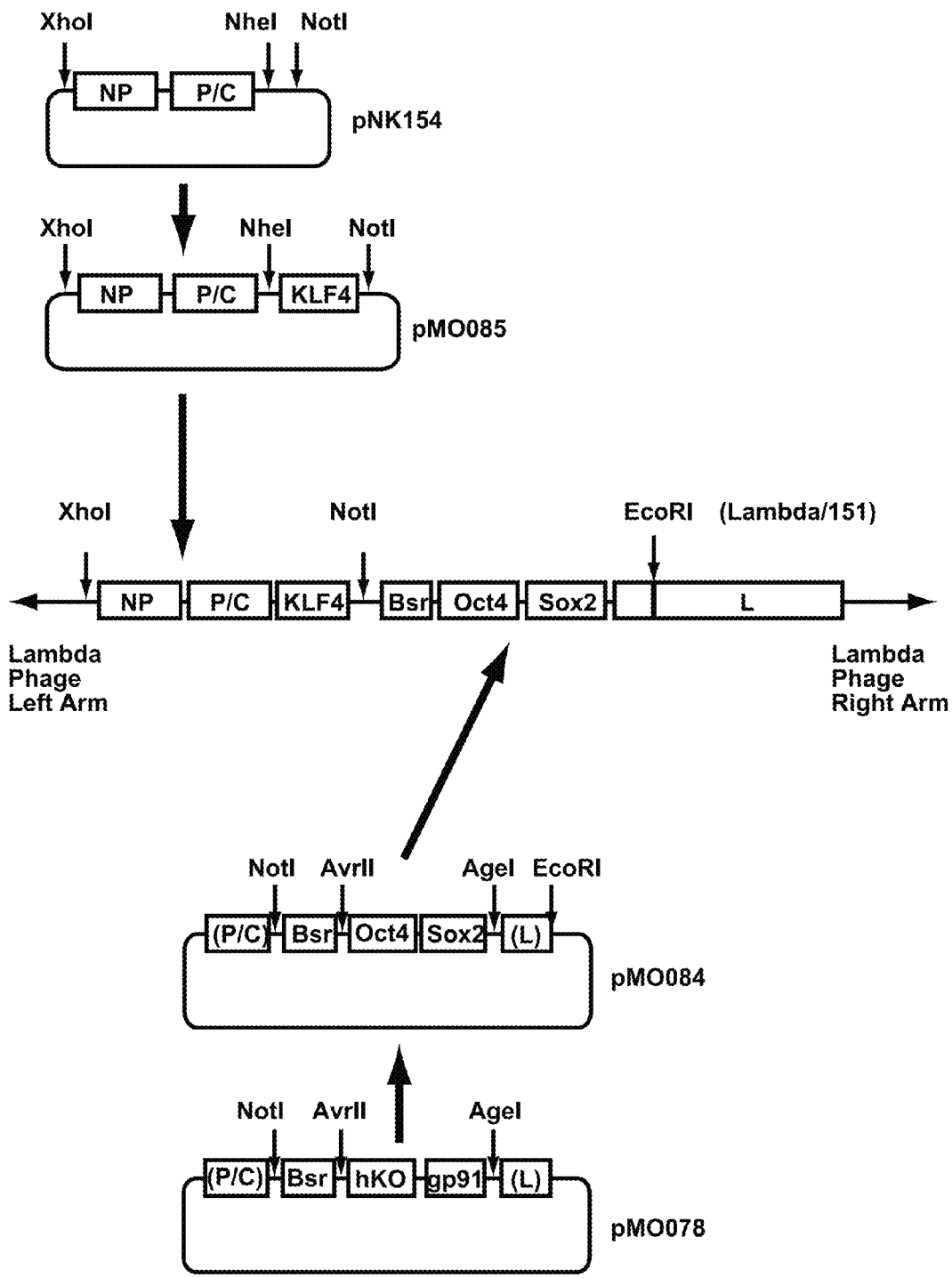
FIG. 1 is a diagram of the preparation of a template cDNA for producing a hOct4/hSox2/hKlf4 sustained expression-inducing Sendai viral vector.

A vector loaded with a reprogramming gene for use in producing an induced pluripotent stem cell in the present invention is a Sendai virus particle which has an NP gene, a P/C gene and an L gene each derived from a Sendai virus, and at least one of F, M and HN genes of the Sendai virus is functionally deleted (this vector will hereinafter be referred to as "Sendai viral vector"). As used in this specification, the term "gene" or "gene material" encompasses negative-strand RNA or cDNA and positive-strand RNA or cDNA complementary thereto. In other words, any vector capable of synthesizing either one of such genes or gene materials by means of transcription or reverse transcription should be construed as being included in the present invention.

As used herein, the term "functionally deleted" means a gene is rendered non-functional by deletion of the complete gene sequence or a portion thereof sufficient to abolish the activity of the gene by, for example, inhibiting the expression of the gene through deletion of key regulatory sequences or by deletion of parts of the gene's coding region or by the disruption of the gene's open reading frame.

As used in this specification, the term "induced pluripotent stem cell (iPS cell)" means a cell which expresses a morphology similar to an embryonic stem cell (ES cell), and an embryonic stem cell-specific marker, and has a self-renewal ability in vitro. iPS cells also have the potential to differentiate into any of the three germ layers in vivo and in vitro. For example, Nanog, Oct4, alkaline phosphatase, SSEA-1 and SSEA-4 antigens are well known markers of embryonic stem cells and can be readily detected in iPS cells.

[Constituent Materials of Sendai Viral Vector]

The Sendai viral vector is a recombinant transfection/expression vector in which a gene of a Sendai virus can be replaced with any exogenous gene thus enabling the expression of the exogeous gene in any transfected cell. Sendai viruses have an NP gene, a P/C gene, an F gene, an M gene, an HN gene and an L gene, which are required for the transcription and replication of the Sendai virus. The F, M and HN genes also have a role in formation of a virus particle. Recombinant Sendai viral vectors lacking the F, M and HN genes are therefore incapable of forming new virus particles and hence further propagation after transfection into a cell.

The Sendai viral vector of the present invention comprises an L gene which encodes an L protein where the 1618-th amino acid is replaced by a valine. This mutation was found in the amino-acid sequence of an L protein derived from the Sendai virus strain Cl.151, which exhibits temperature-sensitive growth, where almost no virus particle is produced at 38° C., but at 32° C., the replication cycle becomes active and permits the production of virus particles. Sendai virus strain Cl.151 was first reported by Tetsuya Yoshida, PhD, in 1979 (Yoshida, et al., (1979), Virology, 92, 139-154).

Sendai virus strains Cl.151 have L proteins harboring a mutated amino acid residue at position 1618 together with a reduced ability to induce interferon activity in transfected cells. This strain can therefore sustain infectious ability without cytotoxicity, so that, when a foreign gene is incorporated into the Sendai virus genome, expression of the gene will be maintained in the cell for a long period of time. For example, the leucine residue at position 1618 of the L gene of the Sendai virus strain Nagoya, can be mutated to a valine. As described herein, an L protein where the 1618-th residue is valine will be referred to as a "mutated-L protein", and the gene, which encodes the mutated-L protein will be referred to as "mutated-L gene."

Thus, the NP, C/P and L genes as constituent genes of the Sendai viral vector of the present invention may have a base sequence derived from wild-type cytopathic Sendai virus strains, such as a Sendai virus strain Nagoya or Z, as long as the L gene has the above mutation.

A transcriptional termination sequence of a Sendai virus may be artificially inserted into the 3'-terminal end of the genomic RNA. The copy number of anti-genomic RNAs can then be further reduced to lower the interferon-inducing ability within the transfected cell.

As a prerequisite to Sendai virus infection of an animal cell, it is essential that the Sendai virus have the mutated-L gene, in addition to F, M and HN genes derived from the Sendai virus strain Cl.151. Thus, the Sendai viral vector having the mutated-L gene and the Sendai virus strain Cl.151-derived F, M and HN genes together can have a sustained infectious ability without cytotoxicity, so that, when a foreign gene is inserted into the Sendai virus vector, the expression of the gene will be maintained in the cell over a long period of time. In Sendai viral vectors based on the strain Cl.151, one or more (including "all") of the strain Cl.151-derived F, M and HN genes may be functionally deleted, without interfering with the ability of the recombinant vector to drive the expression of the exogenous gene. In this case, even if only one of the three genes is functionally deleted, the transmissibility of the vector can be significantly suppressed. In view of fully suppressing transmissibility, it is preferable to functionally delete all of the F, M and HN genes. The functional deletion of one or more of the F, M and HN genes may be based on simple deletion of a part or all of the three genes, or insertion or replacement with an exogenous gene of interest.

A full-length cDNA of the Sendai virus strain Cl.151 has already been registered in the GenBank (Accession Number AB275416).

[Reprogramming Gene]

A reprogramming gene is inserted into the Sendai viral vector of the present invention. Reprogramming genes may include the combination of mammalian Oct3/4, Sox2 and Klf4 genes together with a mammalian (e.g human or mouse) c-Myc gene and, one or more of Nanog, LIN28, Esrrb, UTFI and TERT (telomerase catalytic subunit), or a gene encoding large T antigen of SV40.

[Template Vector for Preparing Reprogramming Gene-Loaded Sendai Viral Vector]

In the present invention, the NP, P/C and mutated-L genes as constituent materials of the Sendai viral vector are inserted into a cloning vector, such as phage, together with the reprogramming genes. In this process, all of the reprogramming genes can be inserted into the cloning vector together. This allows for the generation of reprogramming gene-loaded Sendai viral vector that contains all the genes required for reprogramming. Reprogramming is therefore efficiently performed without the need for introducing each reprogramming gene into a different vector.

The recombinant vector obtained in the above manner can then serve as a template for preparing reprogramming gene-loaded Sendai virus of the present invention, i.e., a Sendai virus particle carrying all the required reprogramming genes. This recombinant vector will hereinafter be referred to as "template vector".

The template vector is prepared by incorporating the NP, P/C and mutated-L genes, and the reprogramming genes into a vector such as phage, in the following order: NP→P/C→reprogramming genes (a marker gene may further be introduced therein as described later)→mutated L.

The reprogramming genes or the marker gene may be used to functionally delete at least one of the F, M and HN genes of the Sendai viral vector, by replacement of at least one of the F, M and HN genes with the reprogramming genes or marker gene.

A marker gene, such as a drug-resistance gene, can be inserted into the template vector. This makes it possible to facilitate screening of a target cell containing the template vector or the Sendai viral vector.

More specifically, the template vector is prepared by combining the constituent materials of the Sendai viral vector comprising the above genes, the reprogramming gene cDNAs, and the marker gene cDNA, together in the above order, to form a (+) strand genomic RNA. For example, the constituent material cDNA is incorporated into a cloning vector, such as λ DASH II. A T7 promoter sequence and three guanidine residues are then cloned into the upstream side of the incorporated full-length cDNA (i.e. at the 3'-terminal end of the genomic RNA), and a hairpin ribozyme sequence of a tobacco ringspot virus and a termination sequence of T7 RNA polymerase are then inserted on the downstream side of the full-length cDNA (i.e. at the 5'-terminal end of the genomic RNA).

The T7 promoter sequence is added to allow a (+) strand genome RNA to be synthesized from the 3'-terminal end of the genomic RNA by T7 RNA polymerase, and three guanidine residues are added to enhance the efficiency of RNA transcription by the T7 RNA polymerase (S. Leyrer, et al., (1998) J. Virol. Methods, 75; 47-58). The hairpin ribozyme sequence of the tobacco ringspot virus is added to allow the transcript (+) strand genome RNA to be accurately cut at one end, and the termination sequence of T7 RNA polymerase is added to allow the RNA transcription by the T7 RNA polymerase to terminate at a discrete location.

[Preparation of Reprogramming Gene-Loaded Sendai Viral Vector]

The template vector harboring the reprogramming genes can then be introduced into a viral vector-producing cell in order to prepare a reprogramming gene-loaded Sendai virus.

In order to transcribe (+) strand anti-genomic RNA from the template vector in a virus-producing cell, it is necessary to supply exogenous T7 RNA polymerase. For example, the viral vector-producing cell line can be infected with T7 RNA polymerase-expression vaccinia virus, or may be a cell strain in which T7 RNA polymerase is constitutively expressed.

The cell strain (BHK/T7 cell) is just such a cell line because it expresses a humanized T7 RNA polymerase gene that permits significantly higher levels of T7 RNA polymerase gene expression as compared with a cell strain (BSR-T7-5 cell) that expresses a conventional bacterial T7 RNA polymerase gene. As a result of production of recombinant viruses using the BHK/T7 cell line, large amounts of recombinant viruses can be efficiently generated and collected.

The presence of T7 RNA polymerase within the viral vector-producing cell drives transcription of the template vector from the T7 promoter sequence. Downstream sequences are then cleaved off by the hairpin ribozyme sequence, so that a (+) strand anti-genomic RNA molecule is generated corresponding to a DNA portion including the NP gene, the P/C gene, the reprogramming genes and the mutated-L gene in the template vector that may further include a marker gene as needed.

An expression vector for producing NP, P and L gene products may be additionally introduced into the viral vector-producing cell having the (+) strand anti-genomic RNA transcribed from the template vector by the T7 RNA polymerase. In this case, the NP, P and L gene products are bound to the (+) strand anti-genomic RNA to form an RNP complex (nucleocapsid). Then, using the RNP complex as a template, a (−) strand genomic RNA is transcribed from the (+) strand anti-genomic RNA by the RNA polymerase in the viral vector-producing cell. The (−) strand genome RNA is bound to NP, P and mutated-L gene products in the viral vector-producing cell to form a RNP complex including the (−) strand genomic RNA.

In the template vector used in the above manner, one or more of the strain Cl.151-derived M, F and HN genes are functionally deleted thereby suppressing the ability to form infectious virus particles. To propagate virus, the missing gene products are transfected into the viral vector-producing cell comprising the RNP complex (nucleocapsid) with the (−) strand genomic RNA. The transfected cell is then incubated at the permissive temperature of 32° C.

Consequently, the RNP complex (nucleocapsid) including the (−) strand genome RNA is incorporated into viral vector particles to generate reprogramming gene-loaded Sendai virus. As described above, in the present invention, an expression vector containing the missing gene either the F, M and HN genes, is separately introduced into the viral vector-producing cell to form virus particles. This makes it possible to harvest the virus particle from a culture supernatant of the viral vector-producing cell. In cases where two or more of the F, M and HN genes are absent, the expression vector may contain one or more of the missing genes or alternatively each of the missing genes can be cloned into a single expression vector that is then co-transfected into the viral vector-producing cell.

In the above virus-particle production process, virus production can be further enhanced by introducing supplemental expression vectors for an NP gene, a P/C gene and an L gene.

In addition, a drug-resistance gene may be inserted into the target viral vector-producing cell as discussed above. In this case, it becomes possible to select viral vector-producing cells through incubation in culture medium containing the appropriate drug. Alternatively, a target viral vector-producing cell may be isolated using a marker gene, such as the EGFP gene.

The reprogramming gene-loaded Sendai virus obtained in the above manner is in the form of a virus particle that is capable of infecting a differentiated cell. However, as one or more of the F, M and HN genes of the vector are functionally deleted, the formation of a viral vector from the infected cells is suppressed. In addition, the L gene of the vector is mutated such that the leucine at position 1618 of the encoded L protein is replaced with valine. This modification inhibits the induction of interferon in the transfected cells, and permits the sustained expression of the reprogramming genes within the infected cells.

[Reprogramming of Differentiated Cell]

The recombinant Sendai virus particle containing the reprogramming genes is then used to infect a differentiated cell derived from a normal human or a patient with a disease of interest. Differentiated cells may be, for example, fibroblast cells, oral mucosal cells, blood cells, hair follicle epithelial cells, or cells obtained by surgical intervention or tissue biopsies, such as liver cells, large intestinal mucosa cells, small intestinal mucosa cells and lung epithelial cells. Differentiated cells are not limited to human cells, but include differentiated cells of an animal, such as mouse, rat, hamster, guinea pig, rabbit, dog, cat, monkey, bovine, pig, sheep, goat or chicken, which are permissive to Sendai virus infection. Sendai viruses can infect a wide variety of animal cells, equine-derived cells and B-lymphocytes of various animal species are rare exceptions that Sendai virus cannot infect. This feature is a significant advantage over other viral vector systems that exhibit a narrow host range, such as a retroviral vector, a lentiviral vector or an adenoviral vector; or other gene expression systems usable only in human cells, such as an EBV vector; or even plasmid expression vectors, transposon and EBV vectors that have to be introduced into the cells using a physical delivery system. For example, although the adenoviral vector can be used to reprogram a mature mouse liver cell, the reprogramming efficiency rate is only 0.0005% at best. Moreover, adenoviral vectors are incapable of reprogramming a mouse or human fibroblast cell.

On the contrary, the reprogramming gene-loaded Sendai viral vector of the present invention can reprogram a mouse fibroblast cell (see Example 5), a human blood mononuclear cell (see Example 18), as well as a human fibroblast cell. In addition, a chimeric mouse derived from a mouse iPS cell produced using the reprogramming gene-loaded Sendai viral vector of the present invention contributes to the germ-line. Cell lines produced by the present invention are therefore more likely to be normal pluripotent stem cells that are therapeutically safe (see Example 10).

In the reprogramming gene-loaded Sendai viral vector of the present invention, an L gene is mutated to inhibit interferon induction, and M, F and HN genes in a wild-type Sendai virus are functionally deleted. Thus, the vector exhibits a sustained infectious ability without cytotoxicity, and, after infection of a differentiated cell, it persists in the cytoplasm of the infected cell. Even after cell division, this state is maintained. This feature is not observed in other types of Sendai viral vectors without a mutated-L gene or with at least one of the M, F and HN genes of the wild-type Sendai virus. Thus, the use of the Sendai viral vector of the present invention makes it possible to maintain expression of the reprogramming genes for 10 to 20 days, which is required for the completion of the reprogramming process. Reprogramming can therefore be completed using a single gene delivery. This advantage is not available with adenoviral vectors or plasmid vectors that are only capable of inducing transient gene expression. For example, in cases where Oct3/4, Sox2, Klf4 and c-Myc are loaded on the reprogramming gene-loaded Sendai viral vector of the present invention, even if a cell is infected with the vector only once, the cell can maintain expression of the exogenous reprogramming genes, and expression of endogenous reprogramming genes as well as alkaline phosphatase, a marker of an embryo-stem cell (ES cell), starts to be detectable after 7 to 14 days post-transfection.

Once inside the cell, Sendai viral vectors of the present invention remain episomal and do not insert themselves into the host genome unlike other vector systems. Thus, iPS cells generated with modified Sendai virus of the invention are significantly safer for human therapeutic applications because the lack of genomic integration minimizes the risk of oncogene activation within the host genome. In this regard, the Sendai viral vector of the present invention is significantly superior to other systems, such as retroviral vectors, lentiviral vectors, adenoviral vectors, transposon vectors and plasmid vectors in general (such as the EBV vector) all of which have the propensity to integrate into the host genome. The possibility of integration and the subsequent uncontrolled long-term expression of some reprogramming genes such as c-Myc, Oct4 or LIN28 is particularly undesirable because the long term expression of these genes is known to induce cancer or pre-cancerous states such as cell dysplasia.

As noted above, strategies for the reprogramming of somatic cells must also favor genomic stability and reproducibly generate clonal cell populations having identical properties. Ideally, the viral vector should be capable of accepting multiple reprogramming genes permitting the simultaneous transfer of all genes into the same cell while at the same time directing the expression of all the genes in unison. Reprogramming genes may be transferred into a somatic cell by infection with viral particles containing a single common Sendai viral vector having all the reprogramming genes in cis, as shown in the Examples of the present invention. Alternatively each reprogramming gene can be cloned into its own Sendai virus vector. Viral particles, each containing a viral vector comprising at least one reprogramming gene are then mixed together prior to infection of the somatic cells, as disclosed in Fusaki, et al., Proc. Jpn. Acad. Ser. B85, 348-362, 2009 and PCT/JP 2009/062911. To determine if there is a difference in gene expression between genes cloned in cis on a single viral vector and the same genes cloned on individual viral vectors, the Enhanced Green Fluorescent Protein (EGFP) gene and the Kusabira-Orange (KO) gene were cloned into a single common vector or into individual viral vectors. The results show that optimal gene expression is obtained when the reprogramming genes are present on a single common vector (see Example 15). Moreover, the simultaneous transfer of the reprogramming genes on a single vector into a somatic cell also promotes iPS cell generation with enhanced efficiency (see Example 16).

In the reprogramming gene-loaded Sendai viral vector of the present invention, all of the reprogramming genes are loaded on a single common vector, so that, when the vector of the present invention is used, emergence efficiency of an iPS cell (reprogramming efficiency) is extremely high. For example, in cases where Oct3/4, Sox2, Klf4 and c-Myc are loaded thereon, the efficiency rate increases up to 16.8% (see Examples 5 and 8). In contrast, a reprogramming efficiency rate in a mature mouse liver cell using adenoviral vectors is only 0.0005% or less. Even with EBV vectors, the reprogramming efficiency rate is only in the range of about 0.0003 to 0.0006%.

The presence of all reprogramming genes on a single common vector ensures their coordinated expression which results in the generation of iPS cells with significantly more uniform properties. For example, in an analysis of iPS cells established using the procedures described herein, gene expression of the iPS candidates was analyzed by a DNA chip method and the correlation coefficient between four different cell lines was determined to be 0.98 or more (see Example 19). This contrasts with the fact that the gene expression pattern in pluripotent stem cells established using a retroviral vector is generally non-uniform, and the correlation coefficient between cell lines is 0.95 or less in many cases (Reference: Chin, et al., Cell Stem Cells, 5, 111-123, 2009).

As above, it became evident that, based on the use of the reprogramming gene-loaded Sendai viral vector of the present invention where four types of reprogramming genes are cloned into a single common vector, pluripotent stem cells having uniform properties can be established with significantly high efficiency while constantly ensuring excellent reproducibility.

[Removal of Reprogramming Genes]

The reprogramming gene-loaded Sendai virus of the present invention infects a differentiated cell, and the reprogramming genes are expressed sustainably in the cytoplasm of the cell to reprogram it. In order to make the genetic information of the reprogrammed cell identical to that of the original or pre-programming cell, the reprogramming genes need to be removed from the cell. In the present invention, the entire reprogramming gene-loaded Sendai viral vector is removed using a siRNA. The siRNA is designed to target the L gene of the Sendai viral vector. According to experimental results by the inventors, the reprogramming gene-loaded Sendai viral vector can be completely removed by targeting the L gene, although the reprogramming gene-loaded Sendai viral vector can also be removed to some extent by targeting the NP gene or the P gene. For example, a target region of the L gene can be the segment allocated between 527-th or 1913-th nucleotide of the L protein gene. The target region may be any other suitable region. The siRNA is introduced into the cell 5 to 20 days after the reprogramming gene-loaded Sendai virus infected the differentiated cell.

Instead of siRNA, microRNA (miRNA) may be used to remove the viral vector from the cell. miRNA is a small RNA transcribed from the genome of an animal cell, and capable of interacting with a transcript to adjust the function thereof. In an interaction with mRNA, there exists a mechanism where the miRNA binds to a target sequence on the mRNA to induce decomposition of the mRNA or suppress translation of the mRNA. Target sequences for a specific miRNA can be artificially inserted into a protein-noncoding region of a mRNA. Expression of the miRNA then inhibits the expression of the gene. Thus, the reprogramming gene-loaded Sendai viral vector can be removed in the same manner as that used in the siRNA approach by adding a target sequence for miRNA to an L, NP or P gene-noncoding region of the Sendai viral vector. Expression of miRNA in the cell then suppresses expression of the L, NP or P gene. The miRNA to be used for the above purpose may include, but is not limited to, mir-302a that is specifically expressed, for example, in human or mouse ES cells. For example, the technique of removing the reprogramming gene-loaded Sendai viral vector using miRNA has the advantage of being able to automatically remove the Sendai viral vector without the need for externally introducing siRNA because the mir-302a is expressed as soon as a differentiated cells is reprogrammed into an iPS cell. Further, in a human cell, the removal of the vector can also be promoted by means of culture at a high temperature (40° C.).

The reprogramming gene-loaded Sendai viral vector can therefore be removed using either a siRNA that targets the L gene, by culture at a high-non-permissive temperature, or by introducing a target sequence for miRNA into the non-coding regions of the L, NP or P gene-in the Sendai virus vector.

Consequently, the induced iPS cell is genetically identical to that of the parental differentiated cell used to generate the iPS stem cell. By the end of the procedure the cell does not contain any foreign exogenous DNA and its potential for self renewal is enhanced, Various examples of the present invention are described below. It is understood that the present invention is not limited to the following examples.

EXAMPLES

Example 1

Preparation of Cells for Constructing Sustained Expression-Type Sendai Viral Vectors A cDNA (SEQ ID NO: 1 in the following Sequence Table) encoding T7 RNA polymerase where codons are optimized to improve expression in an animal cell, was cloned into a plasmid pCX4SRalpha-neo vector for preparing a retroviral vector. A cDNA encoding Sendai virus strain Cl.151 M protein was first cloned into a plasmid pCX4SRalpha-puro vector for preparing a retroviral vector. The plasmid DNAs were then introduced into respective PLAT-E packaging cells using Lipofectamine 2000, and retroviruses (T7 RNA polymerase recombinant retrovirus and 151M recombinant retrovirus) obtained from a culture supernatant. The T7 RNA polymerase recombinant retrovirus was transfected into BHK-21 cells. The infected BHK-21 cells were then transferred to a Dulbecco's Modified Minimal Essential Medium (DMEM) containing 800 µg/ml of G418 and 10% of fetal bovine serum (FCS), and G418-resistant cells (BHK/T7 (SE)) which stably express T7 RNA polymerase were isolated. Subsequently, the 151M recombinant retrovirus was transfected into BHK/T7 (SE) cells and the infected BHK/T7 (SE) cells were transferred to a DMEM containing 800 µg/ml of G418, 15 µg/ml of puromycin and 10% of FCS. G418+puromycin-resistant cells (BHK/T7/151M (SE)) which stably express T7 RNA polymerase and an M protein were isolated.

Example 2

Preparation of hOct4/hSox2/hKlf4 Sustained Expression-Inducing Sendai Viral Vector (1) Construction of Template cDNA for Preparing Recombinant Sendai virus A double-stranded DNA (SEQ ID NO: 2 in the Sequence Table) including Avr II recognition sequence, human Oct4 ORF, Sendai virus (SeV) genome cDNA (bases 6617 to 6666), human Sox2 ORF and Age I recognition sequence in this order was synthesized, and then cloned into the plasmid vector pUC57 (the cloning was achieved using GenScript Inc.) (pUC57-OctSox). A DNA sequence cut from the pUC57-OctSox at Avr II and Age I sites was inserted between Arv II and Age I sites of a plasmid vector pMO078 (SEQ ID NO: 3 in the Sequence Table) where Cla I recognition sequence, SeV strain Cl.151 genome cDNA (bases 2871 to 3650), Not I recognition sequence, a blasticidin S-resistance gene, Mlu I recognition sequence, SeV strain Cl.151 genome cDNA (bases 4728 to 4828), Avr II recognition sequence, humanized Kusabira-Orange gene, an SeV strain Cl.151 genome cDNA (bases 6617 to 6666), gp91phox gene, Age I recognition sequence and SeV strain Cl.151 genome cDNA (bases 8442 to 10479) were inserted into a plasmid pBluescript II SK(+) (Agilent Technologies Inc.)) in this order. In this manner, a plasmid pMO084 was constructed (FIG. 1).

A double-stranded DNA (SEQ ID NO: 4 in the Sequence Table) including Nhe I recognition sequence, human Klf4 ORF, Sendai virus transcription termination sequence, Sendai virus transcription initiation sequence and Not I recognition sequence in this order was synthesized, and then cloned in a plasmid vector pUC57 (the cloning was achieved using GenScript Inc.) (pUC57-KLF4). A DNA sequence cut from the pUC57-KLF4 at Nhe I and Not I sites was inserted between Nhe I and Not I sites of a plasmid vector pNK154 (SEQ ID NO: 5 in the Sequence Table) where SeV strain Nagoya genome cDNA (bases 1 to 2871), SeV strain Cl.151 genome cDNA (bases 2872 to 3656), Nhe I recognition sequence and Not I recognition sequence are inserted into pBluescript II SK(+) (Agilent Technologies Inc.)) in this order. In this manner, a plasmid pMO085 was obtained (FIG. 1).

A DNA fragment (including a T7 promoter sequence, a SeV genome cDNA (bases 1 to 3655) and a human Klf4 cDNA) cut from the pMO085 at restriction endonucleases Xho I and Not I, a DNA fragment (including human Oct4 and human Sox2 cDNAs) cut from the pMO084 at restriction endonucleases Not I and EcoR I, and a DNA fragment (including a cDNA complementary to bases 10480 to 15384 in the SeV genome, and a right arm in a λ DASH II) cut from a phage genome DNA of λ/151 (lambda phage vector cloned with a full-length SeV strain Cl.151 genome cDNA: Nishimura, et al., J. Biol. Chem., 282, 27383-27391, 2007) at EcoR I site, were then combined together, and cloned into a lambda phage vector λDASH II to prepare λ/SeVp (Mp+ Klf4, ΔM:: Bsr, ΔF:: Oct4, ΔHN:: Sox2) (FIG. 1) (a cDNA complementary to a full-length genome of a hOct4/hSox2/ hKlf4 sustained expression-inducing Sendai viral vector described as SEQ ID NO: 6 in the Sequence Table).

(2) Preparation of hOct4/hSox2/hKlf4 Sustained Expression-Inducing Sendai Virus

BHK/T7/151M (SE) cells were seeded on a 6-well plate at a density of 5×10⁵ cells/well, and washed after cultivation for 24 hours. A λ/SeVp (Mp+Klf4, ΔM:: Bsr, ΔF:: Oct4, ΔHN:: Sox2) phage DNA, an NP protein-expression plasmid pGEM/NP, a P protein-expression plasmid pGEM/P, an L protein-expression plasmid pGEM/L, an F protein-expression plasmid pSRD-FZmut and an HN protein-expression plasmid pMKIT-NaHN were suspended in 300 µL of Opti-MEM, respectively, at quantitative ratios of 2 µg, 1 µg, 1 µg, 1 µg, 1 µg and 1 µg, and the obtained suspension was mixed with 300 µL of Opti-MEM containing 10 µL of Lipofectamine 2000. After leaving the mixture at room temperatures for 20 minutes, it was added to the cells, and the cells were cultured for 4 hours. Then, the cells were washed, and after adding DMEM containing 10% of FCS, further cultured at 32° C. for 3 days. Then, the cells were transferred to DMEM containing 10% of FCS and 10 µg of blasticidin S.

Blastcidin-resistant cells were then isolated as hOct4/hSox2/hKlf4 sustained expression-inducing Sendai viral vector-producing cells (BHK/T7/151M/KBOS). The occurrence of reconstruction of a vector genome was confirmed by a fluorescent antibody method using antibody to Sendai virus NP protein and antibodies to hOct4/hSox2/hKlf4 gene products.

2 µg each of pMKIT-151M, pSRD-ZFmut and pMKIT/NaHN as defective gene-expression plasmids were introduced into $5.0 \times 10^5$ BHK/T7/151M/KBOS cells using Lipofectamine 2000. After 4 hours, the cells were washed, and, after adding DMEM containing 10% of FCS thereto, further cultured at 32° C. for 4 days. Culture supernatant containing a hOct4/hSox2/hKlf4 sustained expression-inducing Sendai virus was then harvested. The culture supernatant was filtered through a 0.45 µm filter, and ultracentrifuged as needed to concentrate the vector. The vector suspension was quickly frozen using liquid nitrogen, and cryopreserved at −80° C.

Example 3

Figure 2:
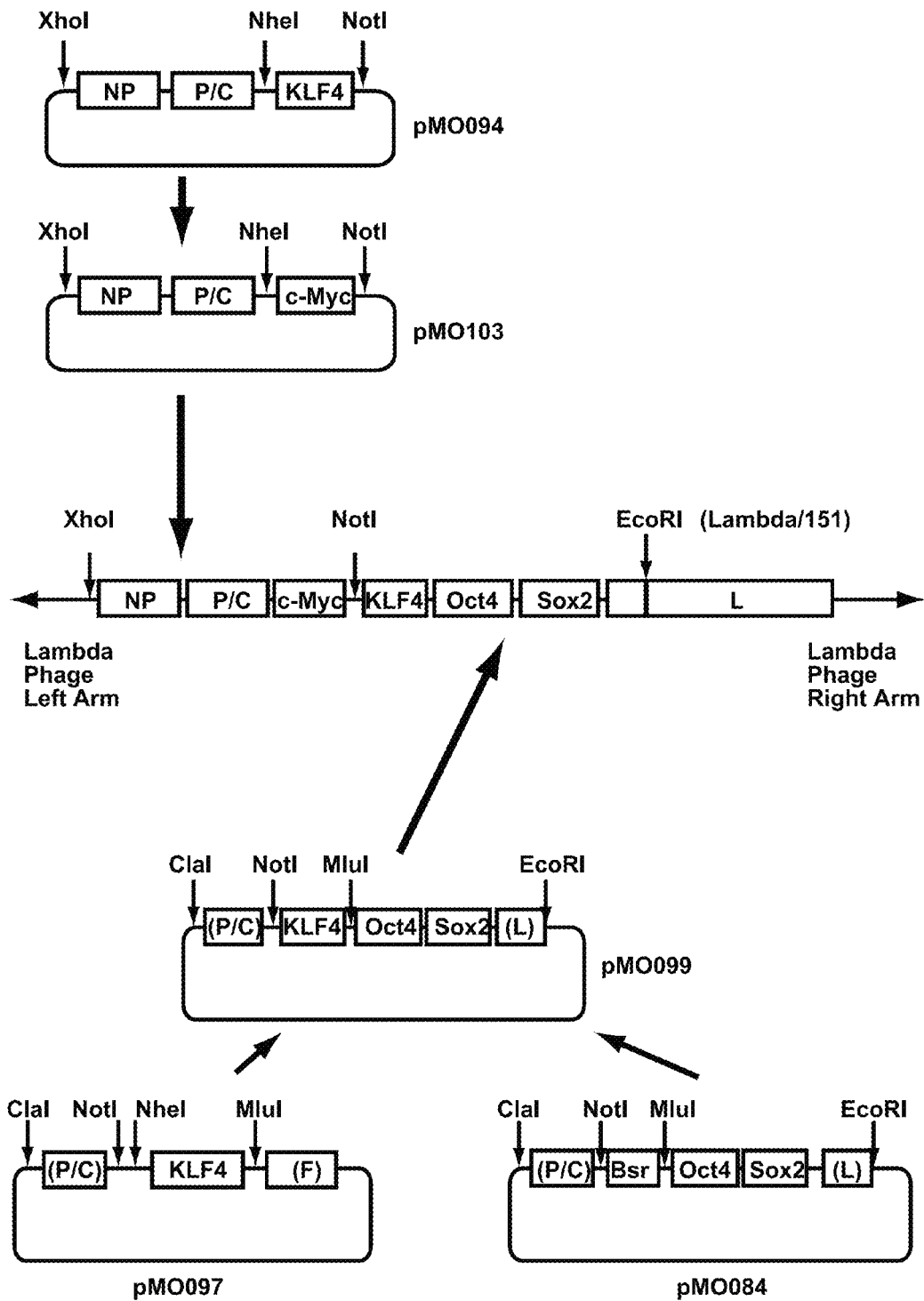
FIG. 2 is a diagram of the preparation of a template cDNA for producing a hOct4/hSox2/hKlf4/hc-Myc sustained expression-inducing Sendai viral vector.

Preparation of hOct4/hSox2/hKlf4/hc-Myc Sustained Expression-Inducing Sendai Viral Vector (1) Preparation of Vector cDNA A human Klf4 gene was amplified from the pUC57-KLF4 by a PCR method using two primers consisting of 5'-ACTAGCTAGCAGTCTGACATGGCTGTCAGCGACGCGCT-3' (SEQ ID NO: 7 in the Sequence Table (N-terminal side)) and 5'-GGTCCACGCGTTTAAAAA TGCCTCTTCATGTG-3' (SEQ ID NO: 8 in the Sequence Table (C-terminal side)) as hKlf4 gene-amplifying primers. The termini of the obtained double-stranded DNA were cut at Nhe I and Mlu I sites, and inserted between Nhe I and Mlu I sites of pMO026 (SEQ ID NO: 9 in the Sequence Table) (a plasmid vector where Cla I recognition sequence, SeV strain Cl.151 genome cDNA (bases 2871 to 3650), Not I recognition sequence, Nhe I recognition sequence, blasticidin S-resistance gene, Mlu I recognition sequence and SeV strain Cl.151 genome cDNA (bases 4728 to 5335) were inserted into pBluescript II SK(+)). In this manner, pMO097 was obtained. Furthermore, a fragment between Cla I and Mlu I sites of the pMO097 was combined with a fragment between Cla I and Mlu I sites of the pMO084 to obtain pMO099 (FIG. 2).

A human c-Myc gene was amplified from a plasmid pJL1 including a full-length human c-Myc cDNA by a PCR method using two primers consisting of 5'-ACTAGCTAGCTTAGA CGCTGGATTTTTTTCGGGTAGTGG-3' (SEQ ID NO: 10 in the Sequence Table (N-terminal side)) and 5'-GTCCGACGTCCTTACGCACAAGAGTTCCGT-3' (SEQ ID NO: 11 in the Sequence Table (C-terminal side)) as hc-Myc gene-amplifying primers. The termini of the double-stranded DNA were cut at Nhe I and Aat II sites, and inserted between Nhe I and Aat II sites of pMO094 (SEQ ID NO: 12 in the Sequence Table) (a plasmid vector where an SeV strain Nagoya genome cDNA (bases 1 to 43), Sendai virus transcription termination sequence, SeV strain Nagoya genome cDNA (bases 56 to 2870), SeV strain Cl.151 genome cDNA (bases 2871 to 3656), Nhe I recognition sequence, human Klf4 ORF, Aat II recognition sequence, Sendai virus transcription termination sequence, Sendai virus transcription initiation sequence and Not I recognition sequence were inserted into pBluescript II SK(+) (Agilent Technologies Inc.)). In this manner, pMO103 was obtained (FIG. 2).

Based on the plasmids obtained as described above, the T7 promoter sequence and DNA fragment SeV (1 to 3655 with c-Myc), and DNA fragment SeV (3655 to 10480 with KLF4/Oct4/Sox2), were cut out from pMO103 and pMO099, respectively, and combined with a DNA fragment of SeV (10480 to 15384)+the right arm of the λ DASH II obtained by cutting the λ/151 at the EcoR I site. Then, the combination was cloned to prepare λ/SeVp (Mp+myc, ΔM:: Klf4, ΔF:: Oct4, ΔHN:: Sox2) (FIG. 2) (a cDNA complementary to a full-length genome of a hc-Myc/hOct4/hSox2/hKlf4 sustained expression-inducing Sendai viral vector is described as SEQ ID NO: 13 in the Sequence Table).

(2) Preparation of hOct4/hSox2/hKlf4/hc-Myc Sustained Expression-Inducing Sendai Virus The BHK/T7/151M (SE) cells were seeded on a 6-well plate at a density of $5 \times 10^5$ cells/well, and, after culture for 24 hours, the cells were washed. A λ/SeVp (Mp+myc, ΔM:: Klf4, ΔF:: Oct4, ΔHN:: Sox2) phage DNA, an NP protein-expression plasmid pGEM/NP, a P protein-expression plasmid pGEM/P, an L protein-expression plasmid pGEM/L, an F protein-expression plasmid pSRD-FZmut and an HN protein-expression plasmid pMKIT-NaHN were suspended in 300 µL of Opti-MEM, respectively, at quantitative ratios of 2 µg, 1 µg, 1 µg, 1 µg, 1 µg and 1 µg, and the obtained suspension was mixed with 300 µL of Opti-MEM containing 10 µL of Lipofectamine 2000. After leaving the culture medium at room temperatures for 20 minutes, the culture medium was added to the cells, and the cells were cultured for 4 hours. The cells were washed and, after adding DMEM containing 10% of FCS, further cultured at 32° C. for 3 days and 37° C. for another 3 days. Cells were then stained using the fluorescent antibody method (see Example 20) using antibody directed to Sendai virus NP protein and antibodies to the hOct4/hSox2/hKlf4 gene products, to confirm the reconstruction of the vector genome in the cells. The cell population was used as hOct4/hSox2/hKlf4/hc-Myc sustained expression-inducing Sendai virus producing cells without further cloning.

2 µg each of pMKIT-151M, pSRD-ZFmut and pMKIT/NaHN as defective gene-expression plasmids were introduced into $5.0 \times 10^5$ hOct4/hSox2/hKlf4/hc-Myc sustained expression-inducing Sendai virus-producing cells using Lipofectamine 2000. After 4 hours, the cells were washed, and, after adding DMEM containing 10% of FCS, further cultured at 32° C. for 4 to 9 days. The culture supernatant containing hOct4/hSox2/hKlf4/hc-Myc sustained expression-inducing Sendai virus was then harvested, filtered through a 0.45 µm filter and ultracentrifuged, to concentrate the vector, as needed. The virus suspension was frozen using liquid nitrogen, and cryopreserved at −80° C.

Example 4

Removal of the Sustained Expression-Type Sendai Viral Vector from Cells Using siRNA In order to remove the vector sequences from the cells stably transduced with the sustained expression-type Sendai viral vector, two types of short interfering RNAs (siRNAs) were designed to suppress expression of the L gene encoding a subunit of RNA-dependent RNA polymerase that is necessary for sustained infection of the vector (#1: sense strand 5'-GGUUCAGCAUCAAAUAUGAAG-3' (SEQ ID NO: 14 in the Sequence Table), antisense strand 5'-UCAUAUUUGAUGCUGAACCAU-3' (SEQ ID NO: 15 in the Sequence Table), #2: sense strand 5'-GGUCCAGACAUGAAUUCAAAG-3' (SEQ ID NO: 16 in the Sequence Table), antisense strand 5'-UUGAAUUCAUGUCUGGAC-CAU-3' (SEQ ID NO: 17 in the Sequence Table)). In order to check for removal of the viral vector by the siRNA, BHK/T7 cells stably transduced with the sustained expression-type Sendai viral vector containing an aequorea victoria-derived EGFP gene (enhanced green fluorescent protein: Clontech Laboratories Inc.) were seeded onto a 48-well plate at a density of $1.0\times10^4$ cells/well. The next day, the siRNA targeting the L gene was added to the cells to a final concentration of 100 nM. After 4 days post transfection, EGFP fluorescence was examined by fluorescence microscopy. The intensity of EGFP fluorescence in the cell having the L gene specific siRNA was greatly reduced, as compared to cells exposed to a negative control siRNA that targets a firefly luciferase gene (FIG. 3A). Moreover, some of the cells treated with the siRNA were re-seeded on a 12-well plate, and cultured for another 6 days. As a result of the L gene-specific siRNA activity, no EGFP fluorescence was detected in most all of the cells. This shows that the reduction in intensity of EGFP fluorescence is not caused by temporary suppression of gene expression, but by removal of the vector sequences from the cells (FIG. 3B).

Example 5

Induction of the Cells Expressing Mouse iPS Marker from Mouse Embryo-Derived Fibroblast Cells (1) Preparation of Mouse Embryo-Derived Fibroblast Cells An embryo was removed from a mouse (C57BL/6J or Nanog-EGFP (Enhanced Green Fluorescent Protein) knock-in mouse (STOCK Tg (Nanog-GFP, Puro) 1Yam) at the 14th day of pregnancy. After removing the head, four limbs and internal organs, the remaining body parts were chopped up, and treated with trypLE Express (Invitrogen Corp.) at 37° C. for 30 minutes. After a brief spin to dispose of non-cellular components, the cells in the supernatant were cultured in Dulbecco's Modified Minimal Essential Medium (DMEM) containing 10% of fetal bovine serum (FCS) to obtain mouse embryo-derived fibroblast cells (MEFs).

(2) Induction of the Cells Expressing Mouse iPS Markers

The MEFs were cultured in a 12-well plate at a density of $1.0\times10^5$ cells/well. The next day, each of the hOct4/hSox2/hKlf4 sustained expression-inducing Sendai virus prepared in Example 2, the hOct4/hSox2/hKlf4/hc-Myc sustained expression-inducing Sendai virus prepared in Example 3 and the hOct4/hSox2/hKlf4/hc-Myc sustained expression-inducing Sendai virus Version 2, described in Example 12 were added to the culture medium to infect the MEFs at room temperature, and then the infected MEFs were cultured at 37° C. overnight.

Mitomycin-treated MEFs were plated on a gelatin-coated dish. After attachment, the vector-infected cells were seeded on top of the quiescent feeder layer. The cells were then cultured in mouse ES medium (DMEM, 15% FCS, 0.1 mM nonessential amino acids, 0.55 mM 2-ME, 1000 U/ml Leukemia Inhibitory Factor (LIF)) or KSR medium (Knockout DMEM, 15% Knockout Serum Replacement (KSR), 2 mM Glutamine, 0.1 mM nonessential amino acids, 0.05 mM 2-ME, 1000 U/ml Leukemia Inhibitory Factor (LIF)).

Figure 4:
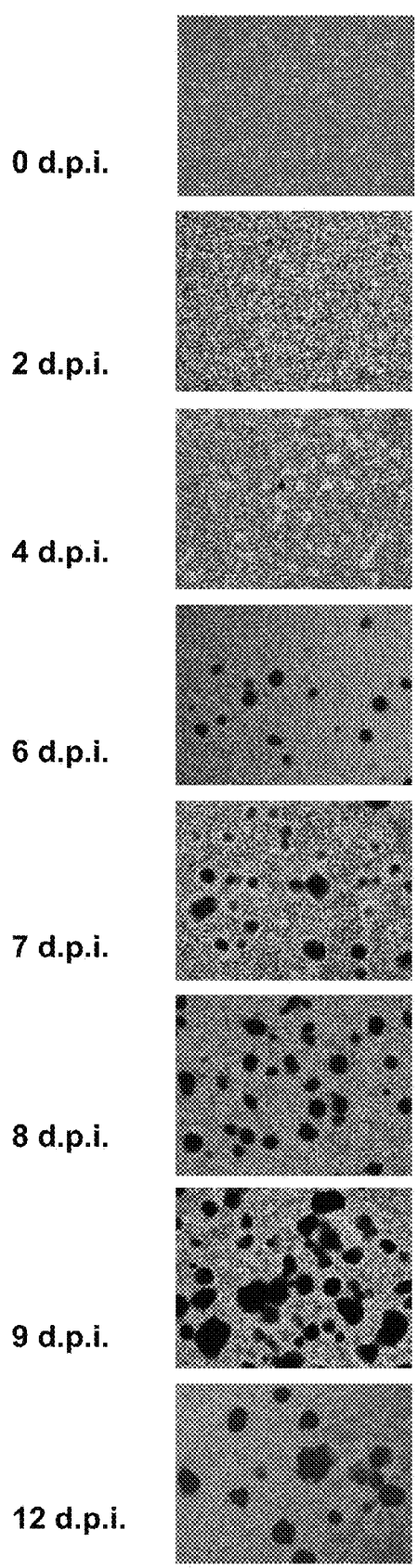
FIG. 4 is a series of time-lapse phase photographs using a phase contrast microscope (from 0 to 12 days post infection) showing the expression of alkaline phosphatase in a mouse embryonic fibroblast cell infected with the hOct4/hSox2/hKlf4/hc-Myc sustained expression-inducing Sendai viral vector.
Figure 5:
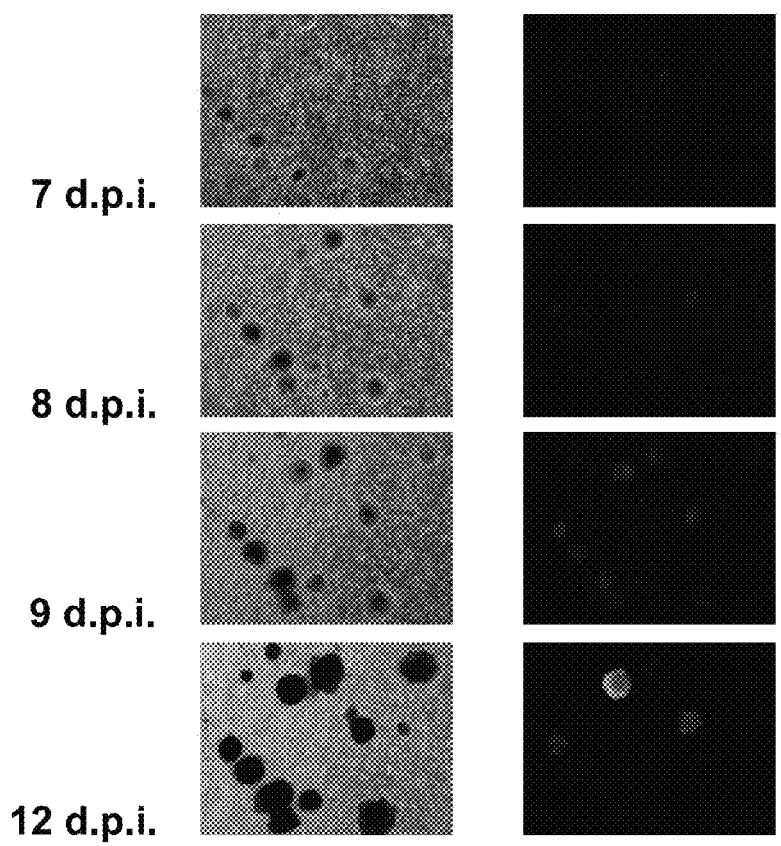
FIG. 5 is a series of time-lapse photographs using a phase contrast and fluorescent microscope (from 7 to 12 days post infection) showing expression of EGFP in a Nanog-EGFP knock-in mouse embryonic fibroblast cell infected with the hOct4/hSox2/hKlf4/hc-Myc sustained expression-inducing Sendai viral vector. Red: alkaline phosphatase. Green: nanog-GFP. D.p.i.: days post infection. Left side: Phase contrast microscopic observation. Right side: Fluorescent microscopic observation.
Figure 6A:
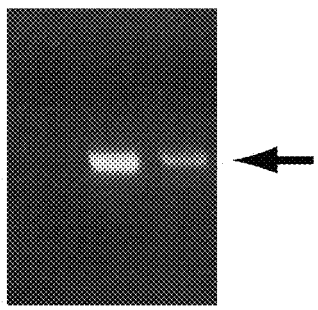
FIG. 6 depicts an RT-PCR analysis showing the expression (indicated by the arrows) of the Sendai virus NP gene (FIG. 6A), endogenous mouse Oct4 gene (FIG. 6B) and endogenous mouse Nanog gene (FIG. 6C) in a mouse embryonic fibroblast cell on the 14th day after infection with the hOct4/hSox2/hKlf4/hc-Myc sustained expression-inducing Sendai viral vector. Lane 1: non-infection with vector (negative control). Lane 2: $14^{th}$ day post infection with vector. Lane 3: $40^{th}$ day post infection with vector.
Figure 6B:
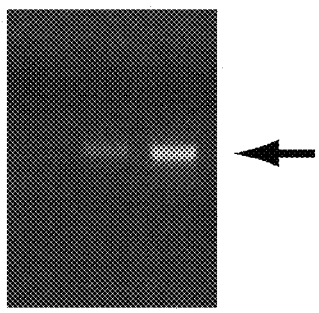
Figure 6C:
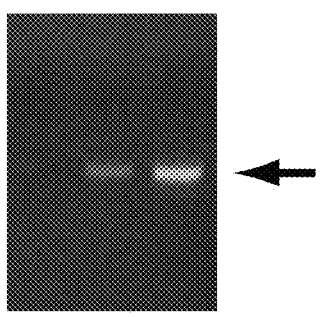
Figure 7:
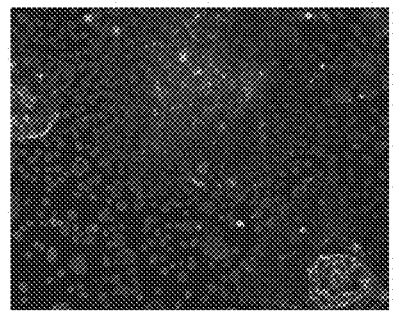
FIG. 7 is a photograph showing expression of SSEA-1 antigen in a mouse embryonic fibroblast cell on the 14th day after infection with the hOct4/hSox2/hKlf4/hc-Myc sustained expression-inducing Sendai viral vector using a fluorescent antibody method. Green: mouse pluripotent cell-specific antigen SSEA-1. Blue: DNA (DAPI staining).

6 days after infection with the hOct4/hSox2/hKlf4/hc-Myc sustained expression-inducing Sendai virus, ES-like cell colonies formed that stained positive for alkaline phosphatase activity (FIG. 4). In those MEFS derived from Nanog-EGFP knock-in mice, GFP-positive colonies were detected 8 days post-infection indicating induction of expression from the endogenous Nanog gene (FIG. 5). RT-PCR analysis further showed that (see Example 20 (c)), mouse Nanog (FIG. 6C) and Oct4 (FIG. 6B) (markers of a mouse iPS cell) are induced in cells forming iPS colonies (FIG. 6). Using the fluorescent antibody method (see Example 20 (a)), mouse SSEA-1 was detected in cells within the iPS colonies (FIG. 7). Genotyping (see Example 20 (d)) demonstrated that the genetic make-up of the induced mouse iPS marker-expressing cell is identical to that of the parent MEFs but different from that of a mouse ES cell used as a positive control. Hence, these results demonstrate that mouse iPS marker-expressing cells were generated by introducing hOct4, hSox2, hKlf4, hc-Myc into MEFs (FIG. 8). Substantially the same result was obtained with hOct4/hSox2/hKlf4/hc-Myc sustained expression-inducing Sendai viral vector Version 2.

(3) Test for Induction Efficiency of Mouse iPS Marker-Expressing Cells

The proportion of cells infected with the sustained expression-type Sendai virus was quantitatively measured using a fluorescent antibody method against the NP (see Example 20 (a)), and the number of alkaline phosphatase activity-positive colonies (see Example 20 (b)) was corrected for infection efficiency to calculate the induction efficiency of mouse iPS marker-expressing cells. The results are shown in Table 1.

TABLE 1

Temporal observation of the emergence frequency of alkaline phosphatase - expressing cell in mouse embryo fibroblast cells infected with hOct4, hSox2, hKlf4, and hc-Myc sustained expression-inducing Sendai virus

| Time (days) after infection | Frequency with respect to all cells (%) | Frequency with respect to infected cells (%) |
|---|---|---|
| 6 | 5.3 | 9.1 |
| 7 | 8.6 | 14.9 |
| 9 | 13.1 | 22.5 |
| 12 | 7.1 | 12.3 |

As seen in the results of Table 1, it became evident that the cells expressing mouse iPS marker can be induced with significantly higher efficiency than previous iPS reports in which four genes consisting of hOct4, hSox2, hKlf4 and hc-Myc were introduced into differentiated cells using a retroviral vector or by using other vector systems. Substantially the same result was obtained with the hOct4/hSox2/hKlf4/hc-Myc sustained expression-inducing Sendai viral vector Version 2.

Example 6

Figure 9:
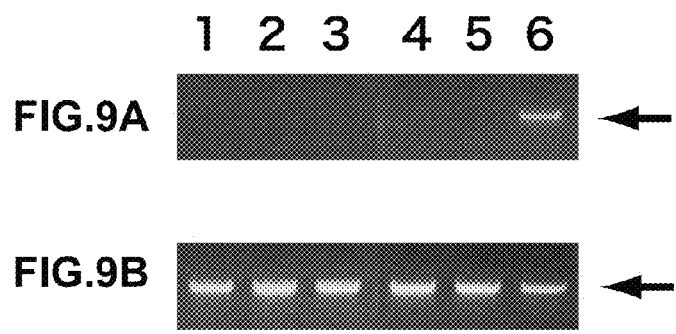
FIG. 9 depicts an electrophoresis photograph showing expression (indicated by the arrows) of Sendai virus NP gene (FIG. 9A) and endogenous mouse Nanog gene (FIG. 9B) in a mouse iPS marker-expressing cell after removal of a sustained expression-inducing Sendai viral vector using an siRNA. Lane 1: mouse iPS cell MEF/MKOS #3. Lane 2: mouse iPS cell MEF/MKOS #4. Lane 3: mouse iPS cell MEF/MKOS #6. Lane 4: mouse iPS cell MEF/MKOS #21. Lane 5: mouse iPS cell MEF/MKOS #1. Lane 6: cell before removal of vector.

Production of Mouse iPS Cells by Removal of the RNA Genome of Sustained Expression-Type Sendai Viral Vector Sequences In order to remove the vector RNA from the cells expressing the mouse iPS markers obtained in Example 5, the siRNA targeting the L gene was introduced into the cells as described in Example 4. At the first and subsequent cell passages, the siRNA was introduced as a mixture with lipofectamin 2000 into the culture medium. After about one week, fluorescent antibody staining (see Example 20 (a)) confirmed that no vector RNA remained in any of the colonies as judged by the inability of the antibody assay to detect Sendai virus NP protein, as described in Example 5. Furthermore, a colony was cloned, and checked by RT-PCR (see Example 20 (c)) for the absence of any NP gene-derived messenger RNA (mRNA). The reprogramming procedure of the invention therefore produced a mouse iPS cell clone devoid of any vector sequences (see FIG. 9A). Moreover, RT-PCR analysis (see Example 20 (c)), confirmed the expression of mouse Nanog and Oct4 gene in the iPS stem cell colonies. The expression of these iPS cell markers was maintained even after the removal of all of the Sendai virus vector sequences (FIG. 9B).

Example 7

Figure 10:
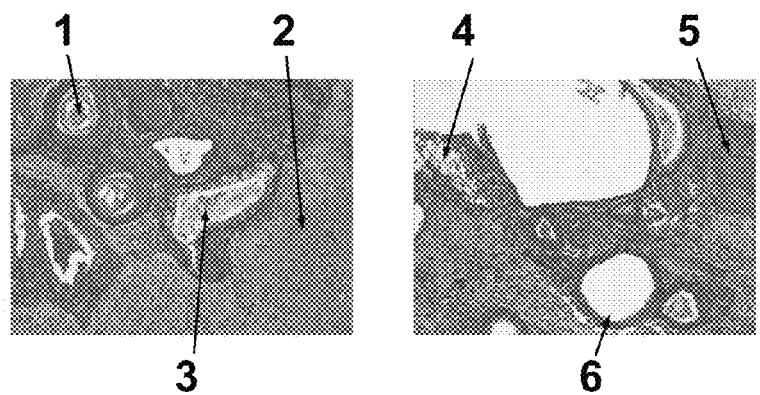
FIG. 10 depicts photographs showing HE stained histological sections of teratoma derived from a mouse iPS marker-expressing cell after removal of a sustained expression-inducing Sendai viral vector by use of siRNA. 1: Skin (derived from ectoderm); 2: Nerve (derived from ectoderm); 3: Digestive tract (derived from endoderm); 4: Adipocyte (derived from mesoderm); 5: Muscle (derived from mesoderm); 6: Thyroid grand (derived from endoderm).

Formation of Teratomas after Transplantation of Mouse iPS Cells into Immunocompromised Mice The iPS cells obtained in Example 6 were adjusted to a concentration of $1.0 \times 10^6$ cells/100 µL PBS, and transplanted under a skin at the root of a leg of a mouse (C. B17/Icr-scidJcl) sedated using isoflurane anesthesia. 2 weeks after the inoculation, a visually identifiable teratoma formed. 30 days after the implantation, the teratoma was excised and fixed in Bouin's fixative solution (75% of saturated picric acid, 12% of formalin, 3% of acetic acid), and dehydrated by treatment with 70% ethanol solution (1 hour), 90% ethanol solution (1 hour), 100% ethanol solution (1 hour, twice), 50% ethanol solution, 50% 2-butanol solution (1 hour) and 100% 2-butanol solution (30 minutes, twice). Samples were then fixed in paraffin, and subjected to HE staining. As can be seen in FIG. 10, the teratomas contained tissues resulting from the differentiation of iPS cells into tissues of all three germ layers.

Example 8

Induction of Cells Expressing Human iPS Marker from Human Embryo-Derived Fibroblast Cells (1) Induction of Human iPS Marker-Expressing Cells TIG3 cells, i.e. human embryo-derived fibroblast cells, were cultured in a 12-well plate at a density of $10 \times 10^5$ cells/well. After one day, each of the hOct4/hSox2/hKlf4/hc-Myc sustained expression-inducing Sendai virus (prepared in Example 3) and the hOct4/hSox2/hKlf4/hc-Myc sustained expression-inducing Sendai virus Version 2 (prepared in Example 12) were added to the culture medium, and left at room temperature for 2 hours. The cells were then cultured in the presence of the recombinant Sendai viruses overnight at 37° C. The virus-infected cells were then plated on a feeder layer of mitomycin-treated MEFs and cultured in hES medium (DMEM/F12, 20% of Knockout Serum Replacement (KSR), 0.1 mM nonessential amino acids, 0.55 mM 2-ME, 10 ng/ml bFGF) or a primate ES cell culture medium (ReproCELL).

Figure 11:
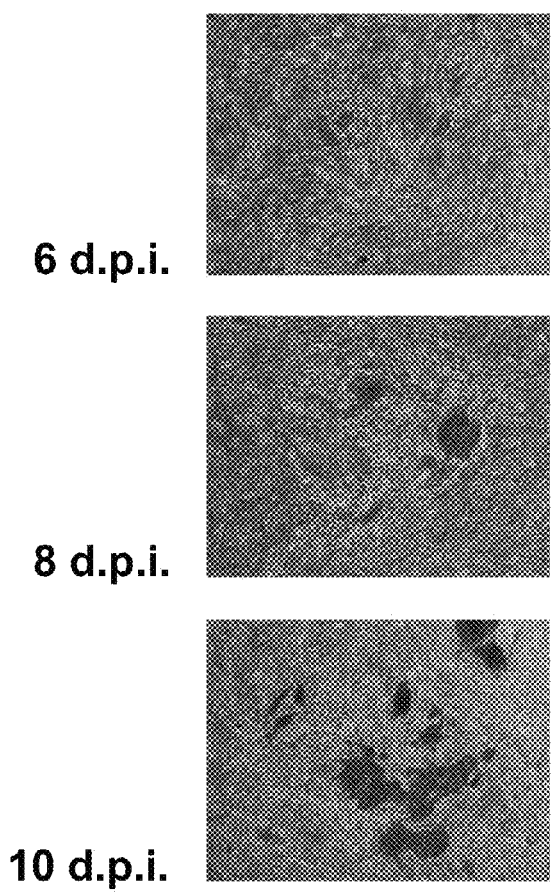
FIG. 11 is a series of time-lapse photographs using a phase contrast microscope (from 6 to 10 days post infection) showing expression of alkaline phosphatase in a human embryonic fibroblast cell infected with the hOct4/hSox2/hKlf4/hc-Myc sustained expression-inducing Sendai viral vector. Red: alkaline phosphatase. D.p.i.: days post infection.
Figure 12:
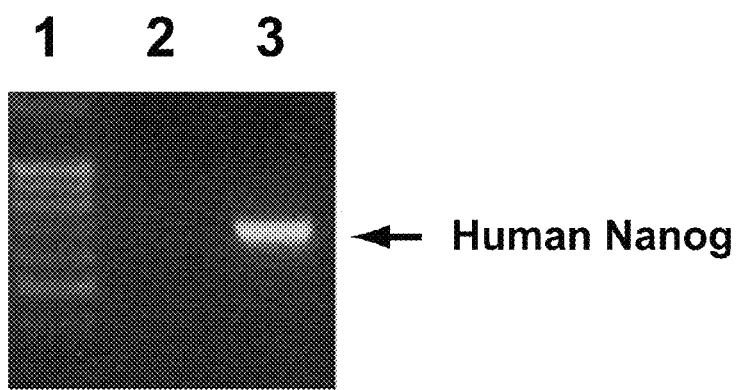
FIG. 12 depicts a photograph showing expression of endogenous human Nanog gene in a human embryonic fibroblast cell on the 14th day after infection with the hOct4/hSox2/hKlf4/hc-Myc sustained expression-inducing Sendai viral vector. Lane 1: molecular weight marker. Lane 2: normal human fibroblast not infected with vector. Lane 3: human iPS cell-like colony.

As shown in FIG. 11, 10 days after the start of infection with the hOct4/hSox2/hKlf4/hc-Myc sustained expression-inducing Sendai virus, human ES-like cell colonies formed that expressed alkaline phosphatase (see Example 20 (b)). RT-PCR analysis (see Example 20 (c)), confirmed that human Nanog expression is induced in human iPS cells that are capable of forming colonies (see FIG. 12). Using a fluorescent antibody method (see Example 20 (a)), these colonies were also shown to express SSEA-4 antigen, a marker characteristic of embryonic stem cells and iPS cells (FIG. 13). Substantially the same results were obtained using the hOct4/hSox2/hKlf4/hc-Myc sustained expression-inducing Sendai virus Version 2.

(2) Test for Induction Efficiency of Human iPS Marker-Expressing Cells

The fluorescent antibody method (see Example 20 (a)) was used to determine the amount of NP protein present in cells infected with the sustained expression-type Sendai virus. The amount of NP protein correlates with the infection rate of the recombinant Sendai virus. The number of cells in an alkaline phosphatase activity-positive colony (see Example 20 (b)) was then corrected for the rate of infection which allowed the calculation of the induction efficiency of human iPS marker-expressing cells. The results are shown in Table 2.

TABLE 2

Frequency of alkaline phosphatase-expressing cells in human embryo fibroblast cells infected with the hOct4, hSox2, hKlf4, and hc-Myc sustained expression-inducing Sendai virus as a function of time after the initiation of infection (6-10 days).

| Time (days) after infection | Frequency with respect to all cells (%) | Frequency with respect to infected cells (%) |
|---|---|---|
| 6 | 2.7 | 10.2 |
| 8 | 3.7 | 13.9 |
| 10 | 4.4 | 16.8 |

As can be seen from the results in Table 2, it became evident that the cells expressing human iPS markers can be induced with significantly higher efficiency than previous reports of iPS cell generation in which hOct4, hSox2, hKlf4 and hc-Myc were introduced into the host cell using a retroviral vector or by using other vector systems. Substantially the same results were obtained after infection with hOct4/hSox2/hKlf4/hc-Myc sustained expression-inducing Sendai virus Version 2.

(3) Change in Induction Efficiency of Human iPS Marker-Expressing Cells Due to Difference in Culture Conditions The efficiency with which human embryo-derived fibroblast cells infected with the recombinant Sendai virus are reprogrammed to become iPS cells can be significantly enhanced up to 10 fold by culturing the infected cells at 40° C. and in 2% $CO_2$, instead of the normal cell culture conditions of 37° C. in 5% $CO_2$. While this phenomenon was commonly observed after infection with the hOct4/hSox2/hKlf4/hc-Myc sustained expression-inducing Sendai virus (FIG. 16A) and the hOct4/hSox2/hKlf4/hc-Myc sustained expression-inducing Sendai virus Version 2 (FIG. 16B), it was not observed after infection with hOct4/hSox2/hKlf4/hc-Myc recombinant retrovirus (FIG. 16C).

Example 9

Figures 14, 14A, 14B:
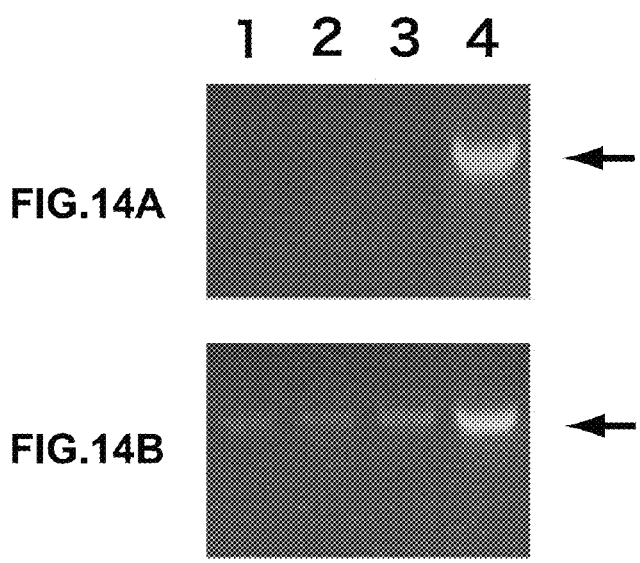
FIG. 14 depicts two photographs showing expression (indicated by the arrows) of Sendai virus NP gene (FIG. 14A) and endogenous human Nanog gene (FIG. 14 B) in a human iPS marker-expressing cell after removal of a sustained expression-inducing Sendai viral vector using an siRNA. Lane 1: human iPS cell (TIG/MKOS #19). Lane 2: human iPS cell (TIG/MKOS #32). Lane 3: human iPS cell (TIG/MKOS #30). Lane 4: iPS cell-like colony before removal of vector.
Figure 15:
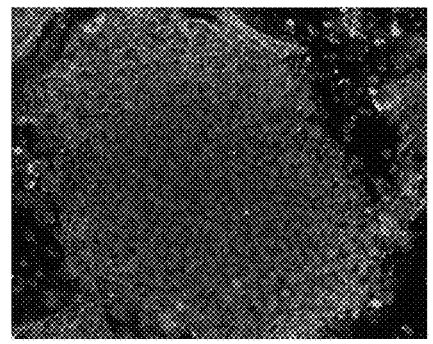
FIG. 15 depicts a photograph showing expression of SSEA-4 antigen and endogenous human Oct4 protein in a human iPS marker-expressing cell after removal of a sustained expression-inducing Sendai viral vector using an siRNA. Green: human pluripotent stem cell-specific antigen SSEA-4. Red: human pluripotent stem cell-specific antigen Oct4.

Production of Human iPS Cells by Removing the RNA Genome of Sustained Expression-Type Sendai Viral Vector The human iPS marker-expressing cells obtained in Example 8 were successfully cultured for long periods of time. One month after infection with the vector, fluorescent antibody staining of Sendai virus NP protein confirmed that no vector RNA genome remained in the cells as described in Example 5. RT-PCR analysis of NP gene expression as described in Example 7 further confirmed the absence of viral vector sequences in these cells (FIG. 14A). In addition, RT-PCR analysis of Nanog mRNA (see Example 20 (c)), demonstrated that endogenous Nanog expression persists in iPS cells even after the cells no longer contain any detectable viral vector sequences (FIG. 14B). The same is true for the stem cell markers human SSEA-4 and Oct-4 (see FIG. 15) detected using appropriate fluorescent antibodies (see Example 20 (a)) further indicating that these endogenous stem cell markers do not require the persistent expression of the reprogramming genes in order to maintain the stem cell phenotype.

Figure 17:
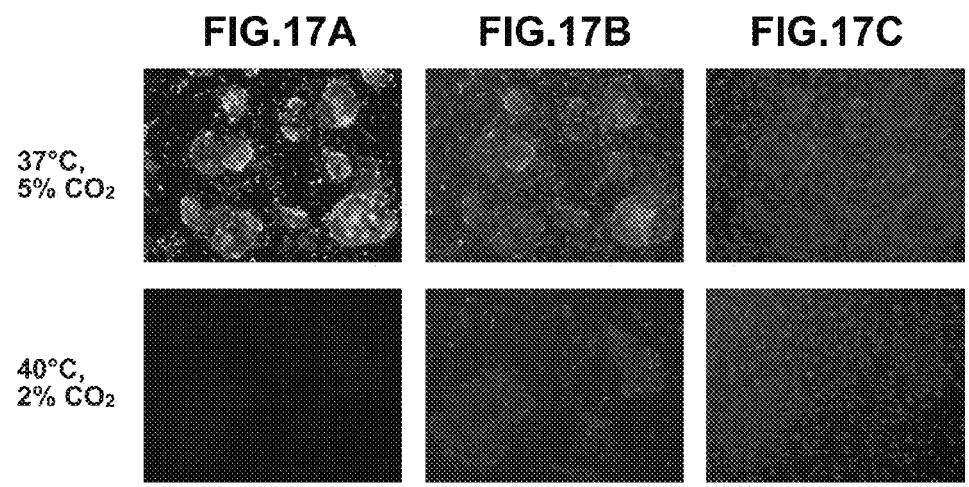
FIG. 17 depicts a photograph showing respective efficiencies of removal of a Sendai viral vector from a human iPS marker-expressing cell (measured by the reduced detection of Sendai virus antigen using a fluorescent antibody method), under normal culture conditions (37° C., 5% $CO_2$) and under high-temperature culture conditions (40° C., 2% $CO_2$), each for 7 days.

Removal of the viral vector sequences can be enhanced by subjecting the newly formed human iPS marker-expressing cells to subculture conditions at 40° C., 2% $CO_2$, instead of the normal conditions 37° C., 5% $CO_2$ (FIG. 17). The sustained expression-type Sendai viral vector used in this test has the property that gene expression deteriorates rapidly at high temperature (40° C.), which facilitates the removal of the vector from the host cell.

Example 10

Preparation of Chimeric Mouse from Mouse iPS Cells

The iPS cell line KOSM #24 was established from MEFs derived from a Nanog-EGFP (Enhanced Green Fluorescent Protein) knock-in mouse (STOCK Tg (Nanog-GFP, Puro) 1Yam), as described in Examples 5 and 6 using the hOct4/hSox2/hKlf4/hc-Myc sustained expression-inducing Sendai viral vector Version 2. A chimeric mouse was prepared according to a method described in the following Reference (Manipulating the Mouse Embryo, A Laboratory Manual, Third Edition (Nagy, A., et al, Cold Spring Harbor Laboratory Press, 2003)).

Figure 18:
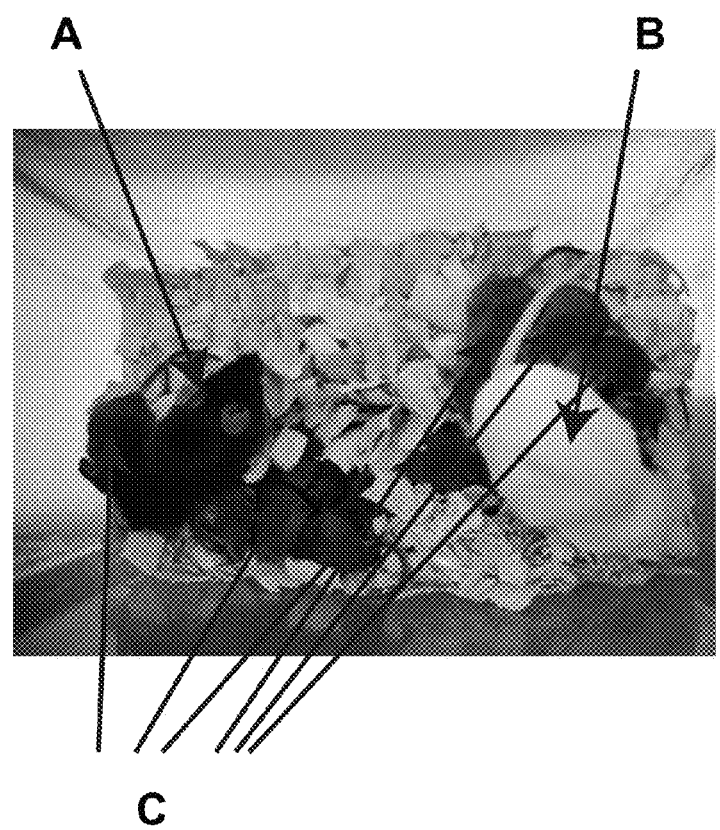
FIG. 18 depicts a photograph showing a mouse iPS cell-derived chimeric mouse prepared using a hOct4/hSox2/hKlf4/hc-Myc sustained expression-inducing Sendai viral vector Version 2, and germ-line transmission from the mouse. A: Mouse A (iPS cell-KOSM #24-derived chimeric mouse male); B: Mouse B (ICR mouse, female); C: Baby mice from mouse A and mouse B.

An eight-cell embryo was collected from the uterus of an ICR mouse (female, 6 to 8 week-old) on the 2.5th day of pregnancy and washed in M2 Medium. The embryo was then cultured in KSOM (Potassium Simplex Optimized Medium) for 1 to 2 hours, and then subjected to a microinjection. Mouse iPS cells were first dispersed with trypsin, and 10 to 15 iPS cells were introduced into the embryo from a small hole formed in a zona pellucida. Subsequently, the embryo was cultured in KSOM for additional 24 hours, and then transplanted into the uterus of a female ICR mouse (surrogate parent mouse) crossed with a male mouse with bound ductus deferens. The chimaerism of the mouse after childbirth and germ-line transmission to progeny was determined by checking hair color and by detecting the presence of genes unique to the iPS cells. High levels of chimaerism, and germ-line transmission were observed (FIG. 18).

Example 11

Formation of Teratoma from Human iPS Cells

Figure 19:
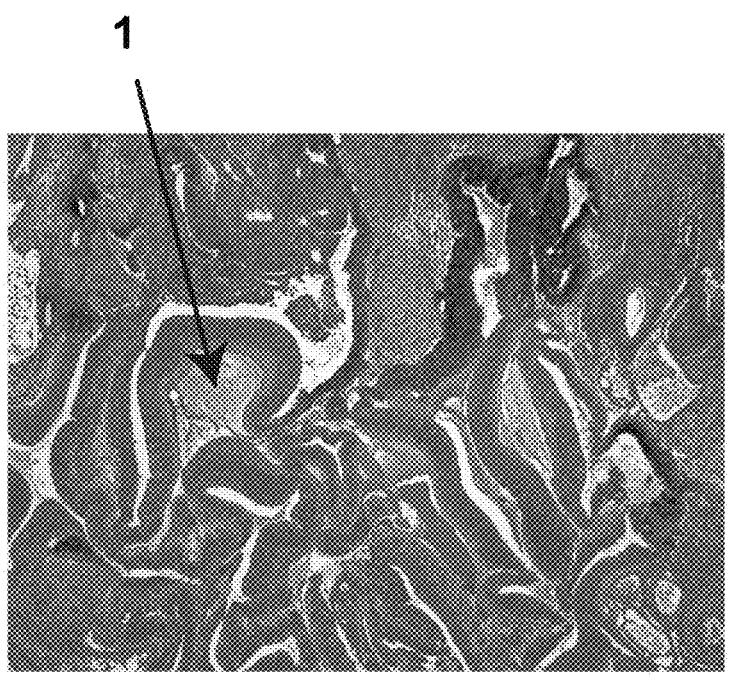
FIG. 19 depicts a photograph of a tissue slice of a teratoma derived from a human iPS marker-expressing cell after removal of a hOct4/hSox2/hKlf4/hc-Myc sustained expression-inducing Sendai viral vector therefrom. 1: Intestinal canal (derived from endoderm); 2: Cartilage (derived from mesoderm); 3: Neural tube (derived from ectoderm).
Figure 19:
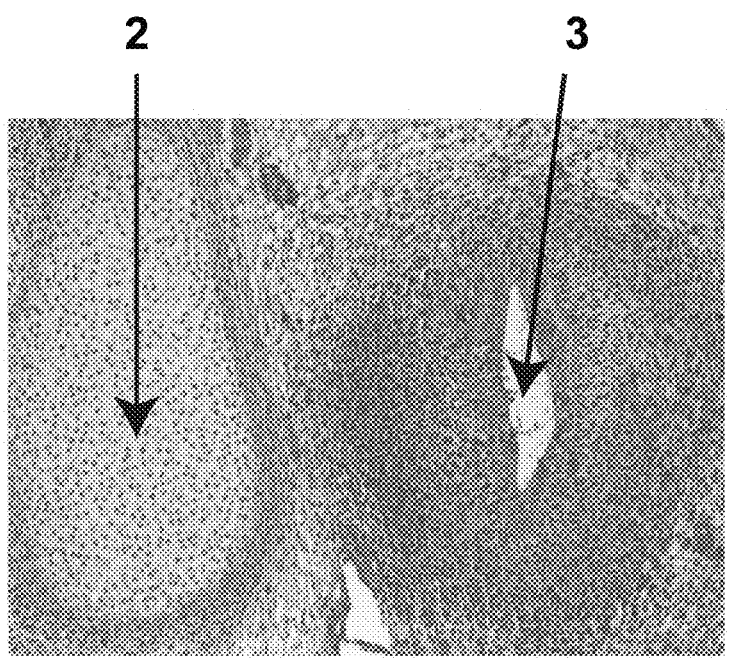

The human iPS cells obtained in Example 9 were adjusted to a concentration of $1.0 \times 10^6$ cells/40 μL Hepes Buffered Saline Solution (HBSS)/mouse. A testis of a mouse (C.B17/Icr-scidJcl) anesthesized with Nembutal and isoflurane, was inoculated with iPS cells. After about 8 weeks, a visually identifiable teratoma formed. After 60 days post-inoculation, the teratoma was excised and fixed in Bouin's fixative solution (75% of saturated picric acid, 12% of formalin, 3% of acetic acid), and dehydrated by a treatment with 70% ethanol solution (1 hour), 90% ethanol solution (1 hour), 100% ethanol solution (1 hour, twice), 50% ethanol solution, 50% 2-butanol solution (1 hour) and 100% 2-butanol solution (30 minutes, twice). The specimen was then fixed in paraffin. Sections of 6 μm thickness were then prepared using a microtome, the section were deparaffinized, and subjected to HE staining Differentiation to all of three germ layers was observed within each teratocarcinoma analyzed (FIG. 19).

Example 12

Preparation of hOct4/hSox2/hKlf4/hc-Myc Sustained Expression-Inducing Sendai Viral Vector Version 2

(1) Human c-Myc gene was amplified from a plasmid pJL1 including a full-length human c-Myc cDNA by a PCR method using two primers consisting of 5'-ACTAGCTAGCT-TAGA CGCTGGATTTTTTTCGGGTAGTGG-3' (SEQ ID NO: 32 in the Sequence Table (N-terminal side)) and 5'-GTC-CACCGGTCTTACGCACAAGAGTTCCGT-3' (SEQ ID NO: 33 in the Sequence Table (C-terminal side)) as hc-Myc gene-amplifying primers. The termini of the double-stranded PCR DNA fragment were then cleaved at the Nhe I and Age I sites, and cloned between the Nhe I and Age I sites of the pMO084 prepared in Example 2 to generate plasmid pMO118 (see FIG. 20).

Figure 20:
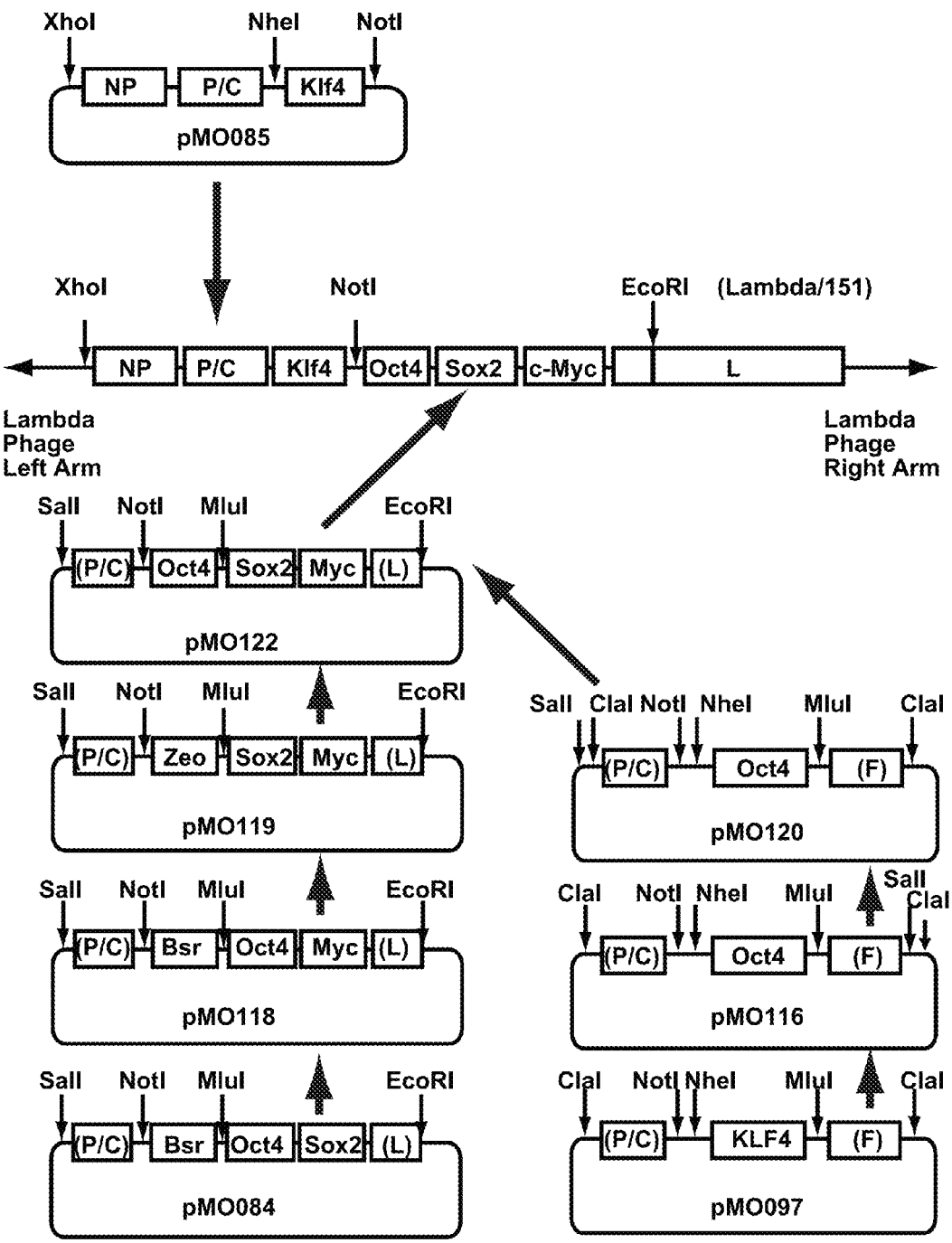
FIG. 20 is a diagram showing the preparation of a template cDNA for producing the hOct4/hSox2/hKlf4/hc-Myc sustained expression-inducing Sendai viral vector Version 2.

Human Sox2 gene was amplified from pUC57-Sox2 by a PCR method using two primers hSox2 gene-amplifying primers consisting of 5'-AGTACCTAGGCGCATGTACAA-CATGATGGAGACGG-3' (SEQ ID NO: 34 in the Sequence Table (N-terminal side)) and 5'-GTCCGACGTCCTCACAT-GTGTGAGAGG GGCAGT-3' (SEQ ID NO: 35 in the Sequence Table (C-terminal side)). The termini of the double-stranded PCR DNA fragment were cleaved at Avr II and Aat II sites, and cloned between the Avr II and Aat II sites of the pMO118 plasmid to form pMO119 (FIG. 20).

Human Oct4 gene was amplified from pUC57-Oct4 by a PCR method using two hOct4 gene-amplifying primers consisting of
5'-ACTAGCTAGCGGTTCCCCATGGCGGGA-CACCTGGCTTCGG-3' (SEQ ID NO: 36 in the Sequence Table (N-terminal side)) and 5'-GGTCCACGCGT-TCAGTTTGAATGC ATGGGAGAGCC-3' (SEQ ID NO: 37 in the Sequence Table (C-terminal side)). The termini of the double-stranded PCR DNA fragment was then cleaved at Nhe I and Mlu I sites, and inserted between the Nhe I and Mlu I sites of the pMO097 to generate the plasmid pMO116. The orientation of a Cla I-Cla I fragment of the pMO116 was reversed to obtain pMO120. Next, a Sal I and Mlu I fragment of pMO119 was combined with a fragment between Sal I and Mlu I sites of pMO120 to generate pMO122 (FIG. 20).

Based on the plasmids obtained thus far, a T7 promoter sequence to SeV (1 to 3655 with Klf4), and SeV (3655 to 10480 with Oct4/Sox2/c-Myc), were cut out from pMO085 and pMO122 respectively and combined with a DNA fragment of SeV (10480 to 15384)+the right arm of the λ DASH II obtained by cutting the λ/151 at EcoR I site. The combination was then cloned to prepare λ/SeVp (Mp+Klf4, ΔM:: Oct4, ΔF:: Sox2, ΔHN:: c-Myc) (FIG. 20) (a cDNA complementary to a full-length genome of a hOct4/hSox2/hKlf4/hc-Myc sustained expression-inducing Sendai viral vector Version 2 described as SEQ ID NO: 38 in the Sequence Table).

(2) Preparation of hOct4/hSox2/hKlf4/hc-Myc Sustained Expression-Inducing Sendai Viral Vector Version 2

In accordance with the protocol described in Example 3, a hOct4/hSox2/hKlf4/hc-Myc sustained expression-inducing Sendai viral vector Version 2 was prepared from the cDNA complementary to a full-length genome of the hOct4/hSox2/hKlf4/hc-Myc sustained expression-inducing Sendai viral vector Version 2.

Example 13

Preparation of hOct4/hSox2/hKlf4/hc-Myc Sustained Expression-Inducing Sendai Viral vector Version 3 Capable of Being Automatically Removed from iPS Cell (1) In order to clone a sequence formed by connecting four target sequences for mir-302a which is ES cell-specific of miRNA, two sets of oligo DNAs consisting of a set of 5'-CCGGTTATCACCAAAACATGGAAGCACT-TACGATTCACCAAAACATGGAAGCACTT AGGTACC- 3' (SEQ ID NO: 39 in the Sequence Table) and 5'-TAAGT-GCTTCCATGT TTTGGTGAATCGTAAGTGCTTCCAT-GTTTTGGTGATAA-3' (SEQ ID NO: 40 in the Sequence Table) and a set of 5'-TCACCAAAACATGGAAGCACT-TACGATTCACCAAAA CATGGAAGCACTTAA-3' (SEQ ID NO: 41 in the Sequence Table) and 5'-CCGGTTAAGT GCTTCCATGTTTTGGTGAATCGTAAGT-GCTTCCATGTTTTGGTGAGGTACC-3' (SEQ ID NO: 42 in the Sequence Table) were annealed, and then ligated together. Ligated DNA was cloned into pGL4.12 (Promega Corp.) cut at Age I site to obtain pNK300.

Figure 21:
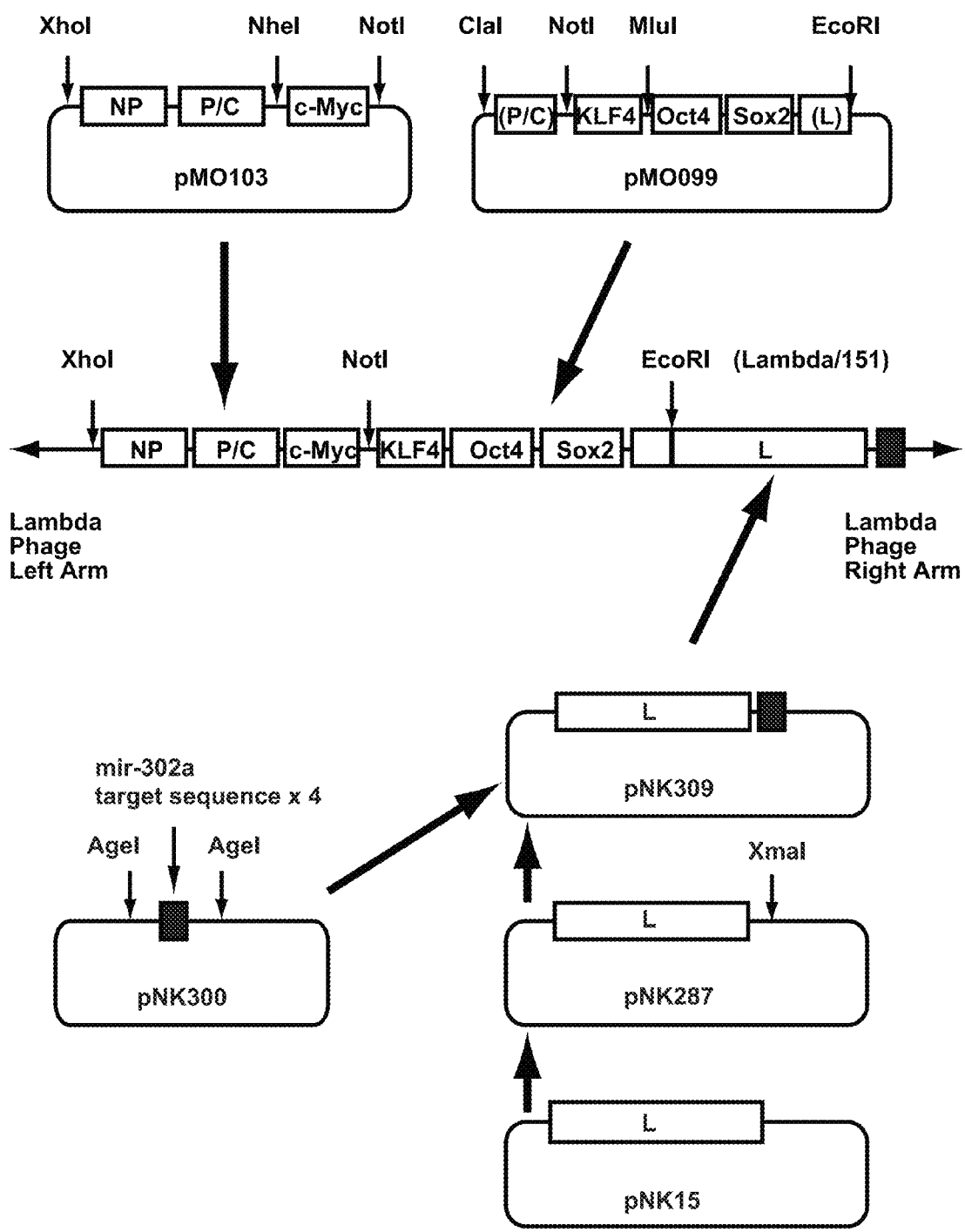
FIG. 21 is a diagram showing the preparation of a template cDNA for producing a hOct4/hSox2/hKlf4/hc-Myc sustained expression-inducing Sendai viral vector Version 3.

A plasmid vector pNK15 (SEQ ID NO: 43 in the Sequence Table) was prepared by inserting the SeV strain Cl.151 genome cDNA (bases 9014 to 15384), a hairpin ribozyme sequence of a tobacco ringspot virus and a termination sequence of T7 RNA polymerase into pBluescript II SK(+) (Agilent Technologies, Inc.)). Then, using 5'-GA-CAGCTCGTAATCCC GGGTCCCTATCGTGC-3' (SEQ ID NO: 44 in the Sequence Table (sense strand)) and 5'-GCAC-GATAGGGACCCGGGATTACGAGCTGTC-3' (SEQ ID NO: 45 in the Sequence Table (antisense strand)) as an Xma I-recognition sequence insertion site-forming primer, an Xma I-recognition sequence was inserted into the plasmid vector pNK15 at a site just after SeV (15244) by a Quickchange Site-directed Mutagenesis II kit (Agilent Technologies, Inc.), to obtain pNK287. A fragment obtained by cutting the pNK300 at Age I site was inserted into the Xma I site of the pNK287 to generate pNK309 (FIG. 21).

T7 promoter sequence to SeV (1 to 3655 with c-Myc), and SeV (3655 to 10480 with Klf4/Oct4/Sox2), was cut out from pMO103 and pMO099 as described in Example 3, and the connected SeV (9014 to 15384)-hairpin ribozyme sequence-T7 RNA polymerase termination sequence was cut out from the pNK309. Then, these fragments were combined with a DNA fragment consisting of right and left arms of the λ DASH II, and the obtained combination was cloned to create λ/SeVp (Mp+myc, ΔM:: Klf4, ΔF:: Oct4, ΔHN:: Sox2, L+mir302T4) (FIG. 21) (a cDNA complementary to a full-length genome of a hOct4/hSox2/hKlf4/hc-Myc sustained expression-inducing Sendai viral vector Version 3 is described as SEQ ID NO: 46 in the Sequence Table).

(2) Preparation of hOct4/hSox2/hKlf4/hc-Myc Sustained Expression-Inducing Sendai Viral Vector Version 3

In accordance with the process described in the Example 3, a hOct4/hSox2/hKlf4/hc-Myc sustained expression-inducing Sendai viral vector Version 3 was prepared from the cDNA complementary to a full-length genome of the hOct4/hSox2/hKlf4/hc-Myc sustained expression-inducing Sendai viral vector Version 3.

Example 14

Evaluation on Temporal Change in Removal of RNA Genome of Sustained Expression-Type Sendai Viral Vector from Cell Using siRNA As for the technique of removing the vector genome from a cell stably transfected with the RNA genome of the sustained expression-type Sendai viral vector, using siRNA, as described in the Example 4, an additional evaluation was carried out to quantitatively analyze temporal change in the removal and confirm that no vector genome remained in the cell after siRNA treatment, as follows.

As a marker of gene expression by the sustained expression-type Sendai viral vector, unstable firefly luciferase gene (Luc2CP, Promega Corp.) and *Escherichia coli* hygromycin B-resistant gene (HygB) were used. A luciferase activity reflects the copy number of the recombinant Sendai viral RNAs, and the number of hygromycin B-resistant cells reflects the number of cells transfected with the sustained expression-type Sendai viral vector.

A KO/HygB/EGFP/Luc2CP-loaded sustained expression-type Sendai viral vector containing a Luc2CP gene and a HygB gene was prepared by substituting the hOct4 gene, the hSox2 gene, the hKlf4 gene and the hc-Myc gene with the Kusabira Orange (KO) gene (Medical & Biological Laboratories, Co. Ltd.), HygB gene, Enhanced Green Fluorescent Protein (EGFP) gene, and Luc2CP gene, respectively, using the same methodology as that described for the cloning of hOct4/hSox2/hKlf4/hc-Myc sustained expression-inducing Sendai viral vector (see Example 3). Two types of short interfering RNAs (siRNAs) (same as Example 4) were used for suppressing expression of L gene (#1: sense strand 5'-GG-UUCAGCAUCAAAUAUGAAG-3' (SEQ ID NO: 14 in the Sequence Table) and antisense strand 5'-UCAUAU-UUGAUGCUGAACCAU-3' (SEQ ID NO: 15 in the Sequence Table). siRNA complimentary to sea-firefly luciferase gene (Rluc, Promega Corp.) served as negative control because it did not have any homologous with the Sendai viral vector genome.

In order to check for the removal of the viral genome by the siRNA, a HeLa cell stably transduced with the genome of the sustained expression-type Sendai viral vector containing a Luc2CP gene and HygB gene was seeded into a 24-well plate at a concentration of $3\times10^4$ cells/0.4 mL medium (MEM, 10% fetal bovine serum)/well. The siRNA was diluted with Opti-MEM to a final concentration of 40 nM, and 1 μL of Lipofectamine RNAiMAX (Lifetechnologies, Inc.) was added the cell medium at room temperature for 20 minutes. Then, the siRNA was added to the above cells. Subsequently, the cells were collected at different times after transfection. On the 3rd and 6th days, the cells were subcultured under the above conditions, and the siRNA was added again using the above conditions. As a result, the luciferase activity as an index of an amount of the vector in the cell was lowered with time. On and after the 8th day, luciferase activity was no longer detectable (see FIG. 22A).

Cells transfected with siRNA were passaged 3 times over a 4 week period in the absence of siRNA. Cells were then cultured in the presence of selective medium containing 200 μg/mL of hygromycin B, and further cultured another week. As a result of the selection, no hygromycin B-resistance clone emerged, which demonstrates that none of the cells contained the sustained expression-type Sendai viral vector containing with the HygB gene (FIG. 22B).

Example 15

Evaluation of the Gene Expression Patterns of Two Foreign Genes Incorporated into the Sustained Expression-Type Sendai Viral Vector Previous experiments show that all four types of reprogramming genes need to be expressed simultaneously in a common cell, in order to produce an iPS cell. If the balance of expression intensity between the reprogramming genes is changed, the reprogramming efficiency decreases (Reference: Papapetrou, et al., Proc. Natl. Acad. Sci. USA, 106, 12759-12764, 2009), and a low-quality cell line having a similar configuration to an iPS cell but without pluripotency is likely to emerge (Reference: Chan, et al., Nat. Biotech., 27, 1034-1037, 2009). Thus, the method of producing iPS cells with high efficiency and excellent reproducibility needs to meet the following two requirements: 1) the four types of reprogramming genes must be introduced simultaneously into a common cell; and 2) the transduced reprogramming genes must be expressed simultaneously within each cell. To introduce the four types of reprogramming genes into a cell using the sustained expression-type Sendai viral vector, all of the reprogramming genes were cloned into a single vector, as shown in the Examples of the present invention. To determine if this cis configuration was more efficient at inducing iPS colonies than a trans configuration, each of the reprogramming genes was cloned into individual Sendai vectors. Virus produced from each of these vectors were then mixed and used to infect differentiated cells, as disclosed in the PCT/JP2009/062911 and Fusaki, et al., Proc. Jpn. Acad. Ser. B85, 348-362, 2009). Differences between the expression patterns of a foreign gene in the cis or trans configuration was then evaluated, by comparing expression patterns of two types of genes: the Kusabira Orange (KO) gene and Enhanced Green Fluorescent Protein (EGFP) gene present on each of the Sendai viral vectors.

The KO/HygB/EGFP/Luc2CP-loaded sustained expression-type Sendai viral vector described in Example 14 contains both the KO and EGFP genes. Further, for use as a vector loaded with only KO gene, a Zeo/KO/CLuc-loaded sustained expression-type Sendai viral vector was prepared by removing the hKlf4 gene from the hOct4/hSox2/hKlf4 sustained expression-inducing Sendai viral vector as described in the Example 2, and substituting the Bsr gene, the Oct4 gene and Sox2 gene with zeocin-resistant (Zeo) gene, the KO gene and secreted luciferase (CLuc) gene, respectively. For use as a vector loaded with only the EGFP gene, a Bsr/EGFP/gp91phox-loaded sustained expression-type Sendai viral vector was prepared by removing the hKlf4 gene from the hOct4/hSox2/hKlf4 sustained expression-inducing Sendai viral vector as described in the Example 2, and substituting the Oct4 gene and Sox2 gene with EGFP gene and chronic granulomatous disease-caused gene (gp91phox), respectively.

The monkey $LLCMK_2$ cell line was infected with the KO/HygB/EGFP/Luc2CP-loaded vector at a multiplicity of infection (m.o.i) of 5 vector particles/cell, and the resulting cells were selected with hygromycin B, to establish a cell pool $LLCMK_2$ (SeVdp/KO/HygB/EGFP/Luc2) containing the KO/HygB/EGFP/Luc2CP-loaded vector. In the same manner, the Zeo/KO/CLuc-loaded vector and the Bsr/EGFP/gp91phox-loaded vectors were mixed at a vector particle ratio of 1:1, and $LLCMK_2$ cells were infected with the mixed vectors at a m.o.i of 5 vector particles/cell, and the resulting cells were simultaneously selected with blasticidin S and Zeocin, to establish a cell pool $LLCMK_2$ (SeVdp/Zeo/KO/CLuc+SeVdp/Bsr/EGFP/91phox) having both vectors in each of the cells.

The two types of cell lines were then observed by fluorescent microscopy (Zeiss), and two images thereof were superimposed on each other, while assigning a red pseudocolor and a green pseudocolor to fluorescence generated by KO and fluorescence generated by EGFP, respectively. The image of $LLCMK_2$ (SeVdp/KO/HygB/EGFP/Luc2) cells became yellow which indicates that KO and EGPF are simultaneously expressed, whereas the image of the $LLCMK_2$ (SeVdp/Zeo/KO/CLuc+SeVdp/Bsr/EGFP/91phox) cells indicated a mixture of red/yellow/green-colored cells, which shows that a balance between the expression of KO and EGFP is significantly different in each cell (FIG. 23A).

In order to quantitatively analyze the balance between the expressions of KO and EGFP, the above cells were analyzed by a Fluorescent-activated Cell Analyzer (BD FACSCalibur, Becton, Dickinson and Company). $10^4$ $LLCMK_2$ (SeVdp/KO/HygB/EGFP/Luc2) cells and $10^4$ $LLCMK_2$ (SeVdp/Zeo/KO/CLuc+SeVdp/Bsr/EGFP/gp91phox) cells were suspended in 2 mL of buffer to measure the fluorescence intensity (FL1) of EGFP and a fluorescence intensity (FL2) of KO. The analysis shows that the ratio between the fluorescence intensities of EGFP and KO in the $LLCMK_2$ (SeVdp/KO/HygB/EGFP/Luc2) is constant, whereas the ratio in the $LLCMK_2$ (SeVdp/Zeo/KO/CLuc+SeVdp/Bsr/EGFP/91phox) cells fluctuates significantly (FIG. 23B). In an analysis of the ratio between FL1 and FL2, 50% or more of the $LLCMK_2$ (SeVdp/KO/HygB/EGFP/Luc2) cells had the same ratio, whereas the ratio in the $LLCMK_2$ (SeVdp/Zeo/KO/CLuc+SeVdp/Bsr/EGFP/91phox) was widely distributed in a broad range from 0 to 100% (FIG. 23C).

The above results show that the function of simultaneously introducing two or more types of genes into each cell to induce gene expression at the same ratio can be achieved by the process of cloning the four types of reprogramming genes on a single common vector, as shown in the Examples of the present invention, but cannot be readily achieved when each of the four types of reprogramming genes are cloned into individual vectors that are mixed together prior to infection as disclosed in the PCT/JP2009/062911 and the Fusaki, et al., Proc. Jpn. Acad. Ser. B85, 348-362, 2009.

Example 16

Induction of iPS Cells Using Sustained Expression-Type Sendai Viral Vectors Each Loaded with a Reprogramming Gene iPS cell production efficiency with Sendai vector comprising all four types of reprogramming genes on a single common vector to produce iPS cells, as shown in the Examples of the present invention, was then compared to iPS induction by infection with Sendai virus containing only one of the reprogramming genes, as disclosed in PCT/JP2009/062911 and the Fusaki, et al., Proc. Jpn. Acad. Ser. B85, 348-362, 2009.

The hOct4/hSox2/hKlf4/hc-Myc sustained expression-inducing Sendai viral vector containing all four types of reprogramming genes was compared with the hOct4/hSox2/hKlf4 sustained expression-inducing Sendai viral vector comprising three reprogramming genes (as shown in the Example 2), and a Zeo/KO/hc-Myc sustained expression-inducing Sendai viral vector containing just c-Myc. The Zeo/KO/hc-Myc sustained expression-inducing Sendai viral vector was prepared by substituting the Oct4 gene, the Sox2 gene and the Klf4 gene of the hOct4/hSox2/hKlf4 sustained expression-inducing Sendai viral vector with the Zeo gene, KO gene and c-Myc gene, respectively.

Figure 24:
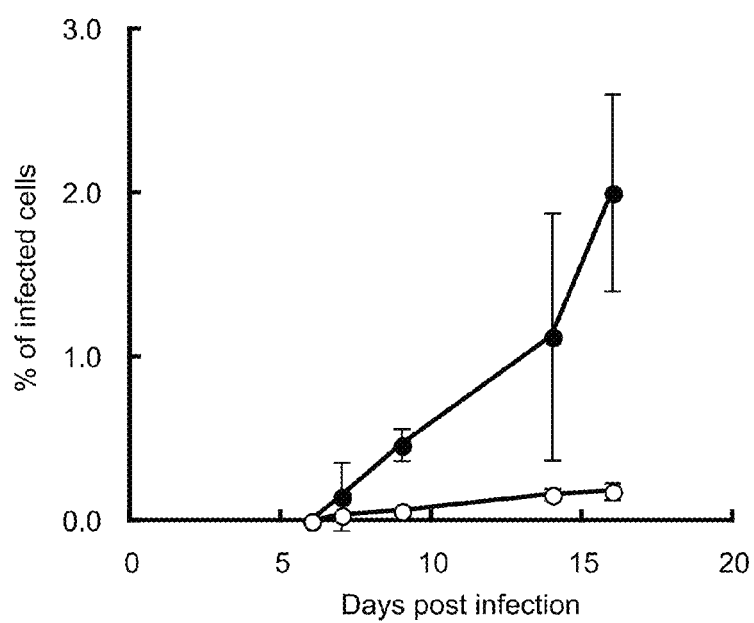
FIG. 24 depicts a graph showing the temporal change in emergence efficiency of a mouse iPS marker-expressing cell, after transfection with either a single common sustained expression-type Sendai viral vector comprising four types of reprogramming genes or after transfection with individual sustained expression-type Sendai viral vectors each comprising a different reprogramming gene. Filled circles: hOct4/hSox2/hKlf4/hc-Myc sustained expression-inducing Sendai viral vector. Open circles: a mixture of hOct4/hSox2/hKlf4 sustained expression-inducing Sendai viral vector and Zeo/KO/hc-Myc sustained expression-inducing Sendai viral vector.

According to the Example 5, cells were infected with the hOct4/hSox2/hKlf4/hc-Myc sustained expression-inducing Sendai virus or a mixture of hOct4/hSox2/hKlf4 sustained expression-inducing Sendai virus with the Zeo/KO/hc-Myc sustained expression-inducing Sendai virus at a vector particle ratio of 1:1. Emergence of iPS cell colonies was checked by an index based on emergence of an alkaline phosphatase-positive cell colony. As a result, it could be shown that cloning the four types of reprogramming genes on the single common vector produces iPS cells with a cell production efficiency far greater than that obtained by mixing viruses each having only one of the reprogramming gene (FIG. 24).

Example 17

Induction of iPS Cells Using hOct4/hSox2/hKlf4/hc-Myc Sustained Expression-Inducing Sendai Virus Version 3

TIG3 cells was seeded on a 12-well plate at a density of $1.0\times10^5$ cells/well. On the next day, the hOct4/hSox2/hKlf4/hc-Myc sustained expression-inducing Sendai viral vector prepared in Example 3, or the hOct4/hSox2/hKlf4/hc-Myc sustained expression-inducing Sendai viral vector Version 3 prepared in Example 13, was added to the medium to induce human iPS cells according to Example 8. Colonies was subcultured twice. Then, on the 24th day after infection, colonies were fluorescently stained using an antibody against NP protein As shown in FIG. 25A, colonies induced with hOct4/hSox2/hKlf4/hc-Myc sustained expression-inducing Sendai viral vector Version 3 did not contain any vector (FIG. 25) whereas expressed iPS/ES marker SSEA-4 antigen (FIG. 25B).

The above result clearly shows that, when human iPS cells are induced with the hOct4/hSox2/hKlf4/hc-Myc sustained expression-inducing Sendai virus Version 3, the vector is automatically removed by the microRNA, mir-302a, expressed in the induced iPS cell.

Example 18

Establishment of iPS Cells from Human Peripheral-Blood Mononuclear Cells 20 mL of adult blood was diluted with 20 mL of PBS (−), and layered on 6 mL of Lymphoprep. The blood was then centrifuged at 1.800 r.p.m. for 30 minutes to separate an upper layer of platelets, an intermediate layer including mononuclear cells and a lower layer including red blood cells. The intermediate layer was washed with PBS (−) to obtain human peripheral-blood mononuclear cells. In accordance with the technique described in Example 8, the cells were infected with hOct4/hSox2/hKlf4/hc-Myc sustained expression-inducing Sendai virus, and then cultured. iPS cells positive for alkaline phosphatase and having a morphology similar to that of a human ES cell formed (FIG. 26). Cell colonies were not detected in a negative control comprising cells that were not infected with the Sendai vector.

Example 19

Comparison between Gene Expression Patterns in Human iPS Cells Produced with Sustained Expression-Type Recombinant Sendai Virus (1) Preparation of Target RNA to be Analyzed iPS cells produced using the hOct4/hSox2/hKlf4/hc-Myc sustained expression-inducing Sendai virus according to the process in Example 8 were cultured on matrigel (Becton, Dickinson and Company) in MEF conditioned medium without any feeder cells. $1.0\times10^6$ cells were then collected and whole cell RNA was extracted using ISOGEN (Nippon Gene Co. Ltd.). As a control, five human ES cell lines established at the Institute for Frontier Medical Sciences, Kyoto University, were cultured in the absence of feeder cells, and whole cell RNA was extracted, in the same manner.

(2) Analysis of Gene Expression 0.5 µg of whole cell RNA was labeled with Cy3, using Quick Amp Labeling Kit (Agilent Technologies, Inc.). The labeled RNA was hybridized with Whole Human Genome (4x44k) DNA array (Agilent Technologies, Inc.), using a Gene Expression Hybridization Kit (Agilent Technologies, Inc.), and a signal was acquired using Agilent DNA Microarray Scanner. The acquired signal was analyzed using GeneSpringGX10 software (Agilent Technologies, Inc.) to obtain a correlation coefficient between respective gene expression patterns of cell clones (FIG. 27A). The gene expression patterns of human iPS cells produced using the hOct4/hSox2/hKlf4/hc-Myc sustained expression-inducing Sendai virus were significantly similar to each other, as evidenced by a correlation coefficient of 0.98 or more. This shows that iPS cells having with significantly uniform properties can be established by the method of the present invention. In addition, each of the iPS cells subjected to this analysis expressed a marker gene which was strongly expressed in human ES cells and at the same expression level as that observed in ES cells (FIG. 27B). This means that the gene expression of iPS cells has high correlativity with that of human ES cells (FIG. 27C).

Example 20

Quantitation of Gene Expression Found in Examples 5 to 11

(a) Verification of Gene Expression by Indirect Fluorescent Antibody Method

Expressions of human Oct4, human Sox2, human Klf4, human c-Myc, mouse SSEA-1, human SSEA-4 and Sendai virus NP gene in each cell were verified using antibodies to each of the antigens. A primary antibody and a dilution rate used herein are as follows. The human Oct4: rabbit anti-Oct4 polyclonal antibody (Abcam Inc.) [×100]; the human Sox2: rabbit anti-Sox2 polyclonal antibody (Abcam Inc.) [×100]; the human Klf4: rabbit anti-Klf4 polyclonal antibody (CeMines Inc.) [×100]; the human c-Myc: rabbit anti-c-myc polyclonal antibody (Santa Cruz Biotechnology Inc.) [×100]; the SSEA-1: mouse anti-SSEA-1 monoclonal antibody (Santa Cruz Biotechnology Inc.) [×200]; the SSEA-4: mouse anti-SSEA-4 monoclonal antibody (Santa Cruz Biotechnology Inc.) [×200]; and the Sendai virus NP: mouse anti-NP monoclonal antibody [×200] or rabbit anti-NP polyclonal antibody [×1000].

(b) Alkaline Phosphatase Staining

Culture medium was first removed, and the cells were washed with PBS. Then, Vector Red Alkaline Phosphatase Kit I (Vector Laboratories Inc.) was added to the cells, and left to react at room temperatures for 20 to 30 minutes. Cells having alkaline phosphatase activity stained red.

(c) Verification of the Expression of Mouse Nanog, Mouse Oct4, Human Nanog and Sendai Virus NP Gene by Reverse Transcription-Polymerase Chain Reaction (RT-PCR) Method.

Total RNA was extracted from iPS cells using ISOGEN (Nippon Gene Co. Ltd.). cDNA was synthesized using random primer according to instructions in the SuperScript III First strand synthesis system (Life technologies, Inc.). Target cDNA was then amplified by PCR using the following primers. The mouse Nanog: 5'-GGAAGCATCGAATTCTGGGA-3' (SEQ ID NO: 18 in the Sequence Table (sense strand)), 5'-CGGAGCAGCATTCCAAGGCT-3' (SEQ ID NO: 19 in the Sequence Table (antisense strand)); the mouse Oct4: 5'-TGAGCCGTCTTTCCACCAGG-3' (SEQ ID NO: 20 in the Sequence Table (sense strand)); 5'-ACATGGTCTCCAGACTCCAC-3' (SEQ ID NO: 21 in the Sequence Table (antisense strand)); the human Nanog: 5'-AGCATCCGACTGTAAA GAAT-3' (SEQ ID NO: 22 in the Sequence Table (sense strand)), 5'-CCTCTCCACA GTTATAGAAG-3' (SEQ ID NO: 23 in the Sequence Table (antisense strand)); SeV NP: 5'-AGACCCTAAGAGGACGAAGA-3' (SEQ ID NO: 24 in the Sequence Table (sense strand)), 5'-ACTCCCATGGCG-TAACTCCATAGTG-3' (SEQ ID NO: 25 in the Sequence Table (antisense strand)).

(d) Genotyping of Mouse Cell

Genomic DNA was extracted using DNeasy Tissue Kit (QIAGEN Inc.). The extracted DNA was subjected to PCR using the following primer to determine a genotype. D18Mit4: 5'-ACTGTTGCTGG GGAATGG-3' (SEQ ID NO: 26 in the Sequence Table (sense strand)), 5'-CCAAGTTCA AAGCTGCTGG-3' (SEQ ID NO: 27 in the Sequence Table (antisense strand)); D7Mit44: 5'-TTCTGGCCTCTGT-GAAGTAGTG-3' (SEQ ID NO: 28 in the Sequence Table (sense strand)), 5-GTGAAACCATGGTGCAGATG-3' (SEQ ID NO: 29 in the Sequence Table (antisense strand)); and D4Mit15: 5'-AGGAATACTGAATGTGGACTTTCC-3' (SEQ ID NO: 30 in the Sequence Table (sense strand)), 5'-TC-CCTTGATTAACAGAAGACCTG-3' (SEQ ID NO: 31 in the Sequence Table (antisense strand)).

While the present invention has been particularly shown and described with reference to the methods disclosed herein and as illustrated in the drawings, it is not confined to the details set forth and this invention is intended to cover any modifications and changes as may come within the scope and spirit of the following claims.

Any patent, patent application, publication, or other disclosure material identified in the specification is hereby incorporated by reference herein in its entirety. Any material, or portion thereof, that is said to be incorporated by reference herein, but which conflicts with existing definitions, statements, or other disclosure material set forth herein is only incorporated to the extent that no conflict arises between that incorporated material and the present disclosure material.

What is claimed is:

1. A reprogramming gene-loaded Sendai viral vector comprising Sendai virus genes and reprogramming genes comprising a combination of Oct3/4, Sox2 and Klf4, or a combination of Oct3/4, Sox2, Klf4 and c-Myc, wherein the Sendai virus genes include an NP gene, P/C gene, M gene, F gene, HN gene and L gene, wherein each of the M gene, the F gene and the HN gene is from a Sendai virus strain C1.151-derived gene and wherein at least one of the M gene, the F gene and the HN gene is functionally deleted and the L gene encodes the amino-acid sequence of the L protein in which the amino-acid residue at position 1618 is valine.

2. The Sendai viral vector of claim 1, wherein all of the M gene, the F gene and the HN gene are functionally deleted.

3. The Sendai viral vector of claim 1, wherein the functional deletion in one or more of the M gene, the F gene and the HN gene sequences requires the insertion or substitution of the gene sequences by a reprogramming gene and/or a marker gene.

4. A reprogramming gene-loaded Sendai virus for producing an induced pluripotent stem cell comprising the Sendai viral vector of claim 1.

5. A reprogramming gene-loaded Sendai virus for producing an induced pluripotent stem cell, comprising the Sendai viral vector of claim 1, wherein the Sendai viral vector further comprises a target sequence for a microRNA.

6. The reprogramming gene-loaded Sendai virus of claim 5, wherein the microRNA is expressed in induced pluripotent stem cells.

7. A template vector for preparing a reprogramming gene-loaded Sendai virus, the template vector comprising a cloning vector with Sendai virus genes and reprogramming genes comprising a combination of Oct3/4, Sox2 and Klf4, or a combination of Oct3/4, Sox2, Klf4 and c-Myc, wherein the Sendai virus genes include an NP gene, P/C gene, M gene, F gene, HN gene and L gene, and wherein each of the M gene, the F gene and the HN gene is from the Sendai virus strain C1.151-derived gene and at least one of respective functions of the M gene, the F gene and the HN gene is functionally deleted; and the L gene encodes the amino-acid sequence of the L protein in which the amino-acid residue at position 1618 is valine.

8. The template vector of claim 7, wherein all of the functions of the M gene, the F gene and the HN gene are deleted.

9. The template vector of claim 7, wherein the functional deletion in one or more functions of the M gene, the F gene and the HN gene sequences requires the insertion or substitution of the gene sequences by a reprogramming gene and/or a marker gene.

10. The template vector of claim 7, wherein the cloning vector is a phage vector.

11. The template vector of claim 10, wherein the phage vector is a λphage vector.

12. The template vector of claim 7, wherein the vector comprises DNA.

13. The template vector of claim 7, wherein the vector further comprises a sequence complementary to the target sequence of a microRNA.

14. The template vector of claim 13, wherein the microRNA is expressed in induced pluripotent stem cells.

15. An isolated cell comprising the template vector of claim 7.

16. The cell of claim 15, wherein the functionally-deleted one of the M gene, the F gene and the HN gene is transfected into the cell in the presence or absence of the NP gene, the P gene and the L gene.

17. The cell of claim 15, wherein T7 RNA polymerase is expressed therein.

18. A method of producing a reprogramming gene-loaded Sendai virus comprising the steps of culturing the cell of claim 15; and generating a reprogramming gene-loaded Sendai virus comprising Sendai virus genes and reprogramming genes, wherein the Sendai virus genes include a NP gene, P/C gene, M gene, F gene, HN gene and L gene, and wherein each of the M gene, the F gene and the HN gene is from a Sendai virus strain C1.151-derived gene and at least one of the M gene, the F gene and the HN gene is functionally deleted; and the L gene encodes the amino-acid sequence of the L protein in which the amino-acid residue at position 1618 is valine.

19. The method of claim 18, wherein the template vector further comprises a target sequence for a microRNA.

20. The method of claim 19, wherein the microRNA is expressed in induced pluripotent stem cells.

* * * * *

SEQUENCE LISTING

```
<160> NUMBER OF SEQ ID NOS: 46

<210> SEQ ID NO 1
<211> LENGTH: 2652
<212> TYPE: DNA
<213> ORGANISM: Artificial
<220> FEATURE:
<223> OTHER INFORMATION: Codon-optimized T7 RNA polymerase

<400> SEQUENCE: 1
atgaacacca tcaacattgc caaaaacgat ttcagcgaca ttgagctggc cgccatcccc      60
ttcaataccc tggccgatca ctacgggag cggctggcca gggagcagct ggccctggag     120
cacgagtctt acgagatggg cgaggcccgg ttccggaaaa tgtttgaacg ccagctgaaa     180
gccggagaag tggccgataa cgccgccgcc aagcctctga ttaccaccct gctgcccaag     240
atgattgccc ggattaacga ttggttcgaa gaggtgaaag ccaagagggg caagagacct     300
accgcctttc agtttctgca ggaaatcaaa cctgaagccg tggcctacat caccattaag     360
accacactgg cctgcctgac cagcgccgac aacaccacag tgcaggccgt ggccagcgcc     420
atcggcagag ccatcgagga cgaagccagg ttcgggagga tcagggatct ggaggccaag     480
cacttcaaga aaaatgtgga agagcagctg aataagcggg tgggccacgt gtacaagaag     540
gccttcatgc aggtggtgga agccgatatg ctgagcaaag gcctgctggg cggagaagcc     600
tggagctctt ggcacaagga agatagcatt cacgtgggcg tgagatgtat tgaaatgctg     660
attgagagca cagggatggt gtccctgcac cggcagaacg ccggagtggt gggccaggat     720
agcgagacca tcgagctggc ccccgaatat gccgaggcca ttgccacaag agccggggcc     780
ctggccggga tctctccaat gttccagcca tgcgtggtgc ctccaaagcc atggacaggc     840
atcaccggag ggggctactg ggccaatggg cgcaggcctc tggccctggt gaggacccac     900
agcaaaaagg ccctgatgcg ctacgaggac gtgtacatgc ctgaggtgta caaagccatc     960
aacattgccc agaacaccgc ctggaagatc aacaagaaag tgctggccgt ggccaatgtg    1020
attaccaagt ggaagcactg tccagtggaa gacatccctg ccatcgagcg cgaggaactg    1080
cctatgaagc ccgaggacat tgatatgaac cccgaagccc tgacagcctg gaagagagcc    1140
gccgccgccg tgtaccgcaa agatcgcgcc cggaagtcta ggagaatttc cctggagttc    1200
atgctggagc aggccaataa gttcgccaac cacaaggcca tctggttccc ctacaatatg    1260
gattggcgcg gccgggtgta tgccgtgtcc atgttcaatc cccagggcaa cgacatgacc    1320
```

```
aaaggcctgc tgacactggc caagggcaag cccatcggca aggaaggata ttattggctg    1380
aagatccacg gcgccaattg tgccggggtg gacaaagtgc ctttcctga aaggatcaag    1440 ttcatcgagg agaaccacga gaacatcatg gcctgtgcca aatctcccct ggagaacacc    1500
tggtgggccg aacaggactc tcctttctgc tttctggcct tttgtttcga gtacgccggg    1560
gtgcagcacc acggcctgtc ctacaattgc tctctgcctc tggcctttga cggctcttgc    1620
tccgggattc agcactttag cgccatgctg cgggacgaag tgggcggaag ggccgtgaat    1680
ctgctgccct ccgaaaccgt gcaggatatc tacggcatcg tggccaagaa agtgaatgaa    1740
atcctgcagg ccgatgccat caacgggaca gataacgaag tggtgaccgt gacagacgag    1800
aatacaggcg agattagcga aaaagtgaaa ctggggacca aggccctggc cggccagtgg    1860
ctggcccacg gcgtgacaag gtctgtgacc aagcgcagcg tgatgaccct ggcctacggc    1920
tccaaagagt tcgggttcag acagcaggtg ctggaagaca caatccagcc tgccatcgac    1980
agcggaaagg ggcccatgtt cacccagcca accaggccg ccggctatat ggccaagctg    2040
atctgggaaa gcgtgtctgt gacagtggtg gccgccgtgg aggccatgaa ttggctgaag    2100
agcgccgcca gctgctggc cgccgaagtg aaagacaaga agacaggaga gattctgagg    2160
aagaggtgcg ccgtgcactg ggtgaccca gatggattcc ccgtgtggca ggagtacaag    2220
aaaccaatcc agaccaggct gaatctgatg ttcctgggcc agtttcgcct gcagccaaca    2280
attaacacca caaaggattc cgagattgat gcccacaagc aggaatctgg catcgccccc    2340
aactttgtgc actctcagga tgggtctcac ctgaggaaga ccgtggtgtg ggcccacgaa    2400
aaatatggaa ttgagtcctt tgccctgatt cacgattcct ttggcacaat ccctgccgac    2460
gccgccaacc tgttcaaggc cgtgagagaa accatggtgg ataacctacga atcttgcgat    2520 gtgctggccg atttctacga ccagttcgcc gatcagctgc acgagtccca gctggacaag    2580
atgcccgccc tgcccgccaa aggcaacctg aacctgcggg atattctgga gagcgatttt    2640
gccttcgcct aa                                                       2652

<210> SEQ ID NO 2
<211> LENGTH: 2129
<212> TYPE: DNA
<213> ORGANISM: Artificial
<220> FEATURE:
<223> OTHER INFORMATION: Optimized human Oct4,human Sox2 and a part of
      Sendai virus genome cDNA

<400> SEQUENCE: 2
cctaggttcc ccatggcggg acacctggct tcggatttcg ccttctcgcc ccctccaggt      60
ggtggaggtg atgggccagg ggggccggag ccgggctggg ttgatcctcg gacctggcta     120
agcttccaag gcctcctgg agggccagga atcgggccgg gggttgggcc aggctctgag     180 gtgtgggggga ttcccccatg ccccccgccg tatgagttct gtggggggat ggcgtactgt     240 gggcccagg ttgagtgggg gctagtgccc caaggcggct tggagacctc tcagcctgag     300
ggcgaagcag gagtcgggt ggagagcaac tccgatgggg cctccccgga gcctgcacc     360 gtcaccccctg gtgccgtgaa gctggagaag agaagctgg agcaaaaccc ggaggagtcc     420
caggacatca aagctctgca gaaagaactc gagcaattg ccaagctcct gaagcagaag     480
aggatcaccc tggatatac acaggccgat gtggggctca ccctgggggt tctatttggg     540
aaggtattca gccaaacgac catctgccgc tttgaggctc tgcagcttag cttcaagaac     600
atgtgtaagc tgcggcccctt gctgcagaag tgggtggagg aagctgacaa caatgaaaat     660
```

```
cttcaggaga tatgcaaagc agaaaccctc gtgcaggccc gaaagagaaa gcgaaccagt    720
atcgagaacc gagtgagagg caacctggag aatttgttcc tgcagtgccc gaaacccaca    780
ctgcagcaga tcagccacat cgcccagcag cttgggctcg agaaggatgt ggtccgagtg    840
tggttctgta accggcgcca gaagggcaag cgatcaagca gcgactatgc acaacgagag    900
gattttgagg ctgctgggtc tccttttctca gggggaccag tgtcctttcc tctggcccca    960 gggcccatt ttggtacccc aggctatggg agccctcact tcactgcact gtactcctcg   1020 gtcccttcc ctgaggggga agcctttccc cctgtctccg tcaccactct gggctctccc   1080
atgcattcaa actgaggacg tcagatctgt atataataag aaaaacttag ggtgaaagtg   1140
aggttgcgcg gtattttagc tagcccgcat gtacaacatg atggagacgg agctgaagcc   1200
gccgggcccg cagcaaactt cgggggggcgg cggcggcaac tccaccgcgg cggcggccgg   1260
cggcaaccag aaaaacagcc cggaccgcgt caagcggccc atgaatgcct tcatggtgtg   1320
gtcccgcggg cagcggcgca agatggccca ggagaaaccc aagatgcaca actcggagat   1380
cagcaagcgc ctgggcgccg agtggaaact tttgtcggag acggagaagc ggccgttcat   1440
cgacgaggct aagcggctgc gagcgctgca catgaaggag cacccggatt ataaataccg   1500
gccccggcgg aaaaccaaga cgctcatgaa gaaggataag tacacgctgc ccggcgggct   1560
gctggccccc gcggcaata gcatggcgag cggggtcggg gtgggcgccg gcctgggcgc   1620
gggcgtgaac cagcgcatgg acagttacgc gcacatgaac ggctggagca acggcagcta   1680
cagcatgatg caggaccagc tgggctaccc gcagcacccg ggcctcaatg cgcacggcgc   1740
agcgcagatg cagcccatgc accgctacga cgtgagcgcc ctgcagtaca actccatgac   1800
cagctcgcag acctacatga acggctcgcc cacctacagc atgtcctact cgcagcaggg   1860
cacccctggc atggctcttg gctccatggg ttcggtggtc aagtccgagg ccagctccag   1920 ccccctgtg gttacctctt cctcccactc cagggcgccc tgccaggccg gggacctccg   1980
ggacatgatc agcatgtatc tccccggcgc cgaggtgccg gaacccgccg ccccccagcag   2040 acttcacatg tcccagcact accagagcgg cccggtgccc ggcacggcca ttaacggcac   2100 actgccctc tcacacatgt gagaccggt                                     2129

<210> SEQ ID NO 3
<211> LENGTH: 5851
<212> TYPE: DNA
<213> ORGANISM: Artificial
<220> FEATURE:
<223> OTHER INFORMATION: pMO078

<400> SEQUENCE: 3
gaattcgagt catcccgaga cgcgagttat gtgtttgcaa gacgtgccct aaagtctgca     60
aactatgcag agatgacatt caatgtatgc ggcctgatcc tttctgccga gaaatcttcc    120
gctcgtaagg tagatgagaa caaacaactg ctcaaacaga tccaagagag cgtgaatca    180 ttccgggata tttacaagag attctctgag tatcagaaag aacagaactc attgctgatg    240
tccaacctat ctacacttca tatcatcaca gatagaggtg gcaagactga caacacagac    300
tcccttacaa ggtcccctc cgttttgca aaatcaaaag agaacaagac taaggctacc    360
aggtttgacc catctatgga gaccttagaa gatatgaagt acaaaccgga cctaatccga    420
gaggatgaat ttagagatga gatccgcaac ccggtgtacc aagagaggga cacagaaccc    480
agggcctcaa acgcatcacg tctcttcccc tccaaagaga agcacacaat gcactctctc    540
aggctcgtca tagagagcag tcccctaagc agagctgaga aagcagcata tgtgaaatca    600
```

```
ttatccaagt gcaagacaga ccaagaggtt aaggcagtca tggaactcgt agaagaggac    660
atagagtcac tgaccaacta gatcccgggt gaggcatccc accatcctca gtcacagaga    720
gacccaatct accatcagca tcagccagta aagattaaga aaaacttagg gtgaaagaaa    780
tgcggccgct tggcgccaga atatatgaaa acatttaaca tttctcaaca agatctagaa    840
ttagtagaag tagcgacaga gaagattaca atgctttatg aggataataa acatcatgtg    900
ggagcggcaa ttcgtacgaa aacaggagaa atcatttcgg cagtacatat tgaagcgtat    960
ataggacgag taactgtttg tgcagaagcc attgccattg gtagtgcagt ttcgaatgga   1020
caaaaggatt ttgacacgat tgtagctgtt agacacccct tattctgacga agtagataga   1080 agtattcgag tggtaagtcc ttgtggtatg tgtagggagt tgatttcaga ctatgcacca   1140
gattgttttg tgttaataga aatgaatggc aagttagtca aaactacgat tgaagaactc   1200
attccactca aatatacccg aaattaaaac gcgtcagaga cctgcaacaa tgtctcaagc   1260
agacaccacc tggcagtcgg agccaccggg tcactccttg tcttaaataa gaaaaactta   1320
gggataaagt cccttagatc tagcctaggg ggaccatggt gagcgtgatc aagcccgaga   1380
tgaagatgaa gtacttcatg gacggcagcg tgaacggcca cgagttcacc gtggagggcg   1440
agggcaccgg caagccctac gagggccacc aggagatgac cctgagggtg acaatggcca   1500
agggcggccc catgccccttc agcttcgacc tggtgagcca caccttctgc tacggccaca   1560
ggcccttcac caagtacccc gaggagatcc ccgactactt caagcaggcc ttccccgagg   1620
gcctgagctg ggagaggagc ctccagttcg aggacggcgg cttcgccgcc gtgagcgccc   1680
acatcagcct gaggggcaac tgcttcgagc acaagagcaa gttcgtgggc gtgaacttcc   1740
ccgccgacgg ccccgtgatg cagaaccaga gcagcgactg ggagcccagc accgagaaga   1800
tcaccacctg cgacggcgtg ctgaagggcg acgtgaccat gtacctgaag ctggccggcg   1860
gcggcaacca caagtgccag ttcaagacca cctacaaggc cgccaagaag atcctgaaga   1920
tgccccagag ccacttcatc ggccacaggc tggtgaggaa gaccgagggc aacatcaccg   1980
agctggtgga ggacgccgtg gcccactgct gaagacgtca gatctgtata taataagaaa   2040
aacttagggt gaaagtgagg ttgcgcggta ttttagctag ctgccaccat ggggaactgg   2100
gctgtgaatg aggggctctc cattttgtc attctggttt ggctggggtt gaacgtcttc   2160
ctctttgtct ggtattaccg ggtttatgat attccaccta agttctttta cacaagaaaa   2220
cttcttgggt cagcactggc actggccagg gcccctgcag cctgcctgaa tttcaactgc   2280
atgctgattc tcttgccagt ctgtcgaaat ctgctgtcct tcctcagggg ttccagtgcg   2340
tgctgctcaa caagagttcg aagacaactg gacaggaatc tcaccttttca taaaatggtg   2400 gcatggatga ttgcacttca ctctgcgatt cacaccattg cacatctatt taatgtggaa   2460
tggtgtgtga atgcccgagt caataattct gatccttatt cagtagcact ctctgaactt   2520
ggagacaggc aaaatgaaag ttatctcaat tttgctcgaa agagaataaa gaaccctgaa   2580
ggaggcctgt acctggctgt gaccctgttg gcaggcatca ctggagttgt catcacgctg   2640
tgcctcatat taattatcac ttcctccacc aaaaccatcc ggaggtctta ctttgaagtc   2700
ttttggtaca cacatcatct ctttgtgatc ttcttcattg gccttgccat ccatggagct   2760
gaacgaattg tacgtgggca gaccgcagag agtttggctg tgcataatat aacagtttgt   2820
gaacaaaaaa tctcagaatg ggaaaaaata aaggaatgcc caatccctca gtttgctgga   2880
aaccctccta tgacttggaa atggatagtg ggtcccatgt ttctgtatct ctgtgagagg   2940
ttggtgcggt tttggcgatc tcaacagaag gtggtcatca ccaaggtggt cactcaccct   3000
```

```
ttcaaaacca tcgagctaca gatgaagaag aagggqttca aaatggaagt gggacaatac    3060 attttqtca agtqcccaaa qqtgtccaag ctqgagtgqc acccttttac actgacatcc    3120 gccctgagq aagacttctt tagtatccat atccgcatcg ttggqgactg gacagagggg    3180 ctqttcaatq cttqtqqctq tqataaqcaq qaqtttcaaq atqcqtqqaa actacctaaq    3240 atagcggttg atgggcccctt tggcactgcc agtgaagatg tgttcagcta tgaggtggtg    3300
atgttagtgg gagcagggat tggggtcaca ccctttcgcat ccattctcaa gtcagtctgg    3360
tacaaatatt gcaataacgc caccaatctg aagctcaaaa agatctactt ctactggctg    3420
tgccgggaca cacatgcctt tgagtggttt gcagatctgc tgcaactgct ggagagccag    3480
atgcaggaaa ggaacaatgc cggcttcctc agctacaaca tctacctcac tggctgggat    3540
gagtctcagg ccaatcactt tgctgtgcac catgatgagg agaaagatgt gatcacaggc    3600
ctgaaacaaa agactttgta tggacggccc aactgggata tgaattcaa gacaattgca    3660 agtcaacacc ctaataccag aataggagtt ttcctctgtg gacctgaagc cttggctgaa    3720
accctgagta acaaagcat ctccaactct gagtctggcc ctcggggagt gcatttcatt    3780
ttcaacaagg aaaacttcta acaccggtgt cggctttgct gacactagag tcatctccga    3840
acatccacaa tatctctcag tctcttacgt ctctcacagt attaagaaaa acccagggtg    3900
aatgggaagc ttgccatagg tcatggatgg gcaggagtcc tcccaaaacc cttctgacat    3960
actctatcca gaatgccacc tgaactctcc catagtcagg gggaagatag cacagttgca    4020
cgtcttgtta gatgtgaacc agccctacag actaaaggac gacagcataa taaatattac    4080
aaagcacaaa attaggaacg gaggattgtc ccctcgtcaa attaagatca ggtctctggg    4140
taaggctctt caacgcacaa taaggattt agaccgatac accttgaac cgtacccaac    4200 ctactctcag gaattactta ggcttgatat accagagata tgtgacaaaa tccgatccgt    4260
cttcgcggtc tcggatcggc tgaccaggga gttatctagt gggttccagg atctttggtt    4320
gaatatcttc aagcaactag gcaatataga aggaagagag gggtacgatc cgttgcagga    4380
tatcggcacc atcccggaga taactgataa atacagcagg aatagatggt ataggccatt    4440
cctaacttgg ttcagcatca aatatgacat gcggtggatg cagaagacca gaccgggggg    4500 accctcgat acctctaatt cacataacct cctagaatgc aaatcataca ctctagtaac    4560
atacggagat cttatcatga tactgaacaa gttgacattg acagggtata tcctaacccc    4620
tgagctggtc ttgatgtatt gtgatgttgt agagggaagg tggaatatgt ctgctgcagg    4680
gcatctagat aagaagtcca ttgggataac aagcaaaggt gaggaattat gggaactagt    4740
ggattccctc ttctcaagtc ttggagagga aatatacaat gtcatcgcac tattggagcc    4800
cctatcactt gctctcatac aactaaatga tccagttata cctctacgtg ggcattttat    4860
gaggcatgtg ttgacagagc tacaggctgt tttaacaagt agggacgtgt acacagatgc    4920
tgaagcagac actattgtgg agtcgttact cgccattttc catggaacct ctattgatga    4980
gaaagcagag atcttttcct tctttaggac atttggccac cccagcttag aggctgtcac    5040
tgccgccgac aagqtaaggg cccatatgta tgcacaaaag gcaataaagc ttaagaccct    5100
atacgagtgt catgcagttt tttgcactat catcataaat gggtatagag agaggcatgg    5160
cggacagtgg cccccctgtg acttccctga tcacgtgtgt ctagaactaa ggaacgctca    5220
agggtccaat acggcaatct cttatgaatg tgctgtagac aactatacaa gtttcatagg    5280
cttcaagttt cggaagttta tagaaccaca actagatgaa gatctcacaa tatatatgaa    5340
agacaaagca ctatccccca ggaaggaggc atgggactct gtatacccgg atagtaatct    5400
```

```
gtactataaa gcccagaat ctgaagagac ccggcggctt attgaagtgt tcataaatga   5460
tgagaatttc aacccagaag aaattatcaa ttatgtggag tcaggagatt ggttgaaaga   5520
cgagaagttc aacatctcgt acagtctcaa agagaaagag atcaagcaag agggtcgtct   5580
attcgcaaaa atgacttata agatgcgagc cgtacaggtg ctggcagaga cactactggc   5640
taaaggaata ggagagctgt tcagcgaaaa tgggatggtt aaaggagaga tagacctact   5700
taaaagattg actactcttt ctgtctcagg agtccccagg actgattcag tgtacaataa   5760
ctctaaatca tcagagaaga gaaacgaagg catgaaaaag aagaactctg ggggtactg    5820 ggacgaaaag aagaggtcca gacatgaatt c                                  5851
```

<210> SEQ ID NO 4
<211> LENGTH: 1478
<212> TYPE: DNA
<213> ORGANISM: Artificial
<220> FEATURE:
<223> OTHER INFORMATION: Optimized human Klf4 and a part of Sendai virus genome cDNA

<400> SEQUENCE: 4

```
gctagcacct aggtctgaca tggctgtcag cgacgcgctg ctcccatctt tctccacgtt     60
cgcgtctggc ccggcgggaa gggagaagac actgcgtcaa gcaggtgccc gaataaccg    120 ctggcgggag gagctctccc acatgaagcg acttcccca gtgcttcccg ccgcccta      180 tgacctggcg gcggcgaccg tggccacaga cctggagagc ggcggagccg gtgcggcttg   240
cggcggtagc aacctggcgc ccctacctcg gagagagacc gaggagttca acgatctcct   300
ggacctggac tttattctct ccaattcgct gacccatcct ccggagtcag tggccgccac   360
cgtgtcctcg tcagcgtcag cctcctcttc gtcgtcgccg tcgagcagcg gccctgccag   420
cgcgccctcc acctgcagct tcacctatcc gatccgggcc gggaacgacc cgggcgtggc   480
gccgggcggc acgggcggag gcctcctcta tggcagggag tccgctcccc ctccgacggc   540
tcccttcaac ctggcggaca tcaacgacgt gagcccctcg ggcggcttcg tggccgagct   600
cctgcggcca gaattggacc cggtgtacat tccgccgcag cagccgcagc gccaggtgg   660 cgggctgatg ggcaagttcg tgctgaaggc gtcgctgagc gcccctggca gcgagtacgg   720
cagcccgtcg gtcatcagcg tcagcaaagg cagcccctgac ggcagccacc cggtggtggt   780
ggcgccctac aacggcgggc cgccgcgcac gtgcccaag atcaagcagg aggcggtctc   840
ttcgtgcacc cacttgggcg ctggaccccc tctcagcaat ggccaccggc cggctgcaca   900
cgacttcccc ctggggcggc agctccccag caggactacc ccgaccctgg gtcttgagga   960
agtgctgagc agcagggact gtcaccctgc cctgccgctt cctccggct tccatcccca   1020 cccgggcc aattacccat ccttcctgcc cgatcagatg cagccgcaag tcccgccgct   1080 ccattacca gagctcatgc cacccggttc ctgcatgcca gaggagccca agccaaagag   1140
gggaagacga tcgtggcccc gaaaagggac cgccaccac acttgtgatt acgcgggctg   1200
cggcaaaacc tacacaaaga gttcccatct caaggcacac ctgcgaaccc acacaggtga   1260
gaaaccttac cactgtgact gggacggctg tggatggaaa ttcgcccgct cagatgaact   1320
gaccaggcac taccgtaaac acacggggca ccgcccgttc cagtgccaaa atgcgaccg   1380 agcatttttcc aggtcggacc acctcgcctt acacatgaag aggcatttttt aaagacgtcg   1440 attaagaaaa acttagggtg aaagttcatc gcggccgc                          1478
```

<210> SEQ ID NO 5
<211> LENGTH: 3696

<212> TYPE: DNA
<213> ORGANISM: Artificial
<220> FEATURE:
<223> OTHER INFORMATION: A part of Sendai virus genome cDNA : XhoI-
    T7pro-SevcDNA-NheI-NotI

<400> SEQUENCE: 5

| | | | | | |
|---|---|---|---|---|---|
| ctcgagtaat | acgactcact | atagggacca | aacaagagaa | gaaacatgta | tggaatatat | 60 |
| aatgaagtta | gacaggattt | tagggtcaaa | gtatccaccc | tgaggagcag | gttccagatc | 120 |
| cttttctttg | ctgccaaagt | tcacgatggc | cgggttgttg | agcaccttcg | atacatttag | 180 |
| ctctaggagg | agcgaaagta | ttaataagtc | gggaggaggt | gctgttatcc | ccggccagag | 240 |
| gagcacagtc | tcagtgttca | tactaggccc | aagtgtgact | gatgatgcag | acaagttatt | 300 |
| cattgcaaca | accttcctag | ctcactcatt | ggacacagat | aagcagcact | ctcagagagg | 360 |
| agggttcctc | gtctctctgc | ttgccatggc | ttacagtagt | ccagaattgt | acttgacaac | 420 |
| aaacggagta | aacgccgatg | tcaaatatgt | gatctacaac | atagagaaag | accctaagag | 480 |
| gacgaagaca | gacggattca | ttgtgaagac | gagagatatg | aatatgaga | ggaccacaga | 540 |
| atggctgttt | ggacctatgg | tcaacaagag | cccactcttc | cagggtcaac | gggatgctgc | 600 |
| agaccctgac | acactccttc | aaatctatgg | gtatcctgca | tgcctaggag | caataattgt | 660 |
| ccaagtctgg | attgtgctgg | tgaaggccat | cacaagcagc | gccggcttaa | ggaaagggtt | 720 |
| cttcaacagg | ttagaggcgt | tcagacaaga | cggcaccgtg | aaaggtgcct | tagttttcac | 780 |
| tggggagaca | gttgagggga | taggctcggt | tatgagatct | cagcaaagcc | ttgtatctct | 840 |
| catggttgag | acccttgtga | ctatgaatac | tgcaagatct | gatctcacca | cattagagaa | 900 |
| gaacatccag | atcgttggga | actacatccg | agatgcaggg | ctggcttcct | tcatgaacac | 960 |
| tattaaatat | ggggtggaga | caaagatggc | agctctaacg | ttgtcaaacc | tgaggcccga | 1020 |
| tattaataag | cttagaagcc | tcatagacac | ctacctgtca | aaaggcccca | gagctcccct | 1080 |
| tatctgtatc | ctcaaggacc | ctgttcatgg | tgaatttgct | ccaggcaatt | atcctgcact | 1140 |
| atggagttac | gccatgggag | tcgccgtcgt | cacagaacaag | tcaatgcagc | agtacgtcac | 1200 |
| agggaggaca | taccttgata | tggaaatgtt | cttactagga | caagccgtgg | caaaggatgc | 1260 |
| tgaatcgaag | atcagcagtg | ccttggaaga | tgagttagga | gtgacggata | cagccaagga | 1320 |
| gaggctcaga | catcatctgg | caaacttgtc | cggtgggat | ggtgcttacc | acaaaccaac | 1380 |
| aggcggtggt | gcaattgagg | tagctctaga | caatgccgat | atcgacctgg | aaacagaagc | 1440 |
| tcatgcggac | caggacgcta | ggggttgggg | tggagatagt | ggtgaaagat | gggcacgtca | 1500 |
| ggtgagtggt | ggccactttg | tcacactaca | tggggctgaa | cggttagagg | aggaaaccaa | 1560 |
| tgatgaggat | gtatcagaca | tagagagaag | aatagccatg | agactcgcag | agagacggca | 1620 |
| agaggattct | gcaacccatg | gagatgaagg | ccgcaataac | ggtgttgatc | acgaagaaga | 1680 |
| tgacgatgcc | gcagcagcag | ctgggatagg | aggaatctag | gatcatacga | ggcctcaagg | 1740 |
| tacttgatcc | gcagtaagaa | aaacttaggg | tgaaagttca | tccaccgatc | ggctcaggca | 1800 |
| aggccacacc | caaccccacc | gaccacaccc | agcagtcgag | acagccacgg | cttcggctac | 1860 |
| acttaccgca | tggatcaaga | tgccttcatt | cttaaagaag | attctgaagt | tgagaggaag | 1920 |
| gcgccaggag | gacgagagtc | gctctcggat | gttatcggat | tcctcgatgc | tgtcctgtcg | 1980 |
| aatgaaccaa | ctgacatcgg | aggggacaga | agctggctcc | acaacaccat | caacactccc | 2040 |
| caaggaccag | gctctgctca | tagagccaaa | agtgagggcg | aaggagaagt | ctcaacaccg | 2100 |
| tcgacccaag | ataatcgatc | aggtgaggag | agtagagtct | ctgggagaac | aagcaagcca | 2160 |

```
gaggcagaag cacatgctgg aaaccttgat aaacaaaata tacactgggc ctttaggdga    2220
agaactggta caaactctgt atctcaggat ctggacgatg gaggagactc cggaatcctt    2280
gaaaatcctc caaatgagag aggatatccg agatcaggta ttgaagatga aaacagagag    2340
atggctgcgc accctgataa aggggagaa gaccaagctg aaggacttcc agaagaggta    2400
cgaggaggta catccctacc tgatgaagga aaggtggag caagtaataa tggaagaagc    2460
atggagcctg gcagctcaca tagtgcaaga gtaactgggg tcctggtgat tcctagcccc    2520
gaacttgaag aggctgtgct acggaggaac aaaagaagac ctaccaacag tgggtccaaa    2580
cctcttactc cagcaaccgt gcctggcacc cggtccccac cgctgaatcg ttacaacagc    2640
acagggtcac caccaggaaa accccatct acacaggatg agcacatcaa ctctggggac    2700 accccgccg tcagggtcaa agaccggaaa ccatcaatag ggactcgctc tgtctcagat    2760
tgtccagcca acggccgccc aatccatccg ggtatagaga ccgactcaac aaaaaagggc    2820
ataggagaga acacatcatc tatgaaagat atggctacat tgttgacgag tcttggtgta    2880
atccagtctg ctcaagaatt cgagtcatcc cgagacgcga gttatgtgtt tgcaagacgt    2940
gccctaaagt ctgcaaacta tgcagagatg acattcaatg tatgcggcct gatcctttct    3000
gccgagaaat cttccgctcg taaggtagat gagaacaaac aactgctcaa acagatccaa    3060
gagagcgtgg aatcattccg ggatatttac aagagattct ctgagtatca gaagaacag    3120 aactcattgc tgatgtccaa cctatctaca cttcatatca tcacagatag aggtggcaag    3180
actgacaaca cagactccct tacaaggtcc cctccgtttt ttgcaaaatc aaaagagaac    3240
aagactaagg ctaccaggtt tgacccatct atggagacct tagaagatat gaagtacaaa    3300
ccggacctaa tccgagagga tgaatttaga gatgagatcc gcaacccggt gtaccaagag    3360
agggacacag aacccagggc ctcaaacgca tcacgtctct tcccctccaa agagaagccc    3420
acaatgcact ctctcaggct cgtcatagag agcagtcccc taagcagagc tgagaaagca    3480
gcatatgtga atcattatc caagtgcaag acagaccaag aggttaaggc agtcatggaa    3540
ctcgtagaag aggacataga gtcactgacc aactagatcc cgggtgaggc atcccaccat    3600
cctcagtcac agagagaccc aatctaccat cagcatcagc cagtaaagat taagaaaaac    3660
ttagggtgaa agaaatttca ccgctagcgc ggccgc                            3696
```

<210> SEQ ID NO 6
<211> LENGTH: 14760
<212> TYPE: DNA
<213> ORGANISM: Artificial
<220> FEATURE:
<223> OTHER INFORMATION: Template cDNA for SeVp(Mp+Klf4,delta-M::Bsr, delta-F::Oct4,delta-HN::Sox2)

<400> SEQUENCE: 6

```
accaaacaag agaagaaaca tgtatggaat atataatgaa gttagacagg attttagggt      60
caaagtatcc accctgagga gcaggttcca gatcctttc tttgctgcca aagttcacga     120
tggccgggtt gttgagcacc ttcgatacat ttagctctag gaggagcgaa agtattaata     180
agtcggggag aggtgctgtt atccccggcc agaggagcac agtctcagtg ttcatactag     240
gcccaagtgt gactgatgat gcagacaagt tattcattgc aacaaccttc ctagctcact     300
cattggacac agataagcag cactctcaga gggagggtt cctcgtctct ctgcttgcca     360
tggcttacag tagtccagaa ttgtacttga caacaaacgg agtaaacgcc gatgtcaaat     420
atgtgatcta caacatagag aaagacccta gaggacgaa gacagacgga ttcattgtga     480
agacgagaga tatggaatat gagaggacca cagaatggct gtttggacct atggtcaaca     540
```

```
agagcccact cttccagggt caacgggatg ctgcagaccc tgacacactc cttcaaatct    600
atgggtatcc tgcatgccta ggagcaataa ttgtccaagt ctggattgtg ctggtgaagg    660
ccatcacaag cagcgccggc ttaaggaaag ggttcttcaa caggttagag gcgttcagac    720
aagacggcac cgtgaaaggt gccttagttt tcactgggga gacagttgag gggataggct    780
cggttatgag atctcagcaa agccttgtat ctctcatggt tgagacccct gtgactatga    840
atactgcaag atctgatctc accacattag agaagaacat ccagatcgtt gggaactaca    900
tccgagatgc agggctggct tccttcatga acactattaa atatggggtg gagacaaaga    960
tggcagctct aacgttgtca aacctgaggc ccgatattaa taagcttaga agcctcatag   1020
acacctacct gtcaaaaggc cccagagctc cctttatctg tatcctcaag gaccctgttc   1080
atggtgaatt tgctccaggc aattatcctg cactatggag ttacgccatg ggagtcgccg   1140
tcgtacagaa caagtcaatg cagcagtacg tcacagggag gacatacctt gatatggaaa   1200
tgttcttact aggacaagcc gtggcaaagg atgctgaatc gaagatcagc agtgccttgg   1260
aagatgagtt aggagtgacg atacagcca aggagaggct cagacatcat ctggcaaact   1320
tgtccggtgg ggatggtgct taccacaaac caacaggcgg tggtgcaatt gaggtagctc   1380
tagacaatgc cgatatcgac ctggaaacag aagctcatgc ggaccaggac gctagggtt   1440 ggggtggaga tagtggtgaa agatgggcac gtcaggtgag tggtggccac tttgtcacac   1500
tacatggggc tgaacggtta gaggaggaaa ccaatgatga ggatgtatca gacatagaga   1560
gaagaatagc catgagactc gcagagagac ggcaagagga ttctgcaacc catggagatg   1620
aaggccgcaa taacggtgtt gatcacgaag aagatgacga tgccgcagca gcagctggga   1680
taggaggaat ctaggatcat acgaggcctc aaggtacttg atccgcagta agaaaaactt   1740
agggtgaaag ttcatccacc gatcggctca ggcaaggcca cacccaaccc caccgaccac   1800
acccagcagt cgagacagcc acggcttcgg ctacacttac cgcatggatc aagatgcctt   1860
cattcttaaa gaagattctg aagttgagag gaaggcgcca ggaggacgag agtcgctctc   1920
ggatgttatc ggattcctcg atgctgtcct gtcgaatgaa ccaactgaca tcggagggga   1980
cagaagctgg ctccacaaca ccatcaacac tccccaagga ccaggctctg ctcatagagc   2040
caaaagtgag ggcgaaggag aagtctcaac accgtcgacc caagataatc gatcaggtga   2100
ggagagtaga gtctctggga gaacaagcaa gccagaggca gaagcacatg ctggaaacct   2160
tgataaacaa aatatacact gggcctttag gggaagaact ggtacaaact ctgtatctca   2220
ggatctggac gatggaggag actccggaat ccttgaaaat cctccaaatg agagaggata   2280
tccgagatca ggtattgaag atgaaaacag agagatggct cgcaccctg ataagagggg   2340 agaagaccaa gctgaaggac ttccagaaga ggtacgagga ggtacatccc tacctgatga   2400
aggagaaggt ggagcaagta ataatggaag aagcatggag cctggcagct cacatagtgc   2460
aagagtaact ggggtcctgg tgattcctag ccccgaactt gaagaggctg tgctacggag   2520
gaacaaaaga agacctacca acagtgggtc caaacctctt actccagcaa ccgtgcctgg   2580
cacccggtcc ccaccgctga atcgttacaa cagcacaggg tcaccaccag gaaaaccccc   2640
atctacacag gatgagcaca tcaactctgg ggacaccccc gccgtcaggg tcaaagaccg   2700
gaaaccatca ataggggactc gctctgtctc agattgtcca gccaacggcc gcccaatcca   2760
tccgggtata gagaccgact caacaaaaaa gggcatagga gagaacacat catctatgaa   2820
agatatggct acattgttga cgagtcttgg tgtaatccag tctgctcaag aattcgagtc   2880
atcccgagac gcgagttatg tgtttgcaag acgtgcccta aagtctgcaa actatgcaga   2940
```

```
gatgacattc aatgtatgcg gcctgatcct ttctgccgag aaatcttccg ctcgtaaggt    3000
agatgagaac aaacaactgc tcaaacagat ccaagagagc gtggaatcat tccgggatat    3060
ttacaagaga ttctctgagt atcagaaaga acagaactca ttgctgatgt ccaacctatc    3120
tacacttcat atcatcacag atagaggtgg caagactgac aacacagact cccttacaag    3180 gtcccctcc gttttgcaa aatcaaaaga gaacaagact aaggctacca ggtttgaccc       3240
atctatggag accttagaag atatgaagta caaaccggac ctaatccgag aggatgaatt    3300
tagagatgag atccgcaacc cggtgtacca agagagggac acagaaccca gggcctcaaa    3360
cgcatcacgt ctcttcccct ccaaagagaa gcccacaatg cactctctca ggctcgtcat    3420
agagagcagt cccctaagca gagctgagaa agcagcatat gtgaaatcat tatccaagtg    3480
caagacagac caagaggtta aggcagtcat ggaactcgta aagaggaca tagagtcact      3540 gaccaactag atcccgggtg aggcatccca ccatcctcag tcacagagag acccaatcta    3600
ccatcagcat cagccagtaa agattaagaa aaacttaggg tgaaagaaat ttcaccgcta    3660
gcacctaggt ctgacatggc tgtcagcgac gcgctgctcc catctttctc cacgttcgcg    3720
tctggcccgg cgggaaggga gaagacactg cgtcaagcag gtgccccgaa taaccgctgg    3780
cgggaggagc tctcccacat gaagcgactt ccccccagtgc ttcccggccg ccctatgac     3840 ctggcggcg cgaccgtggc cacagacctg gagagcggcg gagccggtgc ggcttgcggc      3900
ggtagcaacc tggcgcccct acctcggaga gagaccgagg agttcaacga tctcctggac    3960
ctggacttta ttctctccaa ttcgctgacc catcctccgg agtcagtggc cgccaccgtg    4020
tcctcgtcag cgtcagcctc ctcttcgtcg tcgccgtcga gcagcggccc tgccagcgcg    4080
ccctccacct gcagcttcac ctatccgatc cgggccggga acgacccggg cgtggcgccg    4140
ggcggcacgg gcggaggcct cctctatggc agggagtccg ctccccctcc gacggctccc    4200
ttcaacctgg cggacatcaa cgacgtgagc ccctcgggcg gcttcgtggc cgagctcctg    4260
cggccagaat tggacccggt gtacattccg ccgcagcagc cgcagccgcc aggtggcggg    4320
ctgatgggca agttcgtgct gaaggcgtcg ctgagcgccc ctggcagcga gtacggcagc    4380
ccgtcggtca tcagcgtcag caaaggcagc cctgacggca gccacccggt ggtggtggcg    4440
ccctacaacg gcgggccgcc gcgcacgtgc cccaagatca agcaggaggc ggtctcttcg    4500
tgcacccact gggcgctgg accccctctc agcaatggcc accggccggc tgcacacgac     4560 ttcccctgg ggcggcagct ccccagcagg actaccccga ccctgggtct tgaggaagtg     4620
ctgagcagca gggactgtca ccctgccctg ccgcttcctc ccggcttcca tccccacccg    4680
gggcccaatt acccatcctt cctgcccgat cagatgcagc cgcaagtccc gccgctccat    4740
taccaagagc tcatgccacc cggttcctgc atgccagagg agcccaagcc aaagagggga    4800
agacgatcgt ggccccggaa aaggaccgcc acccacactt gtgattacgc gggctgcggc    4860
aaaacctaca caaagagttc ccatctcaag gcacacctgc gaacccacac aggtgagaaa    4920
ccttaccact gtgactggga cggctgtgga tggaaattcg cccgctcaga tgaactgacc    4980
aggcactacc gtaaacacac ggggcaccgc ccgttccagt gccaaaaatg cgaccgagca    5040
ttttccaggt cggaccacct cgccttacac atgaagaggc attttaaag acgtcgatta      5100 agaaaaactt agggtgaaag ttcatcgcgg ccgcttggcg ccagaatata tgaaaacatt    5160
taacatttct caacaagatc tagaattagt agaagtagcg acagagaaga ttacaatgct    5220
ttatgaggat aataaacatc atgtgggagc ggcaattcgt acgaaaacag agaaatcat      5280 ttcggcagta catattgaag cgtatatagg acgagtaact gtttgtgcag aagccattgc    5340
```

```
cattggtagt gcagtttcga atggacaaaa ggattttgac acgattgtag ctgttagaca      5400
cccttattct gacgaagtag atagaagtat tcgagtggta agtccttgtg gtatgtgtag      5460
ggagttgatt tcagactatg caccagattg ttttgtgtta atagaaatga atggcaagtt      5520
agtcaaaact acgattgaag aactcattcc actcaaatat acccgaaatt aaaacgcgtc      5580
agagacctgc aacaatgtct caagcagaca ccacctggca gtcggagcca ccgggtcact      5640
ccttgtctta aataagaaaa acttagggat aaagtccctt agatctagcc taggttcccc      5700
atggcgggac acctggcttc ggatttcgcc ttctcgcccc ctccaggtgg tggaggtgat      5760
gggccagggg ggccggagcc gggctgggtt gatcctcgga cctggctaag cttccaaggc      5820
cctcctggag ggccaggaat cgggccgggg gttgggccag gctctgaggt gtggggatt      5880 cccccatgcc ccccgccgta tgagttctgt gggggatgg cgtactgtgg gccccaggtt      5940 ggagtgggc tagtgcccca aggcggcttg gagacctctc agcctgaggg cgaagcagga      6000 gtcgggtgg agagcaactc cgatgggcc tccccggagc cctgcaccgt caccctggt       6060 gccgtgaagc tggagaagga gaagctggag caaacccgg aggagtccca ggacatcaaa      6120
gctctgcaga aagaactcga gcaatttgcc aagctcctga agcagaagag gatcaccctg      6180
ggatatacac aggccgatgt ggggctcacc ctgggggttc tatttgggaa ggtattcagc      6240
caaacgacca tctgccgctt tgaggctctg cagcttagct tcaagaacat gtgtaagctg      6300 cggccccttgc tgcagaagtg ggtggaggaa gctgacaaca atgaaaatct tcaggagata      6360
tgcaaagcag aaaccctcgt gcaggcccga aagagaaagc gaaccagtat cgagaaccga      6420
gtgagaggca acctggagaa tttgttcctg cagtgcccga acccacact gcagcagatc      6480 agccacatcg cccagcagct tgggctcgag aaggatgtgg tccgagtgtg gttctgtaac      6540
cggcgccaga agggcaagcg atcaagcagc gactatgcac aacgagagga ttttgaggct      6600
gctgggtctc ctttctcagg gggaccagtg tcctttcctc tggccccagg gccccatttt      6660 ggtacccag gctatgggag ccctcacttc actgcactgt actcctcggt cccttccct      6720 gagggggaag cctttccccc tgtctccgtc accactctgg gctctcccat gcattcaaac      6780
tgaggacgtc agatctgtat ataataagaa aaacttaggg tgaaagtgag gttgcgcggt      6840
attttagcta gcccgcatgt acaacatgat ggagacggag ctgaagccgc cgggcccgca      6900
gcaaacttcg gggggcggcg gcggcaactc caccgcggcg gcggccggcg gcaaccagaa      6960
aaacagcccg accgcgtca gcggcccat gaatgccttc atggtgtggt cccgcgggca      7020
gcggcgcaag atgcccagg agaaccccaa gatgcacaac tcggagatca gcaagcgcct      7080
gggcgccgag tggaaacttt tgtcggagac ggagaagcgg ccgttcatcg acgaggctaa      7140
gcggctgcga gcgctgcaca tgaaggagca cccggattat aaataccggc cccggcggaa      7200
aaccaagacg ctcatgaaga aggataagta cacgctgccc ggcgggctgc tggccccgg       7260 cggcaatagc atggcgagcg gggtcgggt gggcgccggc ctgggcgcgg gcgtgaacca      7320
gcgcatggac agttacgcgc acatgaacgg ctggagcaac ggcagctaca gcatgatgca      7380
ggaccagctg ggctacccgc agcacccggg cctcaatgcg cacggcgcag cgcagatgca      7440
gcccatgcac cgctacgacg tgagcgccct gcagtacaac tccatgacca gctcgcagac      7500
ctacatgaac ggctcgccca cctacagcat gtcctactcg cagcagggca ccctggcat       7560 ggctcttggc tccatggggt tcggtggtcaa gtccgaggcc agctccagcc cctgtggt       7620 tacctcttcc tcccactcca gggcgccctg ccaggccggg gacctccggg acatgatcag      7680
catgtatctc cccggcgccg aggtgccgga acccgccgcc ccagcagac ttcacatgtc      7740
```

```
ccagcactac cagagcggcc cggtgcccgg cacggccatt aacggcacac tgcccctctc   7800
acacatgtga gaccggtgtc ggctttgctg acactagagt catctccgaa catccacaat   7860
atctctcagt ctcttacgtc tctcacagta ttaagaaaaa cccagggtga atgggaagct   7920
tgccataggt catggatggg caggagtcct cccaaaaccc ttctgacata ctctatccag   7980
aatgccacct gaactctccc atagtcaggg ggaagatagc acagttgcac gtcttgttag   8040
atgtgaacca gccctacaga ctaaaggacg acagcataat aaatattaca aagcacaaaa   8100
ttaggaacgg aggattgtcc cctcgtcaaa ttaagatcag gtctctgggt aaggctcttc   8160
aacgcacaat aaaggattta gaccgataca cctttgaacc gtacccaacc tactctcagg   8220
aattacttag gcttgatata ccagagatat gtgacaaaat ccgatccgtc ttcgcggtct   8280
cggatcggct gaccagggag ttatctagtg ggttccagga tctttggttg aatatcttca   8340
agcaactagg caatatagaa ggaagagagg ggtacgatcc gttgcaggat atcggcacca   8400
tcccggagat aactgataaa tacagcagga atagatggta taggccattc ctaacttggt   8460
tcagcatcaa atatgacatg cggtggatgc agaagaccag accgggggga cccctcgata   8520
cctctaattc acataacctc ctagaatgca aatcatacac tctagtaaca tacggagatc   8580
ttatcatgat actgaacaag ttgacattga cagggtatat cctaaccccct gagctggtct   8640 tgatgtattg tgatgttgta gagggaaggt ggaatatgtc tgctgcaggg catctagata   8700
agaagtccat tgggataaca agcaaggtg aggaattatg ggaactagtg gattccctct   8760
tctcaagtct tggagaggaa atatacaatg tcatcgcact attggagccc ctatcacttg   8820
ctctcataca actaaatgat ccagttatac ctctacgtgg ggcatttatg aggcatgtgt   8880
tgacagagct acaggctgtt ttaacaagta gggacgtgta cacagatgct gaagcagaca   8940
ctattgtgga gtcgttactc gccatttttcc atggaacctc tattgatgag aaagcagaga   9000
tcttttcctt ctttaggaca tttggccacc ccagcttaga ggctgtcact gccgccgaca   9060
aggtaagggc ccatatgtat gcacaaaagg caataaagct taagacccta tacgagtgtc   9120
atgcagtttt ttgcactatc atcataaatg ggtatagaga gaggcatggc ggacagtggc   9180 cccctgtga cttccctgat cacgtgtgtc tagaactaag gaacgctcaa gggtccaata   9240
cggcaatctc ttatgaatgt gctgtagaca actatacaag tttcataggc ttcaagtttc   9300
ggaagtttat agaaccacaa ctagatgaag atctcacaat atatatgaaa gacaaagcac   9360
tatcccccag gaaggaggca tgggactctg tatacccgga tagtaatctg tactataaag   9420
ccccagaatc tgaagagacc cggcggctta ttgaagtgtt cataaatgat gagaatttca   9480
acccagaaga aattatcaat tatgtggagt caggagattg gttgaaagac gagaagttca   9540
acatctcgta cagtctcaaa gagaaagaga tcaagcaaga gggtcgtcta ttcgcaaaaa   9600
tgacttataa gatgcgagcc gtacaggtgc tggcagagac actactggct aaaggaatag   9660
gagagctgtt cagcgaaaat gggatggtta aggagagat agacctactt aaaagattga   9720
ctactctttc tgtctcagga gtccccagga ctgattcagt gtacaataac tctaaatcat   9780
cagagaagag aaacgaaggc atgaaaaaga agaactctgg ggggtactgg gacgaaaaga   9840
agaggtccag acatgaattc aaggcaacag attcatcaac agacggctat gaaacgttaa   9900
gttgcttcct cacaacagac ctcaagaaat actgcttaaa ctggagattt gaaagtactg   9960
cattgtttgg tcagagatgc aacgagatat ttggcttcaa gaccttcttt aactggatgc  10020
atccagtcct tgaaaggtgt acaatatatg ttggggatcc ttactgtcca gtcgccgacc  10080
ggatgcatcg acaactccag gatcatgcag actctggcat tttcatacat aatcctaggg  10140
```

```
ggggcataga aggttactgc cagaagctgt ggaccttaat ctcaatcagt gcaatccacc   10200
tagcagctgt gagagtgggt gtcagggtct ctgcaatggt tcagggtgac aatcaagcta   10260
tagccgtgac atcaagagta cctgtagctc agacttacaa gcagaagaaa aatcatgtct   10320
ataaggagat caccaaatat tttggtgctc taagacacgt catgtttgat gtagggcacg   10380
agctaaaatt gaacgagacc atcattagta gcaagatgtt tgtctatagt aaaagaatat   10440
actatgatgg gaagatttta ccacagtgcc tgaaagcctt gaccaggtgt gtattctggt   10500
ccgagacact ggtagatgaa aacagatctg cttgttcgaa catctcaaca tccatagcaa   10560
aagctatcga aaatgggtat tctcctatac taggctactg cattgcgttg tataagacct   10620
gtcagcaggt gtgcatatca ctagggatga ctataaatcc aactatcagc ccgaccgtaa   10680
gagatcaata ctttaagggt aagaattggc tgagatgtgc agtgttgatt ccagcaaatg   10740
ttggaggatt caactacatg tctacatcta gatgctttgt tagaaatatt ggagaccccg   10800
cagtagcagc cctagctgat ctcaaaagat tcatcagagc ggatctgtta gacaagcagg   10860
tactatacag ggtcatgaat caagaacccg gtgactctag ctttctagat tgggcttcag   10920
acccttattc atgtaacctc ccgcattctc agagtataac tacgattata agaatatca   10980 ctgctagatc tgtgctgcag gaatccccga atcctctact gtctggtctc ttcaccgaga   11040
ctagtggaga agaggatctc aacctggcct cgttccttat ggaccggaaa gtcatcctgc   11100
cgagagtggc tcatgagatc ctgggtaatt ccttaactgg agttagggag gcgattgcag   11160
ggatgcttga tacgaccaag tctctagtga gatccagcgt taagaaagga ggattatcat   11220
atgggatatt gaggaggctt gtcaattatg atctattgca gtacgagaca ctgactagaa   11280
ctctcaggaa accggtgaaa gacaacatcg aatatgagta tatgtgttca gttgagctag   11340
ctgtcggtct aaggcagaaa atgtggatcc acctaactta cgggagaccc atacatgggc   11400
tagaaacacc agacccttta gagctcttga ggggaacatt tatcgaaggt tcagaggtgt   11460
gcaagctttg caggtctgag ggagcagacc ccatctatac atggttctat ctccctgaca   11520
atatagacct ggacacgctt acaaacggat gtccggctat aagaatcccc tattttggat   11580
cagccactga tgaaaggtcg gaagcccaac tcgggtatgt aagaaatcta agcaaacccg   11640
caaaggctgc catccggata gctatggtgt atacgtgggc ctacgggact gatgagatat   11700
cgtggatgga agccgctctt atagcccaaa caagagctaa tctgagctta gagaatctaa   11760
agctgctgac tcctgtttca acctccacta atctatctca taggttgaaa gatacggcaa   11820
cccagatgaa gttctctagt gcaacactag tccgtgcaag tcggttcata acaatatcaa   11880
atgataacat ggcactcaaa gaagcagggg agtcgaagga tactaatctc gtgtatcagc   11940
agattatgct aactgggcta agcttgttcg agttcaatat gagatataag aaaggttcct   12000
tagggaagcc actgatattg cacttacatc ttaataacgg gtgctgtata atggagtccc   12060
cacaggaggc gaatatcccc ccaaggtcca cattagattt agagattaca caagagaaca   12120
ataaattgat ctatgatcct gatccactca aggatgtgga ccttgagcta tttagcaagg   12180
tcagagatgt tgtacataca gttgacatga cttattggtc agatgatgaa gttatcagag   12240
caaccagtat ctgtactgca atgacgtag ctgatacaat gtctcaatta gatagagaca   12300
acctaaaaga gatgatcgcg ctagtaaatg acgatgatgt caacagcctg attactgagt   12360
ttatggtgat tgatgttcct ttattttgct caacgttcgg gggtattcta gtcaatcagt   12420
ttgcatactc actctacggc ttaaacatca gaggaaggga agaaatatgg ggacatgtag   12480
tccggattct taaagatacc tcccacgcag ttctaaaagt cttatctaat gctctatctc   12540
```

```
atcccaaaat cttcaaacga ttctggaatg caggtgtcgt ggaacctgtg tatgggccta   12600
acctctcaaa tcaggacaag atactcttgg ccctctctgt ctgtgaatat tctgtggatc   12660
tattcatgca cgattggcaa gggggtgtac cgcttgagat cttttatctgt gacaatgacc  12720 cagatgtggc cgacatgagg aggtcctctt tcttggcaag acatcttgca tacctatgca   12780
gcgtggcaga gatatctagg gatgggccaa gattagaatc aatgaactct ctagagaggc   12840
tcgagtcact aaagagttac ctggaactca catttcttga tgacccggta ctgaggtaca   12900
gtcagttgac tggcctagtc atcaaagtat tcccatctac tttgacctat atccggaagt   12960
catctataaa agtgttaagg acaagaggta taggagtccc tgaagtctta aagattggg    13020 atcccgaggc agataatgca ctgttagatg gtatcgcggc agaaatacaa cagaatattc   13080
cttggggaca tcagactaga gccccttttt gggggttgag agtatccaag tcacaggtac   13140
tgcgtctccg ggggtacaag agatcacaa gaggtgagat aggcagatca ggcgttggtc    13200
tgacgttacc attcgatgga agatatctat ctcaccagct gaggctcttt ggcatcaaca   13260
gtactagctg cttgaaagca cttgaactta cctacctatt gagcccctta gttgacaagg   13320
ataaagatag gctatattta ggggaaggag ctggggccat gctttcctgt tatgacgcta   13380
ctcttggccc atgcatcaac tattataact caggggtata ctcttgtgat gtcaatgggc   13440
agagagagtt aaatatatat cctgctgagg tggcactggt gggaaagaaa ttaaacaatg   13500
ttactagtct gggtcaaaga gttaaagtgt tattcaacgg gaatcctggc tcgacatgga   13560
ttggaaatga tgagtgtgag gctttgattt ggaatgaatt gcagaatagc tcgataggcc   13620
tagtccactg tgacatggag ggaggagatc ataaggatga tcaagttgta ctgcatgagc   13680
attacagtgt aatccggatc gcgtatctgg tgggggatcg agacgttgtg cttataagca   13740
agattgctcc taggctgggc acggattgga ccaggcagct cagcctatat ctgagatact   13800
gggacgaggt taacctaata gtgcttaaaa catctaaccc tgcttccaca gagatgtatc   13860
tcctatcgag gcatcccaaa tctgacatta tagaggacag caagacggtg ttagctagtc   13920
tcctcccttt gtcaaaagaa gatagcatca agatagaaaa gtggatctta atagagaagg   13980
caaaggctca cgaatgggtt actcgggaat tgagagaagg aagctcttca tcagggatgc   14040 ttagaccttta ccatcaagca ctgcagacgt ttggctttga accaaacttg tataaattga   14100
gcagagattt cttgtccacc atgaacatag ctgatacaca caactgcatg atagctttca   14160 acagggttt gaaggataca atcttcgaat gggctagaat aactgagtca gataaaaggc   14220
ttaaactaac tggtaagtat gacctgtatc ctgtgagaga ttcaggcaaa ttgaagacag   14280
tttctagaag acttgtgcta tcttggatat ctttatctat gtccacaaga ttggtaactg   14340
ggtcattccc tgaccagaag tttgaagcaa gacttcaatt gggaatagtt tcattatcat   14400
cccgtgaaat caggaacctg agggttatca caaaaacttt attagaccgg tttgaggata   14460
ttatacatag tataacgtac agattcctca ccaaagaaat aaagattttg atgaagattt   14520
taggggcagt caagatgttc ggggccaggc aaaatgaata cacgaccgtg attgatgatg   14580
gatcactggg tgatatcgag ccatatgaca gctcgtaata attagtccct atcgtgcaga   14640
acgatcgaag ctccgcggta cctggaagtc ttggactgat ccatatgaca atagtaagaa   14700
aaacttacaa gaagacaaga aaatttaaaa gaatacatat ctcttaaact cttgtctggt   14760
```

<210> SEQ ID NO 7
<211> LENGTH: 38
<212> TYPE: DNA
<213> ORGANISM: Artificial

```
<220> FEATURE:
<223> OTHER INFORMATION: Primer

<400> SEQUENCE: 7
actagctagc agtctgacat ggctgtcagc gacgcgct                              38

<210> SEQ ID NO 8
<211> LENGTH: 32
<212> TYPE: DNA
<213> ORGANISM: Artificial
<220> FEATURE:
<223> OTHER INFORMATION: Primer

<400> SEQUENCE: 8
ggtccacgcg tttaaaaatg cctcttcatg tg                                    32

<210> SEQ ID NO 9
<211> LENGTH: 1845
<212> TYPE: DNA
<213> ORGANISM: Artificial
<220> FEATURE:
<223> OTHER INFORMATION: pMO026

<400> SEQUENCE: 9
gaattcgagt catcccgaga cgcgagttat gtgtttgcaa gacgtgccct aaagtctgca      60
aactatgcag agatgacatt caatgtatgc ggcctgatcc tttctgccga gaaatcttcc    120
gctcgtaagg tagatgagaa caaacaactg ctcaaacaga tccaagagag cgtggaatca    180
ttccgggata tttacaagag attctctgag tatcagaaag aacagaactc attgctgatg    240
tccaacctat ctacacttca tatcatcaca gatagaggtg gcaagactga acacacagac    300
tcccttacaa ggtcccccctc cgttttttgca aaatcaaaag agaacaagac taaggctacc    360
aggtttgacc catctatgga gaccttagaa gatatgaagt acaaaccgga cctaatccga    420
gaggatgaat ttagagatga gatccgcaac ccggtgtacc aagagaggga cacagaaccc    480
agggcctcaa acgcatcacg tctcttcccc tccaaagaga gcccacaat gcactctctc     540 aggctcgtca tagagagcag tcccctaagc agagctgaga aagcagcata tgtgaaatca    600
ttatccaagt gcaagacaga ccaagaggtt aaggcagtca tggaactcgt agaagaggac    660
atagagtcac tgaccaacta gatcccgggt gaggcatccc accatcctca gtcacagaga    720
gacccaatct accatcagca tcagccagta aagattaaga aaaacttagg gtgaaagaaa    780
tgcggccgct tgctagcaga atatatgaaa acatttaaca tttctcaaca agatctagaa    840
ttagtagaag tagcgacaga gaagattaca atgctttatg aggataataa acatcatgtg    900
ggagcggcaa ttcgtacgaa acaggagaaa atcatttcgg cagtacatat tgaagcgtat    960
ataggacgag taactgtttg tgcagaagcc attgccattg gtagtgcagt ttcgaatgga   1020
caaaaggatt ttgacacgat tgtagctgtt agacacccctt attctgacga agtagataga   1080
agtattcgag tggtaagtcc ttgtggtatg tgtagggagt tgatttcaga ctatgcacca   1140
gattgttttg tgttaataga aatgaatggc aagttagtca aaactacgat tgaagaactc   1200
attccactca aatatacccg aaattaaaac gcgtcagaga cctgcaacaa tgtctcaagc   1260
agacaccacc tggcagtcgg agccaccggg tcactccttg tcttaaataa gaaaaactta   1320
gggataaagt cccttgtgag tgcttggttg caaaactctc cccttgggaa acatgacagc   1380
atatatccgg aggtcacagt gcatctcaac atcactactg ttgttctca ccacattggt    1440 ctcgtgtcag attcccaggg atatgctctc taacatagg gtcatagtcg atgaagggaa    1500
atcactgaag atagctgggt cccacgaatc gaggtacata gtactgagtc tagttccggg   1560
```

```
ggtagacctt gagaatggat gcggaacagc tcaggttatc cagtacaaga gcctactgaa    1620
caggctgtta atcccattga gggatgcctt agatcttcag gaggctctga taactgtcac    1680
caatgatacg acacaaaatg ccggtgttcc acagttgaga ttcttcggtg ctgtgattgg    1740
tactatcgca cttggagtgg cgacatcagc acagatcacc acaggattg cactagccga     1800 agcgagggag gccaaaagag acatagcgct catcaaggaa tcgat                    1845
```

<210> SEQ ID NO 10
<211> LENGTH: 39
<212> TYPE: DNA
<213> ORGANISM: Artificial
<220> FEATURE:
<223> OTHER INFORMATION: Primer

<400> SEQUENCE: 10

```
actagctagc ttagacgctg gattttttc gggtagtgg                              39
```

<210> SEQ ID NO 11
<211> LENGTH: 30
<212> TYPE: DNA
<213> ORGANISM: Artificial
<220> FEATURE:
<223> OTHER INFORMATION: Primer

<400> SEQUENCE: 11

```
gtccgacgtc cttacgcaca agagttccgt                                       30
```

<210> SEQ ID NO 12
<211> LENGTH: 5160
<212> TYPE: DNA
<213> ORGANISM: Artificial
<220> FEATURE:
<223> OTHER INFORMATION: pMO094(+E)Mp;Klf4 XhoI-

<400> SEQUENCE: 12

```
ctcgagtaat acgactcact atagggacca acaagagaa gaaacatgta tggaatatat     60
aatgaagttt aagaaaaact tagggtcaaa gtatccaccc tgaggagcag gttccagatc    120
cttttctttg ctgccaaagt tcacgatggc cgggttgttg agcaccttcg atacatttag    180
ctctaggagg agcgaaagta ttaataagtc gggaggaggt gctgttatcc ccggccagag    240
gagcacagtc tcagtgttca tactaggccc aagtgtgact gatgatgcag acaagttatt    300
cattgcaaca accttcctag ctcactcatt ggacacagat aagcagcact tcagagagg     360 agggttcctc gtctctctgc ttgccatggc ttacagtagt ccagaattgt acttgacaac    420
aaacggagta aacgccgatg tcaaatatgt gatctacaac atagagaaag accctaagag    480
gacgaagaca gacggattca ttgtgaagac gagagatatg gaatatgaga ggaccacaga    540
atggctgttt ggacctatgg tcaacaagag cccactcttc cagggtcaac gggatgctgc    600
agaccctgac acactccttc aaatctatgg gtatcctgca tgcctaggag caataattgt    660
ccaagtctgg attgtgctgg tgaaggccat cacaagcagc gccggcttaa ggaaagggtt    720
cttcaacagg ttagaggcgt tcagacaaga cggcaccgtg aaaggtgcct tagttttcac    780
tggggagaca gttgagggga taggctcggt tatgagatct cagcaaagcc ttgtatctct    840
catggttgag acccttgtga ctatgaatac tgcaagatct gatctcacca cattagagaa    900
gaacatccag atcgttggga actacatccg agatgcaggg ctggcttcct tcatgaacac    960
tattaaatat ggggtggaga caaagatggc agctctaacg ttgtcaaacc tgaggccga    1020 tattaataag cttagaagcc tcatagacac ctacctgtca aaaggcccca gagctccctt    1080
```

```
tatctgtatc ctcaaggacc ctgttcatgg tgaatttgct ccaggcaatt atcctgcact    1140
atggagttac gccatgggag tcgccgtcgt acagaacaag tcaatgcagc agtacgtcac    1200
agggaggaca taccttgata tggaaatgtt cttactagga caagccgtgg caaaggatgc    1260
tgaatcgaag atcagcagtg ccttggaaga tgagttagga gtgacggata cagccaagga    1320
gaggctcaga catcatctgg caaacttgtc cggtggggat ggtgcttacc acaaaccaac    1380
aggcggtggt gcaattgagg tagctctaga caatgccgat atcgacctgg aaacagaagc    1440
tcatgcggac caggacgcta ggggttgggg tggagatagt ggtgaaagat ggcacgtca    1500 ggtgagtggt ggccactttg tcacactaca tggggctgaa cggttagagg aggaaaccaa    1560
tgatgaggat gtatcagaca tagagagaag aatagccatg agactcgcag agagacggca    1620
agaggattct gcaacccatg gagatgaagg ccgcaataac ggtgttgatc acgaagaaga    1680
tgacgatgcc gcagcagcag ctgggatagg aggaatctag gatcatacga ggcctcaagg    1740
tacttgatcc gcagtaagaa aaacttaggg tgaaagttca tccaccgatc ggctcaggca    1800
aggccacacc caaccccacc gaccacaccc agcagtcgag acagccacgg cttcggctac    1860
acttaccgca tggatcaaga tgccttcatt cttaaagaag attctgaagt tgagaggaag    1920
gcgccaggag gacgagagtc gctctcggat gttatcggat tcctcgatgc tgtcctgtcg    1980
aatgaaccaa ctgacatcgg aggggacaga agctggctcc acaacaccat caacactccc    2040
caaggaccag gctctgctca tagagccaaa agtgagggcg aaggagaagt ctcaacaccg    2100
tcgacccaag ataatcgatc aggtgaggag agtagagtct ctgggagaac aagcaagcca    2160
gaggcagaag cacatgctgg aaaccttgat aaacaaaata tacactgggc ctttagggga    2220
agaactggta caaactctgt atctcaggat ctggacgatg gaggagactc cggaatcctt    2280
gaaaatcctc caaatgagag aggatatccg agatcaggta ttgaagatga aaacagagag    2340
atggctgcgc accctgataa gaggggagaa gaccaagctg aaggacttcc agaagaggta    2400
cgaggaggta catccctacc tgatgaagga gaaggtggag caagtaataa tggaagaagc    2460
atggagcctg gcagctcaca tagtgcaaga gtaactgggg tcctggtgat tcctagcccc    2520
gaacttgaag aggctgtgct acggaggaac aaaagaagac ctaccaacag tgggtccaaa    2580
cctcttactc cagcaaccgt gcctggcacc cggtccccac cgctgaatcg ttacaacagc    2640
acagggtcac caccaggaaa accccatct acacaggatg agcacatcaa ctctggggac    2700 accccgccg tcagggtcaa agaccggaaa ccatcaatag ggactcgctc tgtctcagat    2760
tgtccagcca acggccgccc aatccatccg ggtatagaga ccgactcaac aaaaaagggc    2820
ataggagaga acacatcatc tatgaaagat atggctacat tgttgacgag tcttggtgta    2880
atccagtctg ctcaagaatt cgagtcatcc cgagacgcga gttatgtgtt tgcaagacgt    2940
gccctaaagt ctgcaaacta tgcagagatg acattcaatg tatgcggcct gatcctttct    3000
gccgagaaat cttccgctcg taaggtagat gagaacaaac aactgctcaa acagatccaa    3060
gagagcgtgg aatcattccg ggatatttac aagagattct ctgagtatca gaaagaacag    3120
aactcattgc tgatgtccaa cctatctaca cttcatatca tcacagatag aggtggcaag    3180
actgacaaca cagactccct tacaaggtcc ccctccgttt ttgcaaaatc aaaagagaac    3240
aagactaagg ctaccaggtt tgacccatct atggagacct agaagatat gaagtacaaa    3300 ccggacctaa tccgagagga tgaatttaga gatgagatcc gcaacccggt gtaccaagag    3360
agggacacag aacccaggc ctcaaacgca tcacgtctct tccctccaa agagaagccc    3420 acaatgcact ctctcaggct cgtcatagag agcagtcccc taagcagagc tgagaaagca    3480
```

```
gcatatgtga atcattatc caagtgcaag acagaccaag aggttaaggc agtcatggaa    3540
ctcgtagaag aggacataga gtcactgacc aactagatcc cgggtgaggc atcccaccat    3600
cctcagtcac agagagaccc aatctaccat cagcatcagc cagtaaagat taagaaaaac    3660
ttagggtgaa agaaatttca ccgctagcac ctaggtctga catggctgtc agcgacgcgc    3720
tgctcccatc tttctccacg ttcgcgtctg gccggcggg aagggagaag acactgcgtc    3780
aagcaggtgc cccgaataac cgctggcggg aggagctctc ccacatgaag cgacttcccc    3840
cagtgcttcc cggccgcccc tatgacctgg cggcggcgac cgtggccaca gacctggaga    3900
gcggcggagc cggtgcggct tgcggcggta gcaacctggc gccctacct cggagagaga    3960 ccgaggagtt caacgatctc ctggacctgg actttattct ctccaattcg ctgacccatc    4020
ctccggagtc agtggccgcc accgtgtcct cgtcagcgtc agcctcctct tcgtcgtcgc    4080
cgtcgagcag cggccctgcc agcgcgcgcc ccacctgcag cttcacctat ccgatccggg    4140
ccgggaacga cccgggcgtg gcgccggcg gcacgggcg aggcctcctc tatggcaggg    4200
agtccgctcc ccctccgacg gctcccttca acctggcgga catcaacgac gtgagcccct    4260
cgggcggctt cgtggccgag ctcctgcggc cagaattgga cccggtgtac attccgccgc    4320
agcagccgca gccgccaggt ggcgggctga tgggcaagtt cgtgctgaag gcgtcgctga    4380
gcgcccctgg cagcgagtac ggcagcccgt cggtcatcag cgtcagcaaa ggcagccctg    4440
acggcagcca cccggtggtg gtggcgccct acaacggcgg gccgccgcgc acgtgcccca    4500
agatcaagca ggaggcggtc tcttcgtgca cccacttggg cgctggaccc cctctcagca    4560
atggccaccg gccggctgca cacgacttcc ccctggggcg gcagctcccc agcaggacta    4620
ccccgacccc gggtcttgag gaagtgctga gcagcaggga ctgtcaccct gccctgccgc    4680
ttcctcccgg cttccatccc cacccgggc ccaattaccc atccttcctg cccgatcaga    4740
tgcagccgca gtcccgccg ctccattacc aagagctcat gccacccggt tcctgcatgc    4800
cagaggagcc caagccaaag aggggaagac gatcgtggcc ccggaaaagg accgccaccc    4860
acacttgtga ttacgcgggc tgcggcaaaa cctacacaaa gagttcccat ctcaaggcac    4920
acctgcgaac ccacacaggt gagaaacctt accactgtga ctgggacggc tgtggatgga    4980
aattcgcccg ctcagatgaa ctgaccaggc actaccgtaa acacacgggg caccgccgt    5040 tccagtgcca aaaatgcgac cgagcatttt ccaggtcgga ccacctcgcc ttacacatga    5100
agaggcattt ttaaagacgt cgattaagaa aaacttaggg tgaaagttca tcgcggccgc    5160
```

<210> SEQ ID NO 13
<211> LENGTH: 15696
<212> TYPE: DNA
<213> ORGANISM: Artificial
<220> FEATURE:
<223> OTHER INFORMATION: Template cDNA for SeVp(Mp+myc,delta-M::Klf4,
      delta-F::Oct4,delta-HN::Sox2)

<400> SEQUENCE: 13

```
accaaacaag agaagaaaca tgtatggaat atataatgaa gtttaagaaa aacttagggt      60
caaagtatcc accctgagga gcaggttcca gatccttttc tttgctgcca agttcacga     120 tggccgggtt gttgagcacc ttcgatacat ttagctctag gaggagcgaa agtattaata    180
agtcgggagg aggtgctgtt atccccggcc agaggagcac agtctcagtg ttcatactag    240
gcccaagtgt gactgatgat gcagacaagt tattcattgc aacaaccttc ctagctcact    300
cattggacac agataagcag cactctcaga gaggagggtt cctcgtctct ctgctcttgcca    360
```

| | |
|---|---|
| tggcttacag tagtccagaa ttgtacttga caacaaacgg agtaaacgcc gatgtcaaat | 420 |
| atgtgatcta caacatagag aaagacccta agaggacgaa gacagacgga ttcattgtga | 480 |
| agacgagaga tatggaatat gagaggacca cagaatggct gtttggacct atggtcaaca | 540 |
| agagcccact cttccagggt caacgggatg ctgcagaccc tgacacactc cttcaaatct | 600 |
| atgggtatcc tgcatgccta ggagcaataa ttgtccaagt ctggattgtg ctggtgaagg | 660 |
| ccatcacaag cagcgccggc ttaaggaaag ggttcttcaa caggttagag gcgttcagac | 720 |
| aagacggcac cgtgaaaggt gccttagttt tcactgggga gacagttgag gggataggct | 780 |
| cggttatgag atctcagcaa agccttgtat ctctcatggt tgagacccct gtgactatga | 840 |
| atactgcaag atctgatctc accacattag agaagaacat ccagatcgtt gggaactaca | 900 |
| tccgagatgc agggctggct tccttcatga acactattaa atatggggtg gagacaaaga | 960 |
| tggcagctct aacgttgtca aacctgaggc ccgatattaa taagcttaga agcctcatag | 1020 |
| acacctacct gtcaaaaggc cccagagctc cctttatctg tatcctcaag gaccctgttc | 1080 |
| atggtgaatt tgctccaggc aattatcctg cactatggag ttacgccatg ggagtcgccg | 1140 |
| tcgtacagaa caagtcaatg cagcagtacg tcacagggag gacataccct tgatatggaaa | 1200 |
| tgttcttact aggacaagcc gtggcaaagg atgctgaatc gaagatcagc agtgccttgg | 1260 |
| aagatgagtt aggagtgacg gatacagcca aggagaggct cagacatcat ctggcaaact | 1320 |
| tgtccggtgg ggatggtgct taccacaaac caacaggcgg tggtgcaatt gaggtagctc | 1380 |
| tagacaatgc cgatatcgac ctggaaacag aagctcatgc ggaccaggac gctaggggtt | 1440 |
| ggggtggaga tagtggtgaa agatgggcac gtcaggtgag tggtggccac tttgtcacac | 1500 |
| tacatgggc tgaacggtta gaggaggaaa ccaatgatga ggatgtatca gacatagaga | 1560 |
| gaagaatagc catgagactc gcagagagac ggcaagagga ttctgcaacc catggagatg | 1620 |
| aaggccgcaa taacggtgtt gatcacgaag aagatgacga tgccgcagca gcagctggga | 1680 |
| taggaggaat ctaggatcat acgaggcctc aaggtacttg atccgcagta agaaaaactt | 1740 |
| agggtgaaag ttcatccacc gatcggctca ggcaaggcca cacccaaccc caccgaccac | 1800 |
| acccagcagt cgagacagcc acggcttcgg ctacacttac cgcatggatc aagatgcctt | 1860 |
| cattcttaaa gaagattctg aagttgagag gaaggcgcca ggaggacgag agtcgctctc | 1920 |
| ggatgttatc ggattcctcg atgctgtcct gtcgaatgaa ccaactgaca tcggagggga | 1980 |
| cagaagctgg ctccacaaca ccatcaacac tccccaagga ccaggctctg ctcatagagc | 2040 |
| caaaagtgag ggcgaaggag aagtctcaac accgtcgacc caagataatc gatcaggtga | 2100 |
| ggagagtaga gtctctggga gaacaagcaa gccagaggca gaagcacatg ctggaaacct | 2160 |
| tgataaacaa aatatacact gggcctttag gggaagaact ggtacaaact ctgtatctca | 2220 |
| ggatctggac gatggaggag actccggaat ccttgaaaat cctccaaatg agagaggata | 2280 |
| tccgagatca ggtattgaag atgaaaacag agagatggct gcgcaccctg ataagagggg | 2340 |
| agaagaccaa gctgaaggac ttccagaaga ggtacgagga ggtacatccc tacctgatga | 2400 |
| aggagaaggt ggagcaagta ataatggaag aagcatggag cctggcagct cacatagtgc | 2460 |
| aagagtaact ggggtcctgg tgattcctag ccccgaactt gaagaggctg tgctacggag | 2520 |
| gaacaaaaga agacctacca acagtgggtc caaacctctt actccagcaa ccgtgcctgg | 2580 |
| cacccggtcc ccaccgctga atcgttacaa cagcacaggg tcaccaccag gaaaaccccc | 2640 |
| atctacacag gatgagcaca tcaactctgg ggacaccccc gccgtcaggg tcaaagaccg | 2700 |
| gaaaccatca ataggggactc gctctgtctc agattgtcca gccaacggcc gcccaatcca | 2760 |

```
tccgggtata gagaccgact caacaaaaaa gggcatagga gagaacacat catctatgaa    2820
agatatggct acattgttga cgagtcttgg tgtaatccag tctgctcaag aattcgagtc    2880
atcccgagac gcgagttatg tgtttgcaag acgtgcccta aagtctgcaa actatgcaga    2940
gatgacattc aatgtatgcg gcctgatcct ttctgccgag aaatcttccg ctcgtaaggt    3000
agatgagaac aaacaactgc tcaaacagat ccaagagagc gtggaatcat tccgggatat    3060
ttacaagaga ttctctgagt atcagaaaga acagaactca ttgctgatgt ccaacctatc    3120
tacacttcat atcatcacag atagaggtgg caagactgac aacacagact cccttacaag    3180 gtcccctcc gttttgcaa atcaaaaga gaacaagact aaggctacca ggtttgaccc    3240
atctatggag accttagaag atatgaagta caaaccggac ctaatccgag aggatgaatt    3300
tagagatgag atccgcaacc cggtgtacca agagagggac acagaaccca gggcctcaaa    3360
cgcatcacgt ctcttcccct ccaaagagaa gcccacaatg cactctctca ggctcgtcat    3420
agagagcagt cccctaagca gagctgagaa agcagcatat gtgaaatcat tatccaagtg    3480
caagacagac caagaggtta aggcagtcat ggaactcgta aagaggaca tagagtcact    3540 gaccaactag atcccgggtg aggcatccca ccatcctcag tcacagagag acccaatcta    3600
ccatcagcat cagccagtaa agattaagaa aaacttaggg tgaaagaaat ttcaccgcta    3660
gcttagacgc tggattttttt tcgggtagtg gaaaaccagc agcctcccgc gacgatgccc    3720
ctcaacgtta gcttcaccaa caggaactat gacctcgact acgactcggt gcagccgtat    3780
ttctactgcg acgaggagga gaacttctac cagcagcagc agcagagcga gctgcagccc    3840
ccggcgccca gcgaggatat ctggaagaaa ttcgagctgc tgcccacccc gcccctgtcc    3900
cctagccgcc gctccgggct ctgctcgccc tcctacgttg cggtcacacc cttctccctt    3960
cggggagaca acgacggcgg tggcgggagc ttctccacgg ccgaccagct ggagatggtg    4020
accgagctgc tgggaggaga catggtgaac cagagtttca tctgcgaccc ggacgacgag    4080
accttcatca aaaacatcat catccaggac tgtatgtgga gcggcttctc ggccgccgcc    4140
aagctcgtct cagagaagct ggcctcctac caggctgcgc gcaaagacag cggcagcccg    4200
aaccccgccc gcggccacag cgtctgctcc acctccagct tgtacctgca ggatctgagc    4260
gccgccgcct cagagtgcat cgacccctcg gtggtcttcc cctaccctct caacgacagc    4320
agctcgccca agtcctgcgc ctcgcaagac tccagcgcct tctctccgtc ctcggattct    4380
ctgctctcct cgacggagtc ctccccgcag ggcagccccg agccctggt gctccatgag    4440 gagacaccgc ccaccaccag cagcgactct gaggaggaac aagaagatga ggaagaaatc    4500
gatgttgttt ctgtggaaaa gaggcaggct cctggcaaaa ggtcagagtc tggatcacct    4560
tctgctggag gccacagcaa acctcctcac agcccactgg tcctcaagag gtgccacgtc    4620
tccacacatc agcacaacta cgcagcgcct ccctccactc ggaaggacta tcctgctgcc    4680
aagagggtca agttggacag tgtcagagtc ctgagacaga tcagcaacaa ccgaaaatgc    4740
accagcccca ggtcctcgga caccgaggag aatgtcaaga ggcgaacaca caacgtcttg    4800
gagcgccaga ggaggaacga gctaaaacgg agctttttttg ccctgcgtga ccagatcccg    4860
gagttggaaa acaatgaaaa ggcccccaag gtagttatcc ttaaaaaagc cacagcatac    4920
atcctgtccg tccaagcaga ggagcaaaag ctcatttctg aagaggactt gttgcggaaa    4980
cgacgagaac agttgaaaca caaacttgaa cagctacgga actcttgtgc gtaaggacgt    5040
cgattaagaa aaacttaggg tgaaagttca tcgcggccgc ttgctagcag tctgacatgg    5100
ctgtcagcga cgcgctgctc ccatctttct ccacgttcgc gtctggcccg gcgggaaggg    5160
```

```
agaagacact gcgtcaagca ggtgccccga ataaccgctg gcgggaggag ctctcccaca    5220
tgaagcgact tcccccagtg cttcccggcc gccccccatga cctggcggcg gcgaccgtgg    5280
ccacagacct ggagagcggc ggagccggtg cggcttgcgg cggtagcaac ctggcgcccc    5340
tacctcggag agagaccgag gagttcaacg atctcctgga cctggacttt attctctcca    5400
attcgctgac ccatcctccg gagtcagtgg ccgccaccgt gtcctcgtca gcgtcagcct    5460
cctcttcgtc gtcgccgtcg agcagcggcc ctgccagcgc gccctccacc tgcagcttca    5520
cctatccgat ccgggccggg aacgacccgg gcgtggcgcc gggcggcacg ggcggaggcc    5580
tcctctatgg cagggagtcc gctcccccctc cgacggctcc cttcaacctg gcggacatca    5640
acgacgtgag cccctcgggc ggcttcgtgg ccgagctcct gcggccagaa ttggacccgg    5700
tgtacattcc gccgcagcag ccgcagccgc caggtggcgg gctgatgggc aagttcgtgc    5760
tgaaggcgtc gctgagcgcc cctggcagcg agtacggcag cccgtcggtc atcagcgtca    5820
gcaaaggcag ccctgacggc agccaccccgg tggtggtggc gccctacaac ggcgggccgc    5880
cgcgcacgtg ccccaagatc aagcaggagg cggtctcttc gtgcacccac ttgggcgctg    5940 gacccccctct cagcaatggc caccggccgg ctgcacacga cttcccccctg gggcggcagc    6000 tccccagcag gactaccccg accctgggtc ttgaggaagt gctgagcagc agggactgtc    6060
accctgccct gccgcttcct cccggcttcc atccccaccc ggggcccaat tacccatcct    6120
tcctgcccga tcagatgcag ccgcaagtcc cgccgctcca ttaccaagag ctcatgccac    6180
ccggttcctg catgccagag gagcccaagc caaagagggg aagacgatcg tggcccccgga    6240 aaaggaccgc cacccacact tgtgattacg cgggctgcgg caaaacctac acaaagagtt    6300
cccatctcaa ggcacacctg cgaacccaca caggtgagaa accttaccac tgtgactggg    6360
acggctgtgg atggaaattc gcccgctcag atgaactgac caggcactac cgtaaacaca    6420
cggggcaccg cccgttccag tgccaaaaat gcgaccgagc attttccagg tcggaccacc    6480
tcgccttaca catgaagagg cattttttaaa cgcgtcagag acctgcaaca atgtctcaag    6540
cagacaccac ctggcagtcg gagccaccgg gtcactcctt gtcttaaata agaaaaactt    6600
agggataaag tcccttagat ctagcctagg ttccccatgg cgggacacct ggcttcggat    6660
ttcgccttct cgccccctcc aggtggtgga ggtgatgggc cagggggggcc ggagccgggc    6720 tgggttgatc ctcggacctg gctaagcttc caaggccctc ctggagggcc aggaatcggg    6780 ccggggggttg ggccaggctc tgaggtgtgg gggattcccc catgccccccc gccgtatgag    6840 ttctgtgggg ggatggcgta ctgtgggccc caggttggag tggggctagt gccccaaggc    6900
ggcttggaga cctctcagcc tgagggcgaa gcaggagtcg gggtggagag caactccgat    6960
ggggcctccc cggagccctg caccgtcacc cctggtgccg tgaagctgga gaaggagaag    7020
ctggagcaaa acccggagga gtcccaggac atcaaagctc tgcagaaaga actcgagcaa    7080
tttgccaagc tcctgaagca gaagaggatc accctgggat atacacaggc cgatgtgggg    7140 ctcacccctgg gggttctatt tgggaaggta ttcagccaaa cgaccatctg ccgcttgag    7200 gctctgcagc ttagcttcaa gaacatgtgt aagctgcggc ccttgctgca gaagtgggtg    7260
gaggaagctg acaacaatga aaatcttcag gagatatgca aagcagaaac cctcgtgcag    7320
gcccgaaaga gaaagcgaac cagtatcgag aaccgagtga gaggcaacct ggagaatttg    7380
ttcctgcagt gcccgaaacc cacactgcag cagatcagcc acatcgccca gcagcttggg    7440
ctcgagaagg atgtggtccg agtgtggttc tgtaaccggc gccagaaggg caagcgatca    7500
agcagcgact atgcacaacg agaggatttt gaggctgctg ggtctccttt ctcaggggga    7560
```

```
ccagtgtcct ttcctctggc cccagggccc cattttggta ccccaggcta tgggagccct      7620
cacttcactg cactgtactc ctcggtccct ttccctgagg gggaagcctt tccccctgtc      7680
tccgtcacca ctctgggctc tcccatgcat tcaaactgag gacgtcagat ctgtatataa      7740
taagaaaaac ttagggtgaa agtgaggttg cgcggtattt tagctagccc gcatgtacaa      7800
catgatggag acggagctga agccgccggg cccgcagcaa acttcggggg gcggcggcgg      7860
caactccacc gcggcggcgg ccggcggcaa ccagaaaaac agcccggacc gcgtcaagcg      7920
gcccatgaat gccttcatgg tgtggtcccg cgggcagcgg cgcaagatgg cccaggagaa      7980
ccccaagatg cacaactcgg agatcagcaa gcgcctgggc gccgagtgga aacttttgtc      8040
ggagacggag aagcggccgt tcatcgacga ggctaagcgg ctgcgagcgc tgcacatgaa      8100
ggagcacccg gattataaat accgccccg gcggaaaacc aagacgctca tgaagaagga      8160
taagtacacg ctgcccggcg ggctgctggc ccccggcggc aatagcatgg cgagcgggt       8220 cggggtgggc gccggcctgg gcgcgggcgt gaaccagcgc atggacagtt acgcgcacat      8280
gaacggctgg agcaacggca gctacagcat gatgcaggac cagctgggct acccgcagca      8340
cccgggcctc aatgcgcacg gcgcagcgca gatgcagccc atgcaccgct acgacgtgag      8400
cgccctgcag tacaactcca tgaccagctc gcagacctac atgaacggct cgcccaccta      8460
cagcatgtcc tactcgcagc agggcacccc tggcatggct cttggctcca tgggttcggt      8520
ggtcaagtcc gaggccagct ccagccccc tgtggttacc tcttcctccc actccagggc      8580
gccctgccag gccggggacc tccgggacat gatcagcatg tatctccccg cgccgaggt      8640 gccggaaccc gccgccccca gcagacttca catgtcccag cactaccaga gcggcccggt      8700
gcccggcacg gccattaacg gcacactgcc cctctcacac atgtgagacc ggtgtcggct      8760
ttgctgacac tagagtcatc tccgaacatc cacaatatct ctcagtctct tacgtctctc      8820
acagtattaa gaaaaaccca gggtgaatgg gaagcttgcc ataggtcatg gatgggcagg      8880
agtcctccca aaacccttct gacatactct atccagaatg ccacctgaac tctcccatag      8940
tcagggggaa gatagcacag ttgcacgtct tgttagatgt gaaccagccc tacagactaa      9000
aggacgacag cataataaat attacaaagc acaaaattag gaacggagga ttgtcccctc      9060
gtcaaattaa gatcaggtct ctgggtaagg ctcttcaacg cacaataaag gatttagacc      9120
gatacacctt tgaaccgtac ccaacctact ctcaggaatt acttaggctt gatataccag      9180
agatatgtga caaaatccga tccgtcttcg cggtctcgga tcggctgacc agggagttat      9240 ctagtggggtt ccaggatctt tggttgaata tcttcaagca actaggcaat atagaaggaa      9300
gagaggggta cgatccgttg caggatatcg gcaccatccc ggagataact gataaataca      9360
gcaggaatag atggtatagg ccattcctaa cttggttcag catcaaatat gacatgcggt      9420
ggatgcagaa gaccagaccg gggggacccc tcgatacctc taattcacat aacctcctag      9480
aatgcaaatc atacactcta gtaacatacg gagatcttat catgatactg aacaagttga      9540
cattgacagg gtatatccta acccctgagc tggtcttgat gtattgtgat gttgtagagg      9600
gaaggtggaa tatgtctgct gcagggcatc tagataagaa gtccattggg ataacaagca      9660
aaggtgagga attatgggaa ctagtggatt ccctcttctc aagtcttgga gaggaaatat      9720
acaatgtcat cgcactattg gagccccat cacttgctct catacaacta aatgatccag       9780 ttataccctct acgtggggca tttatgaggc atgtgttgac agagctacag gctgttttaa      9840
caagtaggga cgtgtacaca gatgctgaag cagacactat tgtggagtcg ttactcgcca      9900
ttttccatgg aacctctatt gatgagaaag cagagatctt ttccttcttt aggacatttg      9960
```

-continued

| | | | | | |
|---|---|---|---|---|---|
| gccaccccag | cttagaggct | gtcactgccg | ccgacaaggt | aagggcccat | atgtatgcac | 10020 |
| aaaaggcaat | aaagcttaag | acccctatacg | agtgtcatgc | agttttttgc | actatcatca | 10080 |
| taaatgggta | tagagagagg | catggcggac | agtggccccc | ctgtgacttc | cctgatcacg | 10140 |
| tgtgtctaga | actaaggaac | gctcaagggt | ccaatacggc | aatctcttat | gaatgtgctg | 10200 |
| tagacaacta | tacaagtttc | ataggcttca | agtttcggaa | gtttatagaa | ccacaactag | 10260 |
| atgaagatct | cacaatatat | atgaaagaca | aagcactatc | ccccaggaag | gaggcatggg | 10320 |
| actctgtata | cccggatagt | aatctgtact | ataaagcccc | agaatctgaa | gagacccggc | 10380 |
| ggcttattga | agtgttcata | aatgatgaga | atttcaaccc | agaagaaatt | atcaattatg | 10440 |
| tggagtcagg | agattggttg | aaagacgaga | agttcaacat | ctcgtacagt | ctcaaagaga | 10500 |
| aagagatcaa | gcaagagggt | cgtctattcg | caaaaatgac | ttataagatg | cgagccgtac | 10560 |
| aggtgctggc | agagacacta | ctggctaaag | gaataggaga | gctgttcagc | gaaaatggga | 10620 |
| tggttaaagg | agagatagac | ctacttaaaa | gattgactac | tctttctgtc | tcaggagtcc | 10680 |
| ccaggactga | ttcagtgtac | aataactcta | aatcatcaga | gaagagaaac | gaaggcatga | 10740 |
| aaaagaagaa | ctctgggggg | tactgggacg | aaaagaagag | gtccagacat | gaattcaagg | 10800 |
| caacagattc | atcaacagac | ggctatgaaa | cgttaagttg | cttcctcaca | acagacctca | 10860 |
| agaaatactg | cttaaactgg | agatttgaaa | gtactgcatt | gtttggtcag | agatgcaacg | 10920 |
| agatatttgg | cttcaagacc | ttctttaact | ggatgcatcc | agtccttgaa | aggtgtacaa | 10980 |
| tatatgttgg | ggatccttac | tgtccagtcg | ccgaccggat | gcatcgacaa | ctccaggatc | 11040 |
| atgcagactc | tggcattttc | atacataatc | ctaggggggg | catagaaggt | tactgccaga | 11100 |
| agctgtggac | cttaatctca | atcagtgcaa | tccacctagc | agctgtgaga | gtgggtgtca | 11160 |
| gggtctctgc | aatggttcag | ggtgacaatc | aagctatagc | cgtgacatca | agagtacctg | 11220 |
| tagctcagac | ttacaagcag | aagaaaaatc | atgtctataa | ggagatcacc | aaatattttg | 11280 |
| gtgctctaag | acacgtcatg | tttgatgtag | ggcacgagct | aaaattgaac | gagaccatca | 11340 |
| ttagtagcaa | gatgtttgtc | tatagtaaaa | gaatatacta | tgatgggaag | attttaccac | 11400 |
| agtgcctgaa | agccttgacc | aggtgtgtat | tctggtccga | gacactggta | gatgaaaaca | 11460 |
| gatctgcttg | ttcgaacatc | tcaacatcca | tagcaaaagc | tatcgaaaat | gggtattctc | 11520 |
| ctatactagg | ctactgcatt | gcgttgtata | agacctgtca | gcaggtgtgc | atatcactag | 11580 |
| ggatgactat | aaatccaact | atcagcccga | ccgtaagaga | tcaatacttt | aagggtaaga | 11640 |
| attggctgag | atgtgcagtg | ttgattccag | caaatgttgg | aggattcaac | tacatgtcta | 11700 |
| catctagatg | ctttgttaga | aatattggag | accccgcagt | agcagcccta | gctgatctca | 11760 |
| aaagattcat | cagagcggat | ctgttagaca | agcaggtact | atacagggtc | atgaatcaag | 11820 |
| aacccggtga | ctctagcttt | ctagattggg | cttcagaccc | ttattcatgt | aacctcccgc | 11880 |
| attctcagag | tataactacg | attataaaga | atatcactgc | tagatctgtg | ctgcaggaat | 11940 |
| ccccgaatcc | tctactgtct | ggtctcttca | ccgagactag | tggagaagag | gatctcaacc | 12000 |
| tggcctcgtt | cctatggac | cggaaagtca | tcctgccgag | agtggctcat | gagatcctgg | 12060 |
| gtaattcctt | aactggagtt | agggaggcga | ttgcagggat | gcttgatacg | accaagtctc | 12120 |
| tagtgagatc | cagcgttaag | aaaggaggat | tatcatatgg | gatattgagg | aggcttgtca | 12180 |
| attatgatct | attgcagtac | gagacactga | ctagaactct | caggaaaccg | gtgaaagaca | 12240 |
| acatcgaata | tgagtatatg | tgttcagttg | agctagctgt | cggtctaagg | cagaaaatgt | 12300 |
| ggatccacct | aacttacggg | agacccatac | atgggctaga | aacaccagac | cctttagagc | 12360 |

```
tcttgagggg aacatttatc gaaggttcag aggtgtgcaa gctttgcagg tctgagggag    12420
cagaccccat ctatacatgg ttctatctcc ctgacaatat agacctggac acgcttacaa    12480
acggatgtcc ggctataaga atcccctatt ttggatcagc cactgatgaa aggtcggaag    12540
cccaactcgg gtatgtaaga aatctaagca aacccgcaaa ggctgccatc cggatagcta    12600
tggtgtatac gtgggcctac gggactgatg agatatcgtg gatggaagcc gctcttatag    12660
cccaaacaag agctaatctg agcttagaga atctaaagct gctgactcct gtttcaacct    12720
ccactaatct atctcatagg ttgaaagata cggcaaccca gatgaagttc tctagtgcaa    12780
cactagtccg tgcaagtcgg ttcataacaa tatcaaatga taacatggca ctcaaagaag    12840
caggggagtc gaaggatact aatctcgtgt atcagcagat tatgctaact gggctaagct    12900
tgttcgagtt caatatgaga tataagaaag gttccttagg gaagccactg atattgcact    12960
tacatcttaa taacgggtgc tgtataatgg agtccccaca ggaggcgaat atcccccccaa    13020 ggtccacatt agatttagag attacacaag agaacaataa attgatctat gatcctgatc    13080
cactcaagga tgtggacctt gagctatttta gcaaggtcag agatgttgta catacagttg    13140
acatgactta ttggtcagat gatgaagtta tcagagcaac cagtatctgt actgcaatga    13200
cgatagctga tacaatgtct caattagata gagacaacct aaaagagatg atcgcgctag    13260
taaatgacga tgatgtcaac agcctgatta ctgagtttat ggtgattgat gttccttat    13320 tttgctcaac gttcggggggt attctagtca atcagtttgc atactcactc tacggcttaa    13380
acatcagagg aagggaagaa atatggggac atgtagtccg gattcttaaa gatacctccc    13440
acgcagttct aaaagtctta tctaatgctc tatctcatcc caaaatcttc aaacgattct    13500
ggaatgcagg tgtcgtggaa cctgtgtatg ggcctaacct ctcaaatcag gacaagatac    13560
tcttggccct ctctgtctgt gaatattctg tggatctatt catgcacgat tggcaagggg    13620
gtgtaccgct tgagatcttt atctgtgaca atgacccaga tgtggccgac atgaggaggt    13680
cctcttttct tggcaagacat cttgcatacc tatgcagcgt ggcagagata tctagggatg    13740
ggccaagatt agaatcaatg aactctctag agaggctcga gtcactaaag agttacctgg    13800
aactcacatt tcttgatgac ccggtactga ggtacagtca gttgactggc ctagtcatca    13860
aagtattccc atctactttg acctatatcc ggaagtcatc tataaaagtg ttaaggacaa    13920
gaggtatagg agtccctgaa gtcttagaag attgggatcc cgaggcagat aatgcactgt    13980
tagatggtat cgcggcagaa atacaacaga atattccttt gggacatcag actagagccc    14040 cttttttgggg gttgagagta tccaagtcac aggtactgcg tctccggggg tacaaggaga    14100
tcacaagagg tgagataggc agatcaggcg ttggtctgac gttaccattc gatggaagat    14160
atctatctca ccagctgagg ctcttttggca tcaacagtac tagctgcttg aaagcacttg    14220
aacttaccta cctattgagc cccttagttg acaaggataa agataggcta tatttagggg    14280
aaggagctgg ggccatgctt tcctgttatg acgctactct tggcccatgc atcaactatt    14340
ataactcagg ggtatactct tgtgatgtca atgggcagag agagttaaat atatatcctg    14400
ctgaggtggc actggtggga aagaaattaa acaatgttac tagtctgggt caaagagtta    14460
aagtgttatt caacgggaat cctggctcga catggattgg aaatgatgag tgtgaggctt    14520
tgatttggaa tgaattgcag aatagctcga taggcctagt ccactgtgac atggaggag    14580 gagatcataa ggatgatcaa gttgtactgc atgagcatta cagtgtaatc cggatcgcgt    14640
atctggtggg ggatcgagac gttgtgctta agcaagat tgctcctagg ctgggcacgg    14700
attggaccag gcagctcagc ctatatctga gatactggga cgaggttaac ctaatagtgc    14760
```

-continued

```
ttaaaacatc taaccctgct tccacagaga tgtatctcct atcgaggcat cccaaatctg    14820
acattataga ggacagcaag acggtgttag ctagtctcct cccttttgtca aaagaagata   14880 gcatcaagat agaaaagtgg atcttaatag agaaggcaaa ggctcacgaa tgggttactc    14940
gggaattgag agaaggaagc tcttcatcag ggatgcttag accttaccat caagcactgc    15000
agacgtttgg ctttgaacca aacttgtata aattgagcag agatttcttg tccaccatga    15060
acatagctga tacacacaac tgcatgatag ctttcaacag ggttttgaag gatcaatct     15120 tcgaatgggc tagaataact gagtcagata aaaggcttaa actaactggt aagtatgacc    15180
tgtatcctgt gagagattca ggcaaattga agacagtttc tagaagactt gtgctatctt    15240
ggatatcttt atctatgtcc acaagattgg taactgggtc attccctgac cagaagtttg    15300
aagcaagact tcaattggga atagtttcat tatcatcccg tgaaatcagg aacctgaggg    15360
ttatcacaaa aactttatta gaccggtttg aggatattat acatagtata acgtacagat    15420
tcctcaccaa agaaataaag attttgatga agattttagg ggcagtcaag atgttcgggg    15480
ccaggcaaaa tgaatacacg accgtgattg atgatggatc actgggtgat atcgagccat    15540
atgacagctc gtaataatta gtccctatcg tgcagaacga tcgaagctcc gcggtacctg    15600
gaagtcttgg actgatccat atgacaatag taagaaaaac ttacaagaag acaagaaaat    15660
ttaaaagaat acatatctct taaactcttg tctggt                              15696
```

<210> SEQ ID NO 14
<211> LENGTH: 21
<212> TYPE: RNA
<213> ORGANISM: Artificial
<220> FEATURE:
<223> OTHER INFORMATION: siRNA:Sense strand

<400> SEQUENCE: 14
gguucagcau caaauaugaa g    21

<210> SEQ ID NO 15
<211> LENGTH: 21
<212> TYPE: RNA
<213> ORGANISM: Artificial
<220> FEATURE:
<223> OTHER INFORMATION: siRNA:Anti-sense strand

<400> SEQUENCE: 15
ucauauuuga ugcugaacca u    21

<210> SEQ ID NO 16
<211> LENGTH: 21
<212> TYPE: RNA
<213> ORGANISM: Artificial
<220> FEATURE:
<223> OTHER INFORMATION: siRNA:Sense strand

<400> SEQUENCE: 16
gguccagaca ugaauucaaa g    21

<210> SEQ ID NO 17
<211> LENGTH: 21
<212> TYPE: RNA
<213> ORGANISM: Artificial
<220> FEATURE:
<223> OTHER INFORMATION: siRNA:Anti-sense strand

<400> SEQUENCE: 17
uugaauucau gucuggacca u    21

```
<210> SEQ ID NO 18
<211> LENGTH: 20
<212> TYPE: DNA
<213> ORGANISM: Artificial
<220> FEATURE:
<223> OTHER INFORMATION: Primer

<400> SEQUENCE: 18
ggaagcatcg aattctggga                                                 20

<210> SEQ ID NO 19
<211> LENGTH: 20
<212> TYPE: DNA
<213> ORGANISM: Artificial
<220> FEATURE:
<223> OTHER INFORMATION: Primer

<400> SEQUENCE: 19
cggagcagca ttccaaggct                                                 20

<210> SEQ ID NO 20
<211> LENGTH: 20
<212> TYPE: DNA
<213> ORGANISM: Artificial
<220> FEATURE:
<223> OTHER INFORMATION: Primer

<400> SEQUENCE: 20
tgagccgtct ttccaccagg                                                 20

<210> SEQ ID NO 21
<211> LENGTH: 20
<212> TYPE: DNA
<213> ORGANISM: Artificial
<220> FEATURE:
<223> OTHER INFORMATION: Primer

<400> SEQUENCE: 21
acatggtctc cagactccac                                                 20

<210> SEQ ID NO 22
<211> LENGTH: 20
<212> TYPE: DNA
<213> ORGANISM: Artificial
<220> FEATURE:
<223> OTHER INFORMATION: Primer

<400> SEQUENCE: 22
agcatccgac tgtaaagaat                                                 20

<210> SEQ ID NO 23
<211> LENGTH: 20
<212> TYPE: DNA
<213> ORGANISM: Artificial
<220> FEATURE:
<223> OTHER INFORMATION: Primer

<400> SEQUENCE: 23
cctctccaca gttatagaag                                                 20

<210> SEQ ID NO 24
<211> LENGTH: 20
<212> TYPE: DNA
<213> ORGANISM: Artificial
<220> FEATURE:
<223> OTHER INFORMATION: Primer
```

```
<400> SEQUENCE: 24
aagaccctaa gaggacgaag                                                      20

<210> SEQ ID NO 25
<211> LENGTH: 25
<212> TYPE: DNA
<213> ORGANISM: Artificial
<220> FEATURE:
<223> OTHER INFORMATION: Primer

<400> SEQUENCE: 25
actcccatgg cgtaactcca tagtg                                                25

<210> SEQ ID NO 26
<211> LENGTH: 18
<212> TYPE: DNA
<213> ORGANISM: Artificial
<220> FEATURE:
<223> OTHER INFORMATION: Primer

<400> SEQUENCE: 26
actgttgctg gggaatgg                                                        18

<210> SEQ ID NO 27
<211> LENGTH: 19
<212> TYPE: DNA
<213> ORGANISM: Artificial
<220> FEATURE:
<223> OTHER INFORMATION: Primer

<400> SEQUENCE: 27
ccaagttcaa agctgctgg                                                       19

<210> SEQ ID NO 28
<211> LENGTH: 22
<212> TYPE: DNA
<213> ORGANISM: Artificial
<220> FEATURE:
<223> OTHER INFORMATION: Primer

<400> SEQUENCE: 28
ttctggcctc tgtgaagtag tg                                                   22

<210> SEQ ID NO 29
<211> LENGTH: 20
<212> TYPE: DNA
<213> ORGANISM: Artificial
<220> FEATURE:
<223> OTHER INFORMATION: Primer

<400> SEQUENCE: 29
gtgaaaccat ggtgcagatg                                                      20

<210> SEQ ID NO 30
<211> LENGTH: 24
<212> TYPE: DNA
<213> ORGANISM: Artificial
<220> FEATURE:
<223> OTHER INFORMATION: Primer

<400> SEQUENCE: 30
aggaatactg aatgtggact ttcc                                                 24

<210> SEQ ID NO 31
<211> LENGTH: 23
<212> TYPE: DNA
```

-continued

<213> ORGANISM: Artificial
<220> FEATURE:
<223> OTHER INFORMATION: Primer

<400> SEQUENCE: 31
tcccttgatt aacagaagac ctg                                    23

<210> SEQ ID NO 32
<211> LENGTH: 39
<212> TYPE: DNA
<213> ORGANISM: Artificial
<220> FEATURE:
<223> OTHER INFORMATION: Primer

<400> SEQUENCE: 32
actagctagc ttagacgctg gattttttc gggtagtgg                    39

<210> SEQ ID NO 33
<211> LENGTH: 30
<212> TYPE: DNA
<213> ORGANISM: Artificial
<220> FEATURE:
<223> OTHER INFORMATION: Primer

<400> SEQUENCE: 33
gtccaccggt cttacgcaca agagttccgt                             30

<210> SEQ ID NO 34
<211> LENGTH: 35
<212> TYPE: DNA
<213> ORGANISM: Artificial
<220> FEATURE:
<223> OTHER INFORMATION: Primer

<400> SEQUENCE: 34
agtacctagg cgcatgtaca acatgatgga gacgg                       35

<210> SEQ ID NO 35
<211> LENGTH: 33
<212> TYPE: DNA
<213> ORGANISM: Artificial
<220> FEATURE:
<223> OTHER INFORMATION: Primer

<400> SEQUENCE: 35
gtccgacgtc ctcacatgtg tgagagggc agt                          33

<210> SEQ ID NO 36
<211> LENGTH: 40
<212> TYPE: DNA
<213> ORGANISM: Artificial
<220> FEATURE:
<223> OTHER INFORMATION: Primer

<400> SEQUENCE: 36
actagctagc ggttccccat ggcgggacac ctggcttcgg                  40

<210> SEQ ID NO 37
<211> LENGTH: 35
<212> TYPE: DNA
<213> ORGANISM: Artificial
<220> FEATURE:
<223> OTHER INFORMATION: Primer

<400> SEQUENCE: 37
ggtccacgcg ttcagtttga atgcatggga gagcc                       35

<210> SEQ ID NO 38
<211> LENGTH: 15702
<212> TYPE: DNA
<213> ORGANISM: Artificial
<220> FEATURE:
<223> OTHER INFORMATION: Full length genome cDNA of Sendai virus
      vector-version2

<400> SEQUENCE: 38

| | | | | | |
|---|---|---|---|---|---|
| accaaacaag | agaagaaaca | tgtatggaat | atataatgaa | gttagacagg | attttagggt | 60 |
| caaagtatcc | accctgagga | gcaggttcca | gatccttttc | tttgctgcca | aagttcacga | 120 |
| tggccgggtt | gttgagcacc | ttcgatacat | ttagctctag | gaggagcgaa | agtattaata | 180 |
| agtcgggagg | aggtgctgtt | atccccggcc | agaggagcac | agtctcagtg | ttcatactag | 240 |
| gcccaagtgt | gactgatgat | gcagacaagt | tattcattgc | aacaaccttc | ctagctcact | 300 |
| cattggacac | agataagcag | cactctcaga | gaggagggtt | cctcgtctct | ctgcttgcca | 360 |
| tggcttacag | tagtccagaa | ttgtacttga | caacaaacgg | agtaaacgcc | gatgtcaaat | 420 |
| atgtgatcta | caacatagag | aaagacccta | gaggacgaa | gacagacgga | ttcattgtga | 480 |
| agacgagaga | tatggaatat | gagaggacca | cagaatggct | gtttggacct | atggtcaaca | 540 |
| agagcccact | cttccagggt | caacgggatg | ctgcagaccc | tgacacactc | cttcaaatct | 600 |
| atgggtatcc | tgcatgccta | ggagcaataa | ttgtccaagt | ctggattgtg | ctggtgaagg | 660 |
| ccatcacaag | cagcgccggc | ttaaggaaag | ggttcttcaa | caggttagag | gcgttcagac | 720 |
| aagacggcac | cgtgaaaggt | gccttagttt | tcactgggga | gacagttgag | gggataggct | 780 |
| cggttatgag | atctcagcaa | agccttgtat | ctctcatggt | tgagacccct | gtgactatga | 840 |
| atactgcaag | atctgatctc | accacattag | agaagaacat | ccagatcgtt | gggaactaca | 900 |
| tccgagatgc | agggctggct | tccttcatga | acactattaa | atatgggtg | gagacaaaga | 960 |
| tggcagctct | aacgttgtca | aacctgaggc | ccgatattaa | taagcttaga | agcctcatag | 1020 |
| acacctacct | gtcaaaaggc | cccagagctc | cctttatctg | tatcctcaag | gaccctgttc | 1080 |
| atggtgaatt | tgctccaggc | aattatcctg | cactatggag | ttacgccatg | ggagtcgccg | 1140 |
| tcgtacagaa | caagtcaatg | cagcagtacg | tcacagggag | gacataccctt | gatatggaaa | 1200 |
| tgttcttact | aggacaagcc | gtggcaaagg | atgctgaatc | gaagatcagc | agtgccttgg | 1260 |
| aagatgagtt | aggagtgacg | gatacagcca | aggagaggct | cagacatcat | ctggcaaact | 1320 |
| tgtccggtgg | ggatggtgct | taccacaaac | caacaggcgg | tggtgcaatt | gaggtagctc | 1380 |
| tagacaatgc | cgatatcgac | ctggaaacag | aagctcatgc | ggaccaggac | gctagggggtt | 1440 |
| ggggtggaga | tagtggtgaa | agatgggcac | gtcaggtgag | tggtggccac | tttgtcacac | 1500 |
| tacatgggc | tgaacggtta | gaggaggaaa | ccaatgatga | ggatgtatca | gacatagaga | 1560 |
| gaagaatagc | catgagactc | gcagagagac | ggcaagagga | ttctgcaacc | catggagatg | 1620 |
| aaggccgcaa | taacggtgtt | gatcacgaag | aagatgacga | tgccgcagca | gcagctggga | 1680 |
| taggaggaat | ctaggatcat | acgaggcctc | aaggtacttg | atccgcagta | agaaaaactt | 1740 |
| agggtgaaag | ttcatccacc | gatcggctca | ggcaaggcca | cacccaaccc | caccgaccac | 1800 |
| acccagcagt | cgagacagcc | acggcttcgg | ctacacttac | cgcatggatc | aagatgcctt | 1860 |
| cattcttaaa | gaagattctg | aagttgagag | gaaggcgcca | ggaggacgag | agtcgctctc | 1920 |
| ggatgttatc | ggattcctcg | atgctgtcct | gtcgaatgaa | ccaactgaca | tcggagggga | 1980 |
| cagaagctgg | ctccacaaca | ccatcaacac | tccccaagga | ccaggctctg | ctcatagagc | 2040 |
| caaaagtgag | ggcgaaggag | aagtctcaac | accgtcgacc | caagataatc | gatcaggtga | 2100 |

```
ggagagtaga gtctctggga gaacaagcaa gccagaggca gaagcacatg ctggaaacct   2160
tgataaacaa aatatacact gggcctttag gggaagaact ggtacaaact ctgtatctca   2220
ggatctggac gatggaggag actccggaat ccttgaaaat cctccaaatg agagaggata   2280
tccgagatca ggtattgaag atgaaaacag agagatggct gcgcaccctg ataagagggg   2340
agaagaccaa gctgaaggac ttccagaaga ggtacgagga ggtacatccc tacctgatga   2400
aggagaaggt ggagcaagta ataatggaag aagcatggag cctggcagct cacatagtgc   2460
aagagtaact ggggtcctgg tgattcctag ccccgaactt gaagaggctg tgctacggag   2520
gaacaaaaga agacctacca acagtgggtc caaacctctt actccagcaa ccgtgcctgg   2580
cacccggtcc ccaccgctga atcgttacaa cagcacaggg tcaccaccag gaaaaccccc   2640
atctacacag gatgagcaca tcaactctgg ggacaccccc gccgtcaggg tcaaagaccg   2700
gaaaccatca ataggggactc gctctgtctc agattgtcca gccaacggcc gcccaatcca   2760
tccgggtata gagaccgact caacaaaaaa gggcatagga gagaacacat catctatgaa   2820
agatatggct acattgttga cgagtcttgg tgtaatccag tctgctcaag aattcgagtc   2880
atcccgagac gcgagttatg tgtttgcaag acgtgcccta aagtctgcaa actatgcaga   2940
gatgacattc aatgtatgcg gcctgatcct ttctgccgag aaatcttccg ctcgtaaggt   3000
agatgagaac aaacaactgc tcaaacagat ccaagagagc gtggaatcat tccgggatat   3060
ttacaagaga ttctctgagt atcagaaaga acagaactca ttgctgatgt ccaacctatc   3120
tacacttcat atcatcacag atagaggtgg caagactgac aacacagact cccttacaag   3180
gtccccctcc gtttttgcaa aatcaaaaga gaacaagact aaggctacca ggtttgaccc   3240
atctatggag accttagaag atatgaagta caaaccggac ctaatccgag aggatgaatt   3300
tagagatgag atccgcaacc cggtgtacca agagagggac acagaaccca gggcctcaaa   3360
cgcatcacgt ctcttcccct ccaaagagaa gcacacaatg cactctctca ggctcgtcat   3420
agagagcagt cccctaagca gagctgagaa agcagcatat gtgaaatcat tatccaagtg   3480
caagacagac caagaggtta aggcagtcat ggaactcgta gaagaggaca tagagtcact   3540
gaccaactag atcccgggtg aggcatccca ccatcctcag tcacagagag acccaatcta   3600
ccatcagcat cagccagtaa agattaagaa aaacttaggg tgaaagaaat ttcaccgcta   3660
gcacctaggt ctgacatggc tgtcagcgac gcgctgctcc catctttctc cacgttcgcg   3720
tctggcccgg cggaagggaa gaagacactg cgtcaagcag gtgccccgaa taaccgctgg   3780
cgggaggagc tctcccacat gaagcgactt ccccccagtgc ttcccggccg ccccctatgac   3840 ctggcggcgg cgaccgtggc cacagacctg gagagcggcg gagccggtgc ggcttgcggc   3900
ggtagcaacc tggcgcccct acctcggaga gagaccgagg agttcaacga tctcctggac   3960
ctggacttta ttctctccaa ttcgctgacc catcctccgg agtcagtggc cgccaccgtg   4020
tcctcgtcag cgtcagcctc ctcttcgtcg tcgccgtcga gcagcggccc tgccagcgcg   4080
ccctccacct gcagcttcac ctatccgatc cgggccggga acgacccggg cgtggcgccg   4140
ggcggcacgg gcggaggcct cctctatggc agggagtccg ctccccctcc gacggctccc   4200
ttcaacctgg cggacatcaa cgacgtgagc ccctcgggcg gcttcgtggc cgagctcctg   4260
cggccagaat tggaccccgt gtacattccg ccgcagcagc cgcagccgcc aggtggcggg   4320
ctgatgggca agttcgtgct gaaggcgtcg ctgagcgccc ctggcagcga gtacggcagc   4380
ccgtcggtca tcagcgtcag caaaggcagc cctgacggca gccacccggt ggtggtggcg   4440
ccctacaacg gcgggccgcc gcgcacgtgc cccaagatca agcaggaggc ggtctcttcg   4500
```

```
tgcacccact tgggcgctgg acccctctc agcaatggcc accggccggc tgcacacgac   4560
ttcccctgg ggcggcagct ccccagcagg actacccga ccctgggtct tgaggaagtg    4620
ctgagcagca gggactgtca ccctgccctg ccgcttcctc ccggcttcca tccccacccg  4680
gggcccaatt acccatcctt cctgcccgat cagatgcagc cgcaagtccc gccgctccat  4740
taccaagagc tcatgccacc cggttcctgc atgccagagg agcccaagcc aaagagggga  4800
agacgatcgt ggccccggaa aaggaccgcc acccacactt gtgattacgc gggctgcggc  4860
aaaacctaca caaagagttc ccatctcaag gcacacctgc gaacccacac aggtgagaaa  4920
ccttaccact gtgactggga cggctgtgga tggaaattcg cccgctcaga tgaactgacc  4980
aggcactacc gtaaacacac ggggcaccgc ccgttccagt gccaaaaatg cgaccgagca  5040
ttttccaggt cggaccacct cgccttacac atgaagaggc atttttaaag acgtcgatta  5100
agaaaaactt agggtgaaag ttcatcgcgg ccgcttgcta gcggttcccc atggcgggac  5160
acctggcttc ggatttcgcc ttctcgcccc ctccaggtgg tggaggtgat gggccagggg  5220
ggccggagcc gggctgggtt gatcctcgga cctggctaag cttccaaggc cctcctggag  5280
ggccaggaat cgggccgggg gttgggccag gctctgaggt gtggggatt ccccatgcc    5340
ccccgccgta tgagttctgt gggggatgg cgtactgtgg ccccaggtt ggagtggggc    5400
tagtgcccca aggcggcttg gagacctctc agcctgaggg cgaagcagga gtcgggtgg   5460
agagcaactc cgatggggcc tccccggagc cctgcaccgt caccctggt gccgtgaagc   5520
tggagaagga gaagctggag caaaaccgg aggagtccca ggacatcaaa gctctgcaga   5580
aagaactcga gcaatttgcc aagctcctga agcagaagag gatcaccctg gatatacac   5640
aggccgatgt gggctcacc ctgggggttc tattgggaa ggtattcagc caaacgacca    5700
tctgccgctt tgaggctctg cagcttagct tcaagaacat gtgtaagctg cggcccttgc  5760
tgcagaagtg ggtggaggaa gctgacaaca atgaaaatct tcaggagata tgcaaagcag  5820
aaaccctcgt gcaggcccga aagagaaagc gaaccagtat cgagaaccga gtgagaggca  5880
acctggagaa tttgttcctg cagtgcccga accccacact gcagcagatc agccacatcg  5940
cccagcagct tgggctcgag aaggatgtgg tccgagtgtg gttctgtaac cggcgccaga  6000
agggcaagcg atcaagcagc gactatgcac aacgagagga ttttgaggct gctgggtctc  6060
cttttctcagg gggaccagtg tccttttcctc tggccccagg gccccatttt ggtacccag  6120
gctatgggag ccctcacttc actgcactgt actcctcggt cccttttccct gagggggaag  6180
cctttccccc tgtctccgtc accactctgg gctctcccat gcattcaaac tgaacgcgtc  6240
agagacctgc aacaatgtct caagcagaca ccacctggca gtcggagcca ccgggtcact  6300
ccttgtctta aataagaaaa acttagggat aaagtccctt agatctagcc taggcgcatg  6360
tacaacatga tggagacgga gctgaagccg ccgggcccgc agcaaacttc gggggcggc   6420
ggcggcaact ccaccgcggc ggcggccggc ggcaaccaga aaaacagccc ggaccgcgtc  6480
aagcggccca tgaatgcctt catggtgtgg tcccgcgggc agcggcgcaa gatggcccag  6540
gagaaccca agatgcacaa ctcggagatc agcaagcgcc tggcgccga gtggaaactt    6600
ttgtcggaga cggagaagcg gccgttcatc gacgaggcta gcggctgcg agcgctgcac   6660
atgaaggagc acccggatta taaataccgg ccccggcgga aaaccaagac gctcatgaag  6720
aaggataagt acacgctgcc cggcgggctg ctggcccccg gcggcaatag catggcgagc  6780
ggggtcgggg tggcgccgg cctgggcgcg ggcgtgaacc agcgcatgga cagttacgcg   6840
cacatgaacg gctggagcaa cggcagctac agcatgatgc aggaccagct gggctacccg  6900
```

```
cagcacccgg gcctcaatgc gcacggcgca gcgcagatgc agcccatgca ccgctacgac   6960
gtgagcgccc tgcagtacaa ctccatgacc agctcgcaga cctacatgaa cggctcgccc   7020
acctacagca tgtcctactc gcagcagggc acccctggca tggctcttgg ctccatgggt   7080
tcggtggtca agtccgaggc cagctccagc cccctgtgg ttacctcttc ctcccactcc    7140
agggcgccct gccaggccgg ggacctccgg gacatgatca gcatgtatct ccccggcgcc   7200
gaggtgccgg aacccgccgc ccccagcaga cttcacatgt cccagcacta ccagagcggc   7260
ccggtgcccg gcacggccat taacggcaca ctgcccctct cacacatgtg aggacgtcag   7320
atctgtatat aataagaaaa acttagggtg aaagtgaggt tgcgcggtat tttagctagc   7380
ttagacgctg gattttttc gggtagtgga aaaccagcag cctcccgcga cgatgcccct    7440
caacgttagc ttcaccaaca ggaactatga cctcgactac gactcggtgc agccgtattt   7500
ctactgcgac gaggaggaga acttctacca gcagcagcag cagagcgagc tgcagccccc   7560
ggcgcccagc gaggatatct ggaagaaatt cgagctgctg cccacccgc ccctgtcccc    7620 tagccgccgc tccgggctct gctcgccctc ctacgttgcg gtcacaccct tctcccttcg   7680
gggagacaac gacggcggtg gcgggagctt ctccacggcc gaccagctgg agatggtgac   7740
cgagctgctg ggaggagaca tggtgaacca gagtttcatc tgcgacccgg acgacgagac   7800
cttcatcaaa aacatcatca tccaggactg tatgtggagc ggcttctcgg ccgccgccaa   7860
gctcgtctca gagaagctgg cctcctacca ggctgcgcgc aaagacagcg gcagcccgaa   7920
ccccgcccgc ggccacagcg tctgctccac ctccagcttg tacctgcagg atctgagcgc   7980
cgccgcctca gagtgcatcg acccctcggt ggtcttcccc taccctctca acgacagcag   8040
ctcgcccaag tcctgcgcct cgcaagactc cagcgccttc tctccgtcct cggattctct   8100
gctctcctcg acggagtcct ccccgcaggg cagccccgag ccctggtgc tccatgagga    8160 gacaccgccc accaccagca gcgactctga ggaggaacaa gaagatgagg aagaaatcga   8220
tgttgtttct gtggaaaaga ggcaggctcc tggcaaaagg tcagagtctg gatcaccttc   8280
tgctggaggc cacagcaaac ctcctcacag cccactggtc ctcaagaggt gccacgtctc   8340
cacacatcag cacaactacg cagcgcctcc ctccactcgg aaggactatc ctgctgccaa   8400
gagggtcaag ttggacagtg tcagagtcct gagacagatc agcaacaacc gaaaatgcac   8460
cagccccagg tcctcggaca ccgaggagaa tgtcaagagg cgaacacaca acgtcttgga   8520
gcgccagagg aggaacgagc taaaacggag cttttttgcc ctgcgtgacc agatcccgga   8580
gttggaaaac aatgaaaagg cccccaaggt agttatcctt aaaaaagcca cagcatacat   8640
cctgtccgtc caagcagagg agcaaaagct catttctgaa gaggacttgt tgcggaaacg   8700
acgagaacag ttgaaacaca aacttgaaca gctacggaac tcttgtgcgt aagaccggtg   8760
tcggctttgc tgacactaga gtcatctccg aacatccaca atatctctca gtctcttacg   8820
tctctcacag tattaagaaa aacccagggt gaatgggaag cttgccatag gtcatggatg   8880
ggcaggagtc ctcccaaaac ccttctgaca tactctatcc agaatgccac ctgaactctc   8940
ccatagtcag ggggaagata gcacagttgc acgtcttgtt agatgtgaac cagccctaca   9000
gactaaagga cgacagcata ataaatatta caaagcacaa aattaggaac ggaggattgt   9060
cccctcgtca aattaagatc aggtctctgg gtaaggctct tcaacgcaca ataaggatt   9120 tagaccgata caccttgaa ccgtacccaa cctactctca ggaattactt aggcttgata    9180
taccagagat atgtgacaaa atccgatccg tcttcgcggt ctcggatcgg ctgaccaggg   9240
agttatctag tgggttccag gatctttggt tgaatatctt caagcaacta ggcaatatag   9300
```

```
aaggaagaga ggggtacgat ccgttgcagg atatcggcac catcccggag ataactgata   9360
aatacagcag gaatagatgg tataggccat tcctaacttg gttcagcatc aaatatgaca   9420
tgcggtggat gcagaagacc agaccggggg gaccCctcga tacctctaat tcacataacc   9480
tcctagaatg caaatcatac actctagtaa catacggaga tcttatcatg atactgaaca   9540
agttgacatt gacagggtat atcctaaccc ctgagctggt cttgatgtat tgtgatgttg   9600
tagagggaag gtggaatatg tctgctgcag ggcatctaga taagaagtcc attgggataa   9660
caagcaaagg tgaggaatta tgggaactag tggattccct cttctcaagt cttggagagg   9720
aaatatacaa tgtcatcgca ctattggagc ccctatcact tgctctcata caactaaatg   9780
atccagttat acctctacgt ggggcattta tgaggcatgt gttgacagag ctacaggctg   9840
ttttaacaag tagggacgtg tacacagatg ctgaagcaga cactattgtg gagtcgttac   9900
tcgccatttt ccatggaacc tctattgatg agaaagcaga gatcttttcc ttctttagga   9960
catttggcca ccccagctta gaggctgtca ctgccgccga caaggtaagg gcccatatgt  10020
atgcacaaaa ggcaataaag cttaagaccc tatacgagtg tcatgcagtt ttttgcacta  10080
tcatcataaa tgggtataga gagaggcatg gcggacagtg gccccctgt gacttccctg  10140 atcacgtgtg tctagaacta aggaacgctc aagggtccaa tacggcaatc tcttatgaat  10200
gtgctgtaga caactataca agtttcatag gcttcaagtt tcggaagttt atagaaccac  10260
aactagatga agatctcaca atatatatga aagacaaagc actatccccc aggaaggagg  10320
catgggactc tgtatacccg gatagtaatc tgtactataa agcccagaa tctgaagaga  10380 cccggcggct tattgaagtg ttcataaatg atgagaattt caacccagaa gaaattatca  10440
attatgtgga gtcaggagat tggttgaaag acgagaagtt caacatctcg tacagtctca  10500
aagagaaaga gatcaagcaa gagggtcgtc tattcgcaaa aatgacttat aagatgcgag  10560
ccgtacaggt gctggcagag acactactgg ctaaaggaat aggagagctg ttcagcgaaa  10620
atgggatggt taaggagag atagacctac ttaaaagatt gactactctt tctgtctcag  10680
gagtccccag gactgattca gtgtacaata actctaaatc atcagagaag agaaacgaag  10740
gcatgaaaaa gaagaactct gggggtact gggacgaaaa gaagaggtcc agacatgaat  10800
tcaaggcaac agattcatca acagacggct atgaaacgtt aagttgcttc ctcacaacag  10860
acctcaagaa atactgctta aactggagat ttgaaagtac tgcattgttt ggtcagagat  10920
gcaacgagat atttggcttc aagaccttct ttaactggat gcatccagtc cttgaaaggt  10980
gtacaatata tgttggggat ccttactgtc cagtcgccga ccggatgcat cgacaactcc  11040
aggatcatgc agactctggc attttcatac ataatcctag ggggggcata gaaggttact  11100
gccagaagct gtggaccttca atctcaatca gtgcaatcca cctagcagct gtgagagtgg  11160
gtgtcagggt ctctgcaatg gttcagggtg acaatcaagc tatagccgtg acatcaagag  11220
tacctgtagc tcagacttac aagcagaaga aaaatcatgt ctataaggag atcaccaaat  11280
attttggtgc tctaagacac gtcatgtttt atgtagggca cgagctaaaa ttgaacgaga  11340
ccatcattag tagcaagatg tttgtctata gtaaaagaat atactatgat gggaagattt  11400
taccacagtg cctgaaagcc ttgaccaggt gtgtattctg gtccgagaca ctggtagatg  11460
aaaacagatc tgcttgttcg aacatctcaa catccatagc aaaagctatc gaaaatgggt  11520
attctcctat actaggctac tgcattgcgt tgtataagac ctgtcagcag gtgtgcatat  11580 cactaggat gactataaat ccaactatca gcccgaccgt aagagatcaa tactttaagg  11640
gtaagaattg gctgagatgt gcagtgttga ttccagcaaa tgttggagga ttcaactaca  11700
```

```
tgtctacatc tagatgcttt gttagaaata ttggagaccc cgcagtagca gccctagctg    11760
atctcaaaag attcatcaga gcggatctgt tagacaagca ggtactatac agggtcatga    11820
atcaagaacc cggtgactct agctttctag attgggcttc agacccttat tcatgtaacc    11880
tcccgcattc tcagagtata actacgatta taaagaatat cactgctaga tctgtgctgc    11940
aggaatcccc gaatcctcta ctgtctggtc tcttcaccga gactagtgga gaagaggatc    12000
tcaacctggc ctcgttcctt atggaccgga aagtcatcct gccgagagtg gctcatgaga    12060
tcctgggtaa ttccttaact ggagttaggg aggcgattgc agggatgctt gatacgacca    12120
agtctctagt gagatccagc gttaagaaag gaggattatc atatgggata ttgaggaggc    12180
ttgtcaatta tgatctattg cagtacgaga cactgactag aactctcagg aaaccggtga    12240
aagacaacat cgaatatgag tatatgtgtt cagttgagct agctgtcggt ctaaggcaga    12300
aaatgtggat ccacctaact tacgggagac ccatacatgg gctagaaaca ccagacccgt    12360
tagagctctt gaggggaaca tttatcgaag gttcagaggt gtgcaagctt tgcaggtctg    12420
agggagcaga ccccatctat acatggttct atctccctga caatatagac ctggacacgc    12480
ttacaaacgg atgtccggct ataagaatcc cctattttgg atcagccact gatgaaaggt    12540
cggaagccca actcgggtat gtaagaaatc taagcaaacc cgcaaaggct gccatccgga    12600
tagctatggt gtatacgtgg gcctacggga ctgatgagat atcgtggatg gaagccgctc    12660
ttatagccca acaagagct aatctgagct tagagaatct aaagctgctg actcctgttt    12720
caacctccac taatctatct cataggttga agatacggc aacccagatg aagttctcta    12780
gtgcaacact agtccgtgca agtcggttca taacaatatc aaatgataac atggcactca    12840
aagaagcagg ggagtcgaag gatactaatc tcgtgtatca gcagattatg ctaactgggc    12900
taagcttgtt cgagttcaat atgagatata agaaaggttc cttagggaag ccactgatat    12960
tgcacttaca tcttaataac gggtgctgta taatggagtc cccacaggag gcgaatatcc    13020
ccccaaggtc cacattagat ttagagatta cacaagagaa caataaattg atctatgatc    13080
ctgatccact caaggatgtg gaccttgagc tatttagcaa ggtcagagat gttgtacata    13140
cagttgacat gacttattgg tcagatgatg aagttatcag agcaaccagt atctgtactg    13200
caatgacgat agctgataca atgtctcaat tagatagaga caacctaaaa gagatgatcg    13260
cgctagtaaa tgacgatgat gtcaacagcc tgattactga gtttatggtg attgatgttc    13320 ctttatttg ctcaacgttc gggggtattc tagtcaatca gtttgcatac tcactctacg    13380
gcttaaacat cagaggaagg gaagaaatat ggggacatgt agtccggatt cttaaagata    13440
cctcccacgc agttctaaaa gtcttatcta atgctctatc tcatcccaaa atcttcaaac    13500
gattctggaa tgcaggtgtc gtggaacctg tgtatgggcc taacctctca aatcaggaca    13560
agatactctt ggccctctct gtctgtgaat attctgtgga tctattcatg cacgattggc    13620 aaggggtgt accgcttgag atctttatct gtgacaatga cccagatgtg gccgacatga    13680
ggaggtcctc tttcttggca agacatcttg catacctatg cagcgtggca gagatatcta    13740
gggatgggcc aagattagaa tcaatgaact ctctagagag gctcgagtca ctaaagagtt    13800
acctggaact cacatttctt gatgacccgg tactgaggta cagtcagttg actggcctag    13860
tcatcaaagt attcccatct acttgacct atatccggaa gtcatctata aaagtgttaa    13920
ggacaagagg tataggagtc cctgaagtct tagaagattg ggatcccgag gcagataatg    13980
cactgttaga tggtatcgcg gcagaaatac aacagaatat tccttgggga catcagacta    14040
gagccccttt ttgggggttg agagtatcca agtcacaggt actgcgtctc cgggggtaca    14100
```

```
aggagatcac aagaggtgag ataggcagat caggcgttgg tctgacgtta ccattcgatg    14160
gaagatatct atctcaccag ctgaggctct ttggcatcaa cagtactagc tgcttgaaag    14220
cacttgaact tacctaccta ttgagcccct tagttgacaa ggataaagat aggctatatt    14280
taggggaagg agctggggcc atgctttcct gttatgacgc tactcttggc ccatgcatca    14340
actattataa ctcaggggta tactcttgtg atgtcaatgg gcagagagag ttaaatatat    14400
atcctgctga ggtggcactg gtgggaaaga aattaaacaa tgttactagt ctgggtcaaa    14460
gagttaaagt gttattcaac gggaatcctg gctcgacatg gattggaaat gatgagtgtg    14520
aggctttgat ttggaatgaa ttgcagaata gctcgatagg cctagtccac tgtgacatgg    14580
agggaggaga tcataaggat gatcaagttg tactgcatga gcattacagt gtaatccgga    14640
tcgcgtatct ggtggggat cgagacgttg tgcttataag caagattgct cctaggctgg     14700
gcacggattg gaccaggcag ctcagcctat atctgagata ctgggacgag gttaacctaa    14760
tagtgcttaa aacatctaac cctgcttcca cagagatgta tctcctatcg aggcatccca    14820
aatctgacat tatagaggac agcaagacgg tgttagctag tctcctccct ttgtcaaaag    14880
aagatagcat caagatagaa aagtggatct taatagagaa ggcaaaggct cacgaatggg    14940
ttactcggga attgagagaa ggaagctctt catcagggat gcttagacct taccatcaag    15000
cactgcagac gtttggcttt gaaccaaact tgtataaatt gagcagagat ttcttgtcca    15060
ccatgaacat agctgataca cacaactgca tgatagcttt caacagggtt ttgaaggata    15120
caatcttcga atgggctaga ataactgagt cagataaaag gcttaaacta actggtaagt    15180
atgacctgta tcctgtgaga gattcaggca aattgaagac agtttctaga agacttgtgc    15240
tatcttggat atctttatct atgtccacaa gattggtaac tgggtcattc cctgaccaga    15300
agtttgaagc aagacttcaa ttgggaatag tttcattatc atcccgtgaa atcaggaacc    15360
tgagggttat cacaaaaaact ttattagacc ggtttgagga tattatacat agtataacgt    15420
acagattcct caccaaagaa ataaagattt tgatgaagat tttaggggca gtcaagatgt    15480
tcggggccag gcaaaatgaa tacacgaccg tgattgatga tggatcactg ggtgatatcg    15540
agccatatga cagctcgtaa taattagtcc ctatcgtgca gaacgatcga agctccgcgg    15600
tacctggaag tcttggactg atccatatga caatagtaag aaaaacttac aagaagacaa    15660
gaaaatttaa aagaatacat atctcttaaa ctcttgtctg gt                       15702
```

<210> SEQ ID NO 39
<211> LENGTH: 63
<212> TYPE: DNA
<213> ORGANISM: Artificial
<220> FEATURE:
<223> OTHER INFORMATION: Oligo DNA for introducing target sequence of
      mir-302a

<400> SEQUENCE: 39

```
ccggttatca ccaaaacatg gaagcactta cgattcacca aaacatggaa gcacttaggt    60
acc                                                                  63
```

<210> SEQ ID NO 40
<211> LENGTH: 53
<212> TYPE: DNA
<213> ORGANISM: Artificial
<220> FEATURE:
<223> OTHER INFORMATION: Oligo DNA for introducing target sequence of
      mir-302a

<400> SEQUENCE: 40
taagtgcttc catgtttgg tgaatcgtaa gtgcttccat gttttggtga taa    53

<210> SEQ ID NO 41
<211> LENGTH: 51
<212> TYPE: DNA
<213> ORGANISM: Artificial
<220> FEATURE:
<223> OTHER INFORMATION: Oligo DNA for introducing target sequence of
      mir-302a

<400> SEQUENCE: 41
tcaccaaaac atggaagcac ttacgattca ccaaaacatg aagcactta a    51

<210> SEQ ID NO 42
<211> LENGTH: 61
<212> TYPE: DNA
<213> ORGANISM: Artificial
<220> FEATURE:
<223> OTHER INFORMATION: Oligo DNA for introducing target sequence of
      mir-302a

<400> SEQUENCE: 42
ccggttaagt gcttccatgt tttggtgaat cgtaagtgct tccatgtttt ggtgaggtac    60
c    61

<210> SEQ ID NO 43
<211> LENGTH: 6576
<212> TYPE: DNA
<213> ORGANISM: Artificial
<220> FEATURE:
<223> OTHER INFORMATION: pNK15 (vector used to making Sendai virus
      vector having target sequence of mir-302a)

<400> SEQUENCE: 43
atcggcacca tcccggagat aactgataaa tacagcagga atagatggta taggccattc    60
ctaacttggt tcagcatcaa atatgacatg cggtggatgc agaagaccag accgggggga    120
cccctcgata cctctaattc acataacctc ctagaatgca aatcatacac tctagtaaca    180
tacggagatc ttatcatgat actgaacaag ttgacattga cagggtatat cctaacccct    240
gagctggtct tgatgtattg tgatgttgta gagggaaggt ggaatatgtc tgctgcaggg    300
catctagata agaagtccat gggataaca agcaaaggtg aggaattatg ggaactagtg    360
gattccctct tctcaagtct tggagaggaa atatacaatg tcatcgcact attggagccc    420
ctatcacttg ctctcataca actaaatgat ccagttatac ctctacgtgg ggcatttatg    480
aggcatgtgt tgacagagct acaggctgtt ttaacaagta gggacgtgta cacagatgct    540
gaagcagaca ctattgtgga gtcgttactc gccattttcc atggaacctc tattgatgag    600
aaagcagaga tcttttcctt ctttaggaca tttggccacc ccagcttaga ggctgtcact    660
gccgccgaca aggtaagggc ccatatgtat gcacaaaagg caataaagct taagacccta    720
tacgagtgtc atgcagtttt ttgcactatc atcataaatg ggtatagaga gaggcatggc    780
ggacagtggc cccctgtga cttccctgat cacgtgtgtc tagaactaag gaacgctcaa    840
gggtccaata cggcaatctc ttatgaatgt gctgtagaca actatacaag tttcataggc    900
ttcaagtttc ggaagtttat agaaccacaa ctagatgaag atctcacaat atatatgaaa    960
gacaaagcac tatcccccag gaaggaggca tgggactctg tatacccgga tagtaatctg    1020
tactataaag ccccagaatc tgaagagacc cggcggctta ttgaagtgtt cataaatgat    1080
gagaatttca acccagaaga aattatcaat tatgtggagt caggagattg gttgaaagac    1140

```
gagaagttca acatctcgta cagtctcaaa gagaaagaga tcaagcaaga gggtcgtcta    1200
ttcgcaaaaa tgacttataa gatgcgagcc gtacaggtgc tggcagagac actactggct    1260
aaaggaatag gagagctgtt cagcgaaaat gggatggtta aggagagat agacctactt     1320 aaaagattga ctactctttc tgtctcagga gtccccagga ctgattcagt gtacaataac    1380
tctaaatcat cagagaagag aaacgaaggc atgaaaaaga gaactctggg gggtactgg     1440 gacgaaaaga gaggtccag acatgaattc aaggcaacag attcatcaac agacggctat     1500
gaaacgttaa gttgcttcct cacaacagac ctcaagaaat actgcttaaa ctggagattt    1560
gaaagtactg cattgtttgg tcagagatgc aacgagatat ttggcttcaa gaccttcttt    1620
aactggatgc atccagtcct tgaaaggtgt acaatatatg ttggggatcc ttactgtcca    1680
gtcgccgacc ggatgcatcg acaactccag gatcatgcag actctggcat tttcatacat    1740
aatcctaggg ggggcataga aggttactgc cagaagctgt ggaccttaat ctcaatcagt    1800
gcaatccacc tagcagctgt gagagtgggg gtcagggtct ctgcaatggt tcagggtgac    1860
aatcaagcta tagccgtgac atcaagagta cctgtagctc agacttacaa gcagaagaaa    1920
aatcatgtct ataaggagat caccaaatat tttggtgctc taagacacgt catgtttgat    1980
gtagggcacg agctaaaatt gaacgagacc atcattagta gcaagatgtt tgtctatagt    2040
aaaagaatat actatgatgg gaagatttta ccacagtgcc tgaaagcctt gaccaggtgt    2100
gtattctggt ccgagacact ggtagatgaa acagatctg cttgttcgaa catctcaaca     2160
tccatagcaa aagctatcga aaatgggtat tctcctatac taggctactg cattgcgttg    2220
tataagacct gtcagcaggt gtgcatatca ctagggatga ctataaatcc aactatcagc    2280
ccgaccgtaa gagatcaata ctttaagggt aagaattggc tgagatgtgc agtgttgatt    2340
ccagcaaatg ttggaggatt caactacatg tctacatcta gatgctttgt tagaaatatt    2400
ggagaccccg cagtagcagc cctagctgat ctcaaaagat tcatcagagc ggatctgtta    2460
gacaagcagg tactatacag ggtcatgaat caagaacccg gtgactctag ctttctagat    2520
tgggcttcag acccttattc atgtaacctc ccgcattctc agagtataac tacgattata    2580
aagaatatca ctgctagatc tgtgctgcag gaatccccga atcctctact gtctggtctc    2640
ttcaccgaga ctagtggaga agaggatctc aacctggcct cgttccttat ggaccggaaa    2700
gtcatcctgc cgagagtggc tcatgagatc ctgggtaatt ccttaactgg agttagggag    2760
gcgattgcag ggatgcttga tacgaccaag tctctagtga gatccagcgt taagaaagga    2820
ggattatcat atgggatatt gaggaggctt gtcaattatg atctattgca gtacgagaca    2880
ctgactagaa ctctcaggaa accggtgaaa gacaacatcg aatatgagta tatgtgttca    2940
gttgagctag ctgtcggtct aaggcagaaa atgtggatcc acctaactta cgggagaccc    3000
atacatgggc tagaaacacc agacccttta gagctcttga ggggaacatt tatcgaaggt    3060
tcagaggtgt gcaagctttg caggtctgag ggagcagacc ccatctatac atggttctat    3120
ctccctgaca atatagacct ggacacgctt acaaacggat gtccggctat aagaatcccc    3180
tattttggat cagccactga tgaaaggtcg gaagcccaac tcgggtatgt aagaaatcta    3240
agcaaacccg caaaggctgc catccggata gctatggtgt atacgtgggc ctacgggact    3300
gatgagatat cgtggatgga agccgctctt atagcccaaa caagagctaa tctgagctta    3360
gagaatctaa agctgctgac tcctgtttca acctccacta atctatctca taggttgaaa    3420
gatacggcaa cccagatgaa gttctctagt gcaacactag tccgtgcaag tcggttcata    3480
acaatatcaa atgataacat ggcactcaaa gaagcagggg agtcgaagga tactaatctc    3540
```

```
gtgtatcagc agattatgct aactgggcta agcttgttcg agttcaatat gagatataag    3600
aaaggttcct tagggaagcc actgatattg cacttacatc ttaataacgg gtgctgtata    3660
atggagtccc cacaggaggc gaatatcccc ccaaggtcca cattagattt agagattaca    3720
caagagaaca ataaattgat ctatgatcct gatccactca aggatgtgga ccttgagcta    3780
tttagcaagg tcagagatgt tgtacataca gttgacatga cttattggtc agatgatgaa    3840
gttatcagag caaccagtat ctgtactgca atgacgatag ctgatacaat gtctcaatta    3900
gatagagaca acctaaaaga gatgatcgcg ctagtaaatg acgatgatgt caacagcctg    3960
attactgagt ttatggtgat tgatgttcct ttattttgct caacgttcgg gggtattcta    4020
gtcaatcagt ttgcatactc actctacggc ttaaacatca gaggaaggga agaaatatgg    4080
ggacatgtag tccggattct aaagatacc tcccacgcag ttctaaaagt cttatctaat    4140
gctctatctc atcccaaaat cttcaaacga ttctggaatg caggtgtcgt ggaacctgtg    4200
tatgggccta acctctcaaa tcaggacaag atactcttgg ccctctctgt ctgtgaatat    4260
tctgtggatc tattcatgca cgattggcaa gggggtgtac cgcttgagat ctttatctgt    4320
gacaatgacc cagatgtggc cgacatgagg aggtcctctt tcttggcaag acatcttgca    4380
tacctatgca gcgtggcaga gatatctagg gatgggccaa gattagaatc aatgaactct    4440
ctagagaggc tcgagtcact aaagagttac ctggaactca catttcttga tgacccggta    4500
ctgaggtaca gtcagttgac tggcctagtc atcaaagtat tcccatctac tttgacctat    4560
atccggaagt catctatata agtgttaagg acaagaggta taggagtccc tgaagtctta    4620
gaagattggg atcccgaggc agataatgca ctgttagatg gtatcgcggc agaaatacaa    4680
cagaatattc ctttgggaca tcagactaga gcccctttt gggggttgag agtatccaag    4740
tcacaggtac tgcgtctccg ggggtacaag agatcacaa gaggtgagat aggcagatca    4800
ggcgttggtc tgacgttacc attcgatgga agatatctat ctcaccagct gaggctcttt    4860
ggcatcaaca gtactagctg cttgaaagca cttgaactta cctacctatt gagccccta    4920 gttgacaagg ataaagatag gctatattta ggggaaggag ctggggccat gcttcctgt    4980 tatgacgcta ctcttggccc atgcatcaac tattataact caggggtata ctcttgtgat    5040
gtcaatgggc agagagagtt aaatatatat cctgctgagg tggcactggt gggaagaaa    5100 ttaaacaatg ttactagtct gggtcaaaga gttaaagtgt tattcaacgg gaatcctggc    5160
tcgacatgga ttggaaatga tgagtgtgag gctttgattt ggaatgaatt gcagaatagc    5220
tcgataggcc tagtccactg tgacatgagg ggaggagatc ataaggatga tcaagttgta    5280
ctgcatgagc attacagtgt aatccggatc gcgtatctgg tgggggatcg agacgttgtg    5340
cttataagca agattgctcc taggctgggc acggattgga ccaggcagct cagcctatat    5400
ctgagatact gggacgaggt taacctaata gtgcttaaaa catctaaccc tgcttccaca    5460
gagatgtatc tccatcgag gcatcccaaa tctgacatta tagaggacag caagacggtg    5520
ttagctagtc tcctccttt gtcaaaagaa gatagcatca agatagaaaa gtggatctta    5580
atagagaagg caaaggctca cgaatgggtt actcggggaat tgagaaagg aagctcttca    5640 tcagggatgc ttagacctta ccatcaagca ctgcagacgt ttggctttga accaaacttg    5700
tataaattga gcagagattt cttgtccacc atgaacatag ctgatacaca caactgcatg    5760
atagctttca acagggtttt gaaggataca atcttcgaat gggctagaat aactgagtca    5820
gataaaaggc ttaaactaac tggtaagtat gacctgtatc ctgtgagaga ttcaggcaaa    5880
ttgaagacag tttctagaag acttgtgcta tcttggatat ctttatctat gtccacaaga    5940
```

```
ttggtaactg ggtcattccc tgaccagaag tttgaagcaa gacttcaatt gggaatagtt      6000
tcattatcat cccgtgaaat caggaacctg agggttatca caaaaacttt attagaccgg      6060
tttgaggata ttatacatag tataacgtac agattcctca ccaaagaaat aaagattttg      6120
atgaagattt taggggcagt caagatgttc ggggccaggc aaaatgaata cacgaccgtg      6180
attgatgatg gatcactggg tgatatcgag ccatatgaca gctcgtaata attagtccct      6240
atcgtgcaga acgatcgaag ctccgcggta cctggaagtc ttggactgat ccatatgaca      6300
atagtaagaa aaacttacaa gaagacaaga aaatttaaaa gaatacatat ctcttaaact      6360
cttgtctggt gtcctgtttc gaaaacgaaa cagagaacca gtaccagaga aacacacgtt      6420
gtggtatatt acctggttct cgagcaccac caccaccacc actgagatcc ggctgctaac      6480
aaagcccgaa aggaagctga gttggctgct gccaccgctg agcaataact agcataaccc      6540
cttggggcct ctaaacgggt cttgaggggt tttttg                                6576

<210> SEQ ID NO 44
<211> LENGTH: 31
<212> TYPE: DNA
<213> ORGANISM: Artificial
<220> FEATURE:
<223> OTHER INFORMATION: Primer

<400> SEQUENCE: 44
gacagctcgt aatcccgggt ccctatcgtg c                                      31

<210> SEQ ID NO 45
<211> LENGTH: 31
<212> TYPE: DNA
<213> ORGANISM: Artificial
<220> FEATURE:
<223> OTHER INFORMATION: Primer

<400> SEQUENCE: 45
gcacgatagg gacccgggat tacgagctgt c                                      31

<210> SEQ ID NO 46
<211> LENGTH: 15810
<212> TYPE: DNA
<213> ORGANISM: Artificial
<220> FEATURE:
<223> OTHER INFORMATION: Full length genome cDNA of Sendai virus
      vector-version3

<400> SEQUENCE: 46
accaaacaag agaagaaaca tgtatggaat atataatgaa gtttaagaaa aacttagggt       60
caaagtatcc accctgagga gcaggttcca gatcctttc tttgctgcca aagttcacga      120
tggccgggtt gttgagcacc ttcgatacat ttagctctag gaggagcgaa agtattaata      180
agtcgggagg aggtgctgtt atccccggcc agaggagcac agtctcagtg ttcatactag      240
gcccaagtgt gactgatgat gcagacaagt tattcattgc aacaaccttc ctagctcact      300
cattggacac agataagcag cactctcaga gaggagggtt cctcgtctct ctgcttgcca      360
tggcttacag tagtccagaa ttgtacttga caacaaacgg agtaaacgcc gatgtcaaat      420
atgtgatcta caacatagag aaagacccta gaggacgaa gacagacgga ttcattgtga      480
agacgagaga tatggaatat gagaggacca cagaatggct gtttggacct atggtcaaca      540
agagcccact cttccagggt caacgggatg ctgcagaccc tgacactc cttcaaatct      600 atgggtatcc tgcatgccta ggagcaataa ttgtccaagt ctggattgtg ctggtgaagg      660
ccatcacaag cagcgccggc ttaaggaaag ggttcttcaa caggttagag gcgttcagac      720
```

```
aagacggcac cgtgaaaggt gccttagttt tcactgggga gacagttgag gggataggct    780
cggttatgag atctcagcaa agccttgtat ctctcatggt tgagacccct gtgactatga    840
atactgcaag atctgatctc accacattag agaagaacat ccagatcgtt gggaactaca    900
tccgagatgc agggctggct tccttcatga acactattaa atatggggtg gagacaaaga    960
tggcagctct aacgttgtca aacctgaggc ccgatattaa taagcttaga agcctcatag   1020
acacctacct gtcaaaaggc cccagagctc cctttatctg tatcctcaag gaccctgttc   1080
atggtgaatt tgctccaggc aattatcctg cactatggag ttacgccatg ggagtcgccg   1140
tcgtacagaa caagtcaatg cagcagtacg tcacagggag gacataccct gatatggaaa   1200
tgttcttact aggacaagcc gtggcaaagg atgctgaatc gaagatcagc agtgccttgg   1260
aagatgagtt aggagtgacg gatacagcca aggagaggct cagacatcat ctggcaaact   1320
tgtccggtgg ggatggtgct taccacaaac caacaggcgg tggtgcaatt gaggtagctc   1380
tagacaatgc cgatatcgac ctggaaacag aagctcatgc ggaccaggac gctaggggtt   1440
ggggtggaga tagtggtgaa agatgggcac gtcaggtgag tggtggccac tttgtcacac   1500
tacatggggc tgaacggtta gaggaggaaa ccaatgatga ggatgtatca gacatagaga   1560
gaagaatagc catgagactc gcagagagac ggcaagagga ttctgcaacc catggagatg   1620
aaggccgcaa taacgtgtt gatcacgaag aagatgacga tgccgcagca gcagctggga   1680
taggaggaat ctaggatcat acgaggcctc aaggtacttg atccgcagta agaaaaactt   1740
agggtgaaag ttcatccacc gatcggctca ggcaaggcca cacccaaccc caccgaccac   1800
acccagcagt cgagacagcc acggcttcgg ctacacttac cgcatggatc aagatgcctt   1860
cattcttaaa gaagattctg aagttgagag gaggcgccaa ggaggacgag agtcgctctc   1920
ggatgttatc ggattcctcg atgctgtcct gtcgaatgaa ccaactgaca tcggagggga   1980
cagaagctgg ctccacaaca ccatcaacac tccccaagga ccaggctctg ctcatagagc   2040
caaaagtgag ggcgaaggag aagtctcaac accgtcgacc caagataatc gatcaggtga   2100
ggagagtaga gtctctggga gaacaagcaa gccagaggca gaagcacatg ctggaaacct   2160
tgataaacaa aatatacact gggcctttag gggaagaact ggtacaaact ctgtatctca   2220
ggatctggac gatggaggag actccggaat ccttgaaaat cctccaaatg agagaggata   2280
tccgagatca ggtattgaag atgaaaacag agagatggct gcgcaccctg ataagagggg   2340
agaagaccaa gctgaaggac ttccagaaga ggtacgagga ggtacatccc tacctgatga   2400
aggagaaggt ggagcaagta ataatggaag aagcatggag cctggcagct cacatagtgc   2460
aagagtaact ggggtcctgg tgattcctag ccccgaactt gaagaggctg tgctacggag   2520
gaacaaaaga agacctacca acagtgggtc caaacctctt actccagcaa ccgtgcctgg   2580
cacccggtcc ccaccgctga atcgttacaa cagcacaggg tcaccaccag gaaaaccccc   2640
atctacacag gatgagcaca tcaactctgg ggacacccc gccgtcaggg tcaaagaccg   2700
gaaaccatca ataggactc gctctgtctc agattgtcca gccaacggcc gcccaatcca   2760
tccgggtata gagaccgact caacaaaaaa gggcatagga gagaacacat catctatgaa   2820
agatatggct acattgttga cgagtcttgg tgtaatccag tctgctcaag aattcgagtc   2880
atcccgagac gcgagttatg tgtttgcaag acgtgcccta aagtctgcaa actatgcaga   2940
gatgacattc aatgtatgcg gcctgatcct ttctgccgag aaatcttccg ctcgtaaggt   3000
agatgagaac aaacaactgc tcaaacagat ccaagagagc gtggaatcat tccgggatat   3060
ttacaagaga ttctctgagt atcagaaaga acagaactca ttgctgatgt ccaacctatc   3120
```

```
tacacttcat atcatcacag atagaggtgg caagactgac aacacagact cccttacaag    3180
gtcccccctcc gttttttgcaa aatcaaaaga gaacaagact aaggctacca ggtttgaccc    3240
atctatggag accttagaag atatgaagta caaaccggac ctaatccgag aggatgaatt    3300
tagagatgag atccgcaacc cggtgtacca agagagggac acagaaccca gggcctcaaa    3360
cgcatcacgt ctcttcccct ccaaagagaa gcccacaatg cactctctca ggctcgtcat    3420
agagagcagt cccctaagca gagctgagaa agcagcatat gtgaaatcat tatccaagtg    3480
caagacagac caagaggtta aggcagtcat ggaactcgta gaagaggaca tagagtcact    3540
gaccaactag atcccgggtg aggcatccca ccatcctcag tcacagagag acccaatcta    3600
ccatcagcat cagccagtaa agattaagaa aaacttaggg tgaaagaaat ttcaccgcta    3660
gcttagacga tggatttttt tcgggtagtg aaaaccagc agcctcccgc gacgatgccc    3720
ctcaacgtta gcttaccaa caggaactat gacctcgact acgactcggt gcagccgtat    3780
ttctactgcg acgaggagga gaacttctac cagcagcagc agcagagcga gctgcagccc    3840
ccggcgccca gcgaggatat ctggaagaaa ttcgagctgc tgcccacccc gcccctgtcc    3900
cctagccgcc gctccgggct ctgctcgccc tcctacgttg cggtcacacc cttctccctt    3960
cggggagaca acgacggcgg tggcgggagc ttctccacgg ccgaccagct ggagatggtg    4020
accgagctgc tgggaggaga catggtgaac cagagtttca tctgcgaccc ggacgacgag    4080
accttcatca aaaacatcat catccaggac tgtatgtgga gcggcttctc ggccgccgcc    4140
aagctcgtct cagagaagct ggcctcctac caggctgcgc gcaaagacag cggcagcccg    4200
aaccccgccc gcggccacag cgtctgctcc acctccagct tgtacctgca ggatctgagc    4260
gccgccgcct cagagtgcat cgaccccctcg gtggtcttcc cctaccctct caacgacagc    4320
agctcgccca gtcctgcgc ctcgcaagac tccagcgcct tctctccgtc ctcggattct    4380
ctgctctcct cgacggagtc ctccccgcag ggcagcccg agcccctggt gctccatgag    4440
gagacaccgc ccaccaccag cagcgactct gaggaggaac aagaagatga ggaagaaatc    4500
gatgttgttt ctgtggaaaa gaggcaggct cctggcaaaa ggtcagagtc tggatcacct    4560
tctgctggag gccacagcaa acctcctcac agcccactgg tcctcaagag gtgccacgtc    4620
tccacacatc agcacaacta cgcagcgcct ccctccactc ggaaggacta tcctgctgcc    4680
aagagggtca agttggacag tgtcagagtc ctgagacaga tcagcaacaa ccgaaaatgc    4740
accagcccca ggtcctcgga caccgaggag aatgtcaaga ggcgaacaca caacgtcttg    4800
gagcgccaga ggaggaacga gctaaaacgg agcttttttg ccctgcgtga ccagatcccg    4860
gagttggaaa acaatgaaaa ggcccccaag gtagttatcc ttaaaaaagc cacagcatac    4920
atcctgtccg tccaagcaga ggagcaaaag ctcatttctg aagaggactt gttgcggaaa    4980
cgacgagaac agttgaaaca caaacttgaa cagctacgga actcttgtgc gtaaggacgt    5040
cgattaagaa aaacttaggg tgaaagttca tcgcggccgc ttgctagcag tctgacatgg    5100
ctgtcagcga cgcgctgctc ccatctttct ccacgttcgc gtctggcccg gcggaaggg    5160
agaagacact gcgtcaagca ggtgcccga ataaccgctg gcgggaggag ctctcccaca    5220
tgaagcgact tcccccagtg cttcccggcc gccctatga cctggcggcg gcgaccgtgg    5280
ccacagacct ggagagcggc ggagccggtg cggcttgcgg cggtagcaac ctggcgcccc    5340
tacctcggag agagaccgag gagttcaacg atctcctgga cctggacttt attctctcca    5400
attcgctgac ccatcctccg gagtcagtgg ccgccaccgt gtcctcgtca gcgtcagcct    5460
cctcttcgtc gtcgccgtcg agcagcggcc ctgccagcgc gccctccacc tgcagcttca    5520
```

```
cctatccgat ccgggccggg aacgacccgg gcgtggcgcc gggcggcacg ggcggaggcc    5580
tcctctatgg cagggagtcc gctccccctc cgacggctcc cttcaacctg gcggacatca    5640
acgacgtgag cccctcgggc ggcttcgtgg ccgagctcct gcggccagaa ttggacccgg    5700
tgtacattcc gccgcagcag ccgcagccgc caggtggcgg gctgatgggc aagttcgtgc    5760
tgaaggcgtc gctgagcgcc cctgcagcg agtacggcag cccgtcggtc atcagcgtca    5820
gcaaaggcag ccctgacggc agccaccgg tggtggtggc gccctacaac ggcgggccgc    5880
cgcgcacgtg ccccaagatc aagcaggagg cggtctcttc gtgcacccac ttgggcgctg    5940
gaccccctct cagcaatggc caccggccgg ctgcacacga cttcccctg gggcggcagc    6000 tccccagcag gactaccccg accctgggtc ttgaggaagt gctgagcagc agggactgtc    6060
accctgccct gccgcttcct cccggcttcc atccccaccc ggggcccaat tacccatcct    6120
tcctgcccga tcagatgcag ccgcaagtcc cgccgctcca ttaccaagag ctcatgccac    6180
ccggttcctg catgccagag gagcccaagc caaagagggg aagacgatcg tggccccgga    6240
aaaggaccgc cacccacact tgtgattacg cgggctgcgg caaaacctac acaaagagtt    6300
cccatctcaa ggcacacctg cgaacccaca caggtgagaa accttaccac tgtgactggg    6360
acggctgtgg atggaaattc gcccgctcag atgaactgac caggcactac cgtaaacaca    6420
cggggcaccg cccgttccag tgccaaaaat gcgaccgagc attttccagg tcggaccacc    6480
tcgccttaca catgaagagg cattttttaaa cgcgtcagag acctgcaaca atgtctcaag    6540
cagacaccac ctggcagtcg gagccaccgg gtcactcctt gtcttaaata agaaaaactt    6600
agggataaag tcccttagat ctagcctagg ttccccatgg cgggacacct ggcttcggat    6660
ttcgccttct cgcccctcc agtggtgga ggtgatgggc caggggggcc ggagccgggc    6720
tgggttgatc ctcggacctg gctaagcttc caaggccctc ctggagggcc aggaatcggg    6780
ccggggggtg ggccaggctc tgaggtgtgg gggattcccc catgccccc gccgtatgag    6840 ttctgtgggg ggatggcgta ctgtgggccc caggttggag tggggctagt gccccaaggc    6900
ggcttggaga cctctcagcc tgagggcgaa gcaggagtcg gggtggagag caactccgat    6960
ggggcctccc cggagccctg caccgtcacc cctggtgccg tgaagctgga aaggagaag    7020 ctggagcaaa acccggagga gtcccaggac atcaaagctc tgcagaaaga actgagcaa    7080 tttgccaagc tcctgaagca aagaggatc accctgggat atacacaggc cgatgtgggg    7140
ctcaccctgg gggttctatt tgggaaggta ttcagccaaa cgaccatctg ccgctttgag    7200
gctctgcagc ttagcttcaa gaacatgtgt aagctgcggc ccttgctgca gaagtgggtg    7260
gaggaagctg acaacaatga aaatcttcag gagatatgca aagcagaaac cctcgtgcag    7320
gcccgaaaga gaaagcgaac cagtatcgag aaccgagtga gaggcaacct ggagaatttg    7380
ttcctgcagt gcccgaaacc cacactgcag cagatcagcc acatcgccca gcagcttggg    7440
ctcgagaagg atgtggtccg agtgtggttc tgtaaccggc gccagaaggg caagcgatca    7500
agcagcgact atgcacaacg agaggatttt gaggctgctg gtctccttt ctcagggga    7560 ccagtgtcct ttcctctggc cccagggccc cattttggta ccccaggcta tgggagccct    7620
cacttcactg cactgtactc ctcggtccct ttccctgagg gggaagcctt tcccctgtc    7680 tccgtcacca ctctgggctc tcccatgcat tcaaactgag gacgtcagat ctgtatataa    7740
taagaaaaac ttagggtgaa agtgaggttg cgcggtattt tagctagccc gcatgtacaa    7800
catgatggag acggagctga agccgccggg cccgcagcaa acttcggggg gcggcggcgg    7860
caactccacc gcggcggcgg ccggcggcaa ccagaaaaac agcccggacc gcgtcaagcg    7920
```

```
gcccatgaat gccttcatgg tgtggtcccg cgggcagcgg cgcaagatgg cccaggagaa   7980
ccccaagatg cacaactcgg agatcagcaa gcgcctgggc gccgagtgga aacttttgtc   8040
ggagacggag aagcggccgt tcatcgacga ggctaagcgg ctgcgagcgc tgcacatgaa   8100
ggagcacccg gattataaat accggccccg gcggaaaacc aagacgctca tgaagaagga   8160
taagtacacg ctgcccggcg ggctgctggc cccggcggc aatagcatgg cgagcggggt    8220
cggggtgggc gccggcctgg gcgcgggcgt gaaccagcgc atggacagtt acgcgcacat   8280
gaacggctgg agcaacggca gctacagcat gatgcaggac cagctgggct acccgcagca   8340
cccgggcctc aatgcgcacg gcgcagcgca gatgcagccc atgcaccgct acgacgtgag   8400
cgccctgcag tacaactcca tgaccagctc gcagacctac atgaacggct cgcccaccta   8460
cagcatgtcc tactcgcagc agggcacccc tggcatggct cttggctcca tgggttcggt   8520
ggtcaagtcc gaggccagct ccagcccccc tgtggttacc tcttcctccc actccagggc   8580
gccctgccag gccggggacc tccgggacat gatcagcatg tatctccccg cgcgccgaggt  8640
gccggaaccc ccgcccccca gcagacttca catgtcccag cactaccaga gcggcccggt   8700
gcccggcacg gccattaacg gcacactgcc cctctcacac atgtgagacc ggtgtcggct   8760
ttgctgacac tagagtcatc tccgaacatc cacaatatct ctcagtctct tacgtctctc   8820
acagtattaa gaaaaaccca gggtgaatgg gaagcttgcc ataggtcatg gatgggcagg   8880
agtcctccca aaacccttct gacatactct atccagaatg ccacctgaac tctcccatag   8940
tcagggggaa gatagcacag ttgcacgtct tgttagatgt gaaccagccc tacagactaa   9000
aggacgacag cataataaat attacaaagc acaaattag gaacggagga ttgtcccctc    9060
gtcaaattaa gatcaggtct ctgggtaagg ctcttcaacg cacaataaag gatttagacc   9120
gatacacctt tgaaccgtac ccaacctact ctcaggaatt acttaggctt gatataccag   9180
agatatgtga caaaatccga tccgtcttcg cggtctcgga tcggctgacc agggagttat   9240
ctagtgggtt ccaggatctt tggttgaata tcttcaagca actaggcaat atagaaggaa   9300
gagagggta cgatccgttg caggatatcg gcaccatccc ggagataact gataaataca   9360
gcaggaatag atggtatagg ccattcctaa cttggttcag catcaaatat gacatgcggt   9420
ggatgcagaa gaccagaccg gggggaccccc tcgatacctc taattcacat aacctcctag   9480
aatgcaaatc atacactcta gtaacatacg gagatcttat catgatactg aacaagttga   9540
cattgacagg gtatatccta acccctgagc tggtcttgat gtattgtgat gttgtagagg   9600
gaaggtggaa tatgtctgct gcagggcatc tagataagaa gtccattggg ataacaagca   9660
aaggtgagga attatgggaa ctagtggatt ccctcttctc aagtcttgga gaggaaatat   9720
acaatgtcat cgcactattg gagcccctat cacttgctct catacaacta aatgatccag   9780
ttatacctct acgtgtgggca tttatgaggc atgtgttgac agagctacag gctgttttaa   9840
caagtaggga cgtgtacaca gatgctgaag cagacactat tgtggagtcg ttactcgcca   9900
ttttccatgg aacctctatt gatgagaaag cagagatctt ttccttcttt aggacatttg   9960
gccaccccag cttagaggct gtcactgccg ccgacaaggt aagggcccat atgtatgcac   10020
aaaaggcaat aaagcttaag accctatacg agtgtcatgc agttttttgc actatcatca   10080
taaatgggta tagagagagg catggcggac agtggccccc ctgtgacttc cctgatcacg   10140
tgtgtctaga actaaggaac gctcaagggt ccaatacggc aatctcttat gaatgtgctg   10200
tagacaacta tacaagtttc ataggcttca agtttcggaa gtttatagaa ccacaactag   10260
atgaagatct cacaatatat atgaaagaca aagcactatc ccccaggaag gaggcatggg   10320
```

```
actctgtata cccggatagt aatctgtact ataaagcccc agaatctgaa gagacccggc   10380
ggcttattga agtgttcata aatgatgaga atttcaaccc agaagaaatt atcaattatg   10440
tggagtcagg agattggttg aaagacgaga agttcaacat ctcgtacagt ctcaaagaga   10500
aagagatcaa gcaagagggt cgtctattcg caaaaatgac ttataagatg cgagccgtac   10560
aggtgctggc agagacacta ctggctaaag aataggagag ctgttcagc gaaaatggga    10620 tggttaaagg agagatagac ctacttaaaa gattgactac tctttctgtc tcaggagtcc   10680
ccaggactga ttcagtgtac aataactcta aatcatcaga gaagagaaac gaaggcatga   10740
aaaagaagaa ctctgggggg tactgggacg aaaagaagag gtccagacat gaattcaagg   10800
caacagattc atcaacagac ggctatgaaa cgttaagttg cttcctcaca acagacctca   10860
agaaatactg cttaaactgg agatttgaaa gtactgcatt gtttggtcag agatgcaacg   10920
agatatttgg cttcaagacc ttctttaact ggatgcatcc agtccttgaa aggtgtacaa   10980
tatatgttgg ggatccttac tgtccagtcg ccgaccggat gcatcgacaa ctccaggatc   11040
atgcagactc tggcattttc atacataatc ctagggggg catagaaggt tactgccaga    11100
agctgtggac cttaatctca atcagtgcaa tccacctagc agctgtgaga gtgggtgtca   11160
gggtctctgc aatggttcag ggtgacaatc aagctatagc cgtgacatca agagtacctg   11220
tagctcagac ttacaagcag aagaaaaatc atgtctataa ggagatcacc aaatattttg   11280
gtgctctaag acacgtcatg tttgatgtag ggcacgagct aaaattgaac gagaccatca   11340
ttagtagcaa gatgtttgtc tatagtaaaa gaatatacta tgatgggaag attttaccac   11400
agtgcctgaa agccttgacc aggtgtgtat tctggtccga gacactggta gatgaaaaca   11460
gatctgcttg ttcgaacatc tcaacatcca tagcaaaagc tatcgaaaat gggtattctc   11520
ctatactagg ctactgcatt gcgttgtata agacctgtca gcaggtgtgc atatcactag   11580
ggatgactat aaatccaact atcagcccga ccgtaagaga tcaatacttt aagggtaaga   11640
attggctgag atgtgcagtg ttgattccag caaatgttgg aggattcaac tacatgtcta   11700
catctagatg ctttgttaga aatattggag accccgcagt agcagccta gctgatctca    11760 aaagattcat cagagcggat ctgttagaca agcaggtact atacagggtc atgaatcaag   11820
aacccggtga ctctagcttt ctagattggg cttcagaccc ttattcatgt aacctcccgc   11880
attctcagag tataactacg attataaaga atatcactgc tagatctgtg ctgcaggaat   11940
ccccgaatcc tctactgtct ggtctcttca ccgagactag tggagaagag gatctcaacc   12000
tggcctcgtt cctatggac cggaaagtca tcctgccgag agtggctcat gagatcctgg     12060
gtaattcctt aactggagtt agggaggcga ttgcagggat gcttgatacg accaagtctc   12120
tagtgagatc cagcgttaag aaaggaggat tatcatatgg gatattgagg aggcttgtca   12180
attatgatct attgcagtac gagacactga ctagaactct caggaaaccg gtgaaagaca   12240
acatcgaata tgagtatatg tgttcagttg agctagctgt cggtctaagg cagaaaatgt   12300
ggatccacct aacttacggg agacccatac atgggctaga aacaccagac cctttagagc   12360
tcttgagggg aacatttatc gaaggttcag aggtgtgcaa gctttgcagg tctgagggag   12420
cagaccccat ctatacatgg ttctatctcc ctgacaatat agacctggac acgcttacaa   12480
acggatgtcc ggctataaga atcccctatt ttggatcagc cactgatgaa aggtcggaag   12540
cccaactcgg gtatgtaaga aatctaagca aacccgcaaa ggctgccatc cggatagcta   12600
tggtgtatac gtgggcctac gggactgatg agatatcgtg gatggaagcc gctcttatag   12660
cccaaacaag agctaatctg agcttagaga atctaaagct gctgactcct gtttcaacct   12720
```

```
ccactaatct atctcatagg ttgaaagata cggcaaccca gatgaagttc tctagtgcaa    12780
cactagtccg tgcaagtcgg ttcataacaa tatcaaatga taacatggca ctcaaagaag    12840
caggggagtc gaaggatact aatctcgtgt atcagcagat tatgctaact gggctaagct    12900
tgttcgagtt caatatgaga tataagaaag gttccttagg gaagccactg atattgcact    12960
tacatcttaa taacgggtgc tgtataatgg agtccccaca ggaggcgaat atcccccaa     13020 ggtccacatt agatttagag attacacaag agaacaataa attgatctat gatcctgatc    13080
cactcaagga tgtggacctt gagctattta gcaaggtcag agatgttgta catacagttg    13140
acatgactta ttggtcagat gatgaagtta tcagagcaac cagtatctgt actgcaatga    13200
cgatagctga tacaatgtct caattagata gagacaacct aaaagagatg atcgcgctag    13260
taaatgacga tgatgtcaac agcctgatta ctgagtttat ggtgattgat gttccttat    13320 tttgctcaac gttcgggggt attctagtca atcagtttgc atactcactc tacggcttaa    13380
acatcagagg aagggaagaa atatggggac atgtagtccg gattcttaaa gatacctccc    13440
acgcagttct aaaagtctta tctaatgctc tatctcatcc caaaatcttc aaacgattct    13500
ggaatgcagg tgtcgtggaa cctgtgtatg gcctaacct ctcaaatcag acaagatac     13560 tcttggccct ctctgtctgt gaatattctg tggatctatt catgcacgat tggcaagggg    13620
gtgtaccgct tgagatcttt atctgtgaca atgacccaga tgtggccgac atgaggaggt    13680
cctctttctt ggcaagacat cttgcatacc tatgcagcgt ggcagagata tctagggatg    13740
ggccaagatt agaatcaatg aactctctag agaggctcga gtcactaaag agttacctgg    13800
aactcacatt tcttgatgac ccggtactga ggtacagtca gttgactggc ctagtcatca    13860
aagtattccc atctactttg acctatatcc ggaagtcatc tataaagtg ttaaggacaa     13920 gaggtatagg agtccctgaa gtcttagaag attgggatcc cgaggcagat aatgcactgt    13980
tagatggtat cgcggcagaa atacaacaga atattccttt gggacatcag actagagccc    14040
cttttttggg gttgagagta tccaagtcac aggtactgcg tctccggggg tacaaggaga    14100
tcacaagagg tgagataggc agatcaggcg ttggtctgac gttaccattc gatgaagat     14160 atctatctca ccagctgagg ctctttggca tcaacagtac tagctgcttg aaagcacttg    14220
aacttaccta cctattgagc cccttagttg acaaggataa agataggcta tatttagggg    14280
aaggagctgg ggccatgctt tcctgttatg acgctactct tggcccatgc atcaactatt    14340
ataactcagg ggtatactct tgtgatgtca atgggcagag agagttaaat atatatcctg    14400
ctgaggtggc actggtggga aagaaattaa acaatgttac tagtctgggt caaagagtta    14460
aagtgttatt caacgggaat cctggctcga catggattgg aaatgatgag tgtgaggctt    14520
tgatttggaa tgaattgcag aatagctcga taggcctagt ccactgtgac atggagggag    14580
gagatcataa ggatgatcaa gttgtactgc atgagcatta cagtgtaatc cggatcgcgt    14640
atctggtggg ggatcgagac gttgtgctta taagcaagat tgctcctagg ctgggcacgg    14700
attggaccag gcagctcagc ctatatctga gatactggga cgaggttaac ctaatagtgc    14760
ttaaaacatc taaccctgct tccacagaga tgtatctcct atcgaggcat cccaaatctg    14820
acattataga ggacagcaag acggtgttag ctagtctcct cccttttgtca aaagaagata    14880 gcatcaagat agaaaagtgg atcttaatag agaaggcaaa ggctcacgaa tgggttactc    14940
gggaattgag agaaggaagc tcttcatcag ggatgcttag accttaccat caagcactgc    15000
agacgtttgg ctttgaacca aacttgtata aattgagcag agatttcttg tccaccatga    15060
acatagctga tacacacaac tgcatgatag cttttcaacag ggttttgaag gatacaatct    15120
```

```
tcgaatgggc tagaataact gagtcagata aaaggcttaa actaactggt aagtatgacc  15180
tgtatcctgt gagagattca ggcaaattga agacagtttc tagaagactt gtgctatctt  15240
ggatatcttt atctatgtcc acaagattgg taactgggtc attccctgac cagaagtttg  15300
aagcaagact tcaattggga atagtttcat tatcatcccg tgaaatcagg aacctgaggg  15360
ttatcacaaa aactttatta gaccggtttg aggatattat acatagtata acgtacagat  15420
tcctcaccaa agaaataaag attttgatga agattttagg ggcagtcaag atgttcgggg  15480
ccaggcaaaa tgaatacacg accgtgattg atgatggatc actgggtgat atcgagccat  15540
atgacagctc gtaataccgg ttatcaccaa aacatggaag cacttacgat tcaccaaaac  15600
atggaagcac ttaggtacct caccaaaaca tggaagcact tacgattcac caaaacatgg  15660
aagcacttaa ccggttccct atcgtgcaga acgatcgaag ctccgcggta cctggaagtc  15720
ttggactgat ccatatgaca atagtaagaa aaacttacaa gaagacaaga aaatttaaaa  15780
gaatacatat ctcttaaact cttgtctggt                                   15810
```